United States Patent [19]
Caldwell

[11] Patent Number: 5,418,051
[45] Date of Patent: May 23, 1995

[54] INTERNALLY COATED WEBS

[75] Inventor: J. Michael Caldwell, Escondido, Calif.

[73] Assignee: Fabric Coating Corporation, Carlsbad, Calif.

[21] Appl. No.: 17,855

[22] Filed: Feb. 16, 1993

Related U.S. Application Data

[63] Continuation of Ser. No. 319,778, Mar. 10, 1989, Pat. No. 5,004,643, which is a continuation-in-part of Ser. No. 167,630, Mar. 14, 1988, abandoned, Ser. No. 167,643, Mar. 14, 1988, abandoned, Ser. No. 167,797, Mar. 14, 1988, abandoned, and Ser. No. 167,869, Mar. 14, 1988, abandoned.

[51] Int. Cl.$^6$ .................. B32B 5/32; D06M 15/643; D06M 15/70
[52] U.S. Cl. .................. 428/240; 427/358; 427/359; 427/369; 427/387; 427/389; 427/389.9; 427/391; 427/393.3; 427/393.4; 427/412; 428/241; 428/242; 428/244; 428/246; 428/248; 428/252; 428/260; 428/272; 428/274; 428/283; 428/286; 428/287; 428/290; 428/306.6; 428/308.4; 428/311.1; 428/311.5; 428/311.7; 428/315.7; 428/315.9; 428/422; 428/425.5; 428/447; 428/904; 428/913

[58] Field of Search ............... 427/358, 359, 369, 387, 427/389, 389.9, 391, 393.3, 393.4, 412; 428/240, 241, 242, 244, 246, 248, 252, 260, 272, 274, 283, 286, 287, 290, 306.6, 308.4, 311.1, 311.5, 311.7, 315.7, 315.9, 422, 425.5, 447, 904, 913

[56] References Cited

U.S. PATENT DOCUMENTS

| | | | |
|---|---|---|---|
| 4,560,611 | 12/1985 | Naka et al. | 428/266 |
| 5,004,643 | 4/1991 | Caldwell | 428/246 |
| 5,209,965 | 5/1993 | Caldwell | 428/260 |

*Primary Examiner*—James C. Cannon
*Attorney, Agent, or Firm*—Stanley A. Becker

[57] ABSTRACT

An improved process is provided for treating a porous web (especially fabric) to produce a novel silicone polymer internally coated web. In the process, a starting curable liquid silicone polymer is coated under pressure upon one surface of the web, and the web is then subjected to localized shear forces sufficient to move the silicone polymer composition into interior portions of the web and to distribute the silicone polymer composition generally uniformly therwithin in such planar region. Excess silicone polymer composition is wiped away from a web surface. Thereafter, the resulting web is heated or irradiated to cure the silicone polymer. Preferably a web is preliminarily impregnated with a fluorochemical. Webs procuded by this process are breathable, waterproof or highly water repellent, and flexible.

86 Claims, 14 Drawing Sheets

FUNCTION OF θ AND i AS INDICATED ON DIAGRAM FOR ADHESION, PENETRATION, AND SPREADING, RESPECTIVELY (a) PSEUDOPLASTIC FLOW
D SHEAR RATE (SEC$^{-1}$)

(b) DILATANT FLOW
D SHEAR RATE (SEC$^{-1}$)

(c) THIXOTROPIC LOOP
D SHEAR RATE (SEC$^{-1}$)

(d) LAMINAR VS. TURBULENT FLOW
D SHEAR RATE (SEC$^{-1}$)

INTERNALLY COATED WEBS

REFERENCE TO RELATED PATENT APPLICATIONS

This application is a continuation of application Ser. No. 07/319,778, filed Mar. 10, 1989, now U.S. Pat. No. 5,004,643 which application is a continuation-in-part of my earlier filed U.S. patent application Ser. Nos. 167,630; 167,643; 167,797; and 167,869 all filed Mar. 14, 1988, all now abandoned.

BACKGROUND OF THE INVENTION

1. Field of the Invention

The present invention generally concerns porous fibrous webs (especially fabrics) that are modified in their properties by incorporation thereinto an internal layer of silicone polymer. Such webs are prepared by pressurized impregnation methods.

2. Prior Art

In the prior art, it has been proposed to treat porous webs, especially fabrics, with silicone resins and also with fluorochemicals.

Conventional treatments of webs fall into the general categories of (i) surface coatings and (ii) saturations and impregnations.

For example, U.S. Pat. Nos. 3,436,366; 3,639,155; 4,472,470; 4,500,584; and 4,666,765 disclose silicone coated fabrics. Silicone coatings are known to exhibit relative inertness to extreme temperatures of both heat and cold and to be relatively resistant to ozone and ultraviolet light. Also, a silicone coating can selectively exhibit resistance to soiling, strength enhancement, and/or flame retardancy.

Fluorochemical treatment of webs is known to impart properties, such as soil resistance, grease resistance, and the like.

Prior art fluorochemical and silicone fabric treatment evidently each can protect only that side of the fabric upon which they are disposed. Such treatments characteristically significantly alter the hand, or tactile feel, of the treated side. Prior silicone fabric coatings typically degrade the tactile finish, or hand, of the fabric and give the coated fabric side a rubberized finish which is not appealing for many fabric uses, particularly garments.

U.S. Pat. No. 4,454,191 describes a waterproof and moisture-conducting fabric coated with a hydrophilic polymer. The polymer is a compressed foam of an acrylic resin modified with polyvinyl chloride or polyurethane and serves as a sort of "sponge" soaking up excess moisture vapor.

Other microporous polymeric coatings have been used in prior art attempts to make a garment breathable, yet waterproof.

Various polyorganosiloxane compositions are taught in the prior art that can be used for making coatings that impart water-repellency to fabrics. Typical of such teachings is the process described in U.S. Pat. No. 4,370,365 which describes a water repellant agent comprising, in addition to an organohydrogenpolysiloxane, either one or a combination of linear organopolysiloxanes containing alkene groups, and a resinous organopolysiloxane containing tetrafunctional and monofunctional siloxane units. The resultant mixture is catalyzed for curing and dispersed into an aqueous emulsion. The fabric is dipped in the emulsion and heated. The resultant product is said to have a good "hand" and to possess waterproofness.

This type of treatment for rendering fabrics water repellant without affecting their "feel" is common and well known in the art. However, it has not been shown that polyorganosiloxanes have been coated on fabrics in such a way that both high levels of resistance to water by the fibers/filaments and high levels of permeability to water vapor are achieved. As used herein, the term "high levels of permeability to water vapor" has reference to a value of at least about 500 gms/m$^2$/day, as measured by ASTM E96-80B. Also, as used herein, the term "high level of waterproofness" is defined by selective testing methodologies discussed later in this specification. These methodologies particularly deal with water resistance of fabrics and their component fibers.

Porous webs have been further shown to be surface coated in, for example, U.S. Pat. Nos. 4,478,895; 4,112,179; 4,297,265; 2,893,962; 4,504,549; 3,360,394; 4,293,611; 4,472,470; and 4,666,765. These surface coatings impart various characteristics to the surface of a web, but do not substantially impregnate the web fibers. Such coatings remain on the surface and do not provide a film over the individual internal fibers and/or yarn bundles of the web. In addition, such coatings on the web surface tend to wash away quickly.

Prior art treatments of webs, by saturation or impregnation also suffer from limitations. Saturation, such as accomplished by padbath immersion, or the like, is capable of producing variable concentrations of a given saturant chemical.

In order to treat a flexible web, by heavy saturation, or impregnation, with a polymer material, such as a silicone resin, the prior art has suggested immersion of the flexible web, or fabric, in a padbath, or the like, using a low viscosity liquid silicone resin so that the low viscosity liquid can flow readily into, and be adsorbed or absorbed therewithin. The silicone resin treated product is typically a rubberized web, or fabric, that is very heavily impregnated with silicone. Such a treated web is substantially devoid of its original tactile and visual properties, and instead has the characteristic rubbery properties of a cured silicone polymer.

U.S. Pat. No. 2,673,823 teaches impregnating a polymer into the interstices of a fabric and thus fully filling the interstices. This patent provides no control of the saturation of the fabric. It teaches full saturation of the interstices of the fabric.

The prior art application of liquid or paste compositions to textiles for purposes of saturation and/or impregnation is typically accomplished by an immersion process. Particularly for flexible webs, including fabric, an immersion application of a liquid or paste composition to the web is achieved, for example, by the so-called padding process wherein a fabric material is passed first through a bath and subsequently through squeeze rollers in the process sometimes called single-dip, single-nip padding. Alternatively, for example, the fabric can be passed between squeeze rollers, the bottom one of which carries the liquid or paste composition in a process sometimes called double-dip or double-nip padding.

Coating at a predetermined thickness can be achieved by using precision-controlled deposition of coating material followed by passage through a pair of opposed scraping knives. The knives smooth the coating and maintain the thickness of the coating to a desired thickness. For example, it is possible to apply a relatively thick silicone liquid elastomer coating to a rough web, typically of fiberglass, in order to make architectural fabric as is taught in U.S. Pat. No. 4,666,765. In this example, the drag knives are set to a thickness of about 2 to 10 mils thicker than the web thickness. This setting, depending on the coating speed, can yield a base coat thickness of approximately 3 to 12 mils thicker than the web thickness.

Various types of coatings, and various coating thicknesses, are possible. However, a general principle of coating machinery is that the coating material is swept, or dragged, along the surface of the fabric. No special attention is normally given to any pressured forcing of the coating into the fabric, therein making the coating also serve as an impregnant. Of course, some coating will be urged into surface regions of the fabric by the coating process. Generally, however, application of high transversely exerted (against a fiber or web surface) forces at the location of the coating deposition and/or smoothing is not desired in the prior art processes because it is the goal of the prior art coating processes to leave a definite thickness of coating material upon a fabric, and not to scrape the fabric clean of surface-located coating material.

One prior art silicone resin composition is taught by U.S. Pat. Nos. 4,472,470 and 4,500,584, and includes a vinyl terminated polysiloxane, typically one having a viscosity of up to about 2,000,000 centipoises at 25° C., and a resinous organosiloxane polymer. The composition further includes a platinum catalyst, and an organohydrogenpolysiloxane crosslinking agent, and is typically liquid. Such composition is curable at temperatures ranging from room temperature to 100° C. or higher depending upon such variables as the amount of platinum catalyst present in the composition, and the time and the temperature allowed for curing.

Such compositions may additionally include fillers, including finely divided inorganic fillers. Silicone resin compositions that are free of any fillers are generally transparent or translucent, whereas silicone resin compositions containing fillers are translucent or opaque depending upon the particular filler employed. Cured silicone resin compositions are variously more resinous, or hard, dependent upon such variables as the ratio of resinous copolymer to vinyl terminated polysiloxane, the viscosity of the polysiloxane, and the like.

Curing (including polymerization and crosslinking) can encompass the same reactions. However, in the fabric finishing arts, such terms can be used to identify different phenomena. Thus, controllable and controlled curing, which is taught by the prior art, may not be the same as control of crosslinking. In the fabric finishing arts, curing is a process by which resins or plastics are set in or on textile materials, usually by heating. Crosslinking may be considered to be a separate chemical reaction from curing in the fabric finishing arts. Crosslinking can occur between substances that are already cured. Crosslinking can stabilize fibers, such as cellulosic fibers through chemical reaction with certain compounds applied thereto. Crosslinking can improve mechanical factors such as wrinkle performance. Polymerization can refer to polymer formation or polymer growth.

SUMMARY OF THE INVENTION

This invention relates to a flexible porous web which contains an internal coating of a silicone polymer composition.

The silicone polymer composition has a viscosity that is sufficient to achieve an internal coating of the web. Generally, the viscosity is greater than about 1000 centipoise and less than about 2,000,000 centipoise. Such composition, when cured, is preferably elastomeric.

Preferably, a fluorochemical is impregnated into the web before the silicone polymer is applied.

In a web of this invention the quantity of silicone polymer can vary widely. The silicone polymer composition is present in an amount that is sufficient to achieve an internal coating of the web. Generally, this amount is in the range of about 5 to about 200 weight percent of the weight of the untreated web or fibers. When present, the quantity of fluorochemical is in the range of about 0.01 to about 5 weight percent of the weight of the untreated web or fibers. When, as is preferred, a wed incorporates both a fluorochemical and a silicone polymer, they are present in an amount sufficient to achieve an internal coating of the web. Generally, the total weight of fluorochemical and silicone polymer is in the range of about 5 to about 200 weight percent of the weight of the untreated web.

Notwithstanding the large amount of silicone present in webs of the present invention, they surprisingly retain porosity, breathability, flexibility, hand and other characteristics similar to untreated webs while exhibiting improved characteristics such as water repellancy, rewashability, service life, abrasion resistance and durability.

The porous webs are generally flat or planar. The webs can comprise fibers in the form of monofilaments, yarns, staples, or the like. The web can also be comprised of a matrix having open cells or pores therein.

The web may be a fabric which is woven or nonwoven with fibers that can be of any desired composition. The web will generally be tensionable, but not too weak or elastomeric to be processed in accordance with the teachings of the present invention.

The web fibers are preferably comprised of a synthetic organic polymer; however, fibers comprised of natural fibrous materials can be used. Presently preferred synthetic polymers include polyamides (nylons), polyesters, such as polyethylene terephthalate, polyolefins such as polypropylene and polyethylene, acrylics, regenerated cellulose, cellulose acetates, and the like. When used, presently preferred natural fibers include cotton, linen, wool, and silk. Blends of these fibers, e.g., polyester/cotton can also be used.

Webs of the present invention contain a curable silicone polymer impregnant that is present as a film, or coating, or layer within a web that envelopes at least a portion of the fibers or cell or pore walls of the web. The interstices or open cells in the region of the internal coating are mostly filled or plugged by impregnant. The outer surfaces of the web are preferably substantially free of impregnant. However, the web remains breathable and is either water resistant or waterproof. The thickness of the film, coating or layer is generally in the range of 0.01 to 50 microns.

At a microscopic level, a web of the present invention, for example, a fabric, can be regarded as being a complex structure, but generally the internal layer is discernable under microscopic examination as shown in the accompanying scanning electron microscope photographs that will be discussed hereinafter.

Silicone polymer which substantially, completely encapsulates a web's fibers or lines its cell or pore walls and forms an internal layer means, that the silicone polymer is located mostly upon surface portions of the interior of the web.

Depending upon the conditions used to produce it, a web produced in accordance with the present invention can characteristically and preferably exhibit a soft hand and flexibility that is comparable to the hand and flexibility of the untreated web. In some cases, the differece in hand between the treated and untreated webs may not be perceptible. This is particularly surprising in view of the substantial amount of silicone polymer being added to the web. A treated web has a breathability which, by a present preference, can approach that of the untreated web notwithstanding the relatively large amount of silicone polymer present.

A silicone polymer composition having a viscosity in the range above indicated is used to produce the treated webs. If desired, additives can be admixed with such a composition to adjust and improve properties of such composition or web, such as viscosity and/or rheology, combustibility, reflectivity, flexibility, conductivity, light fastness, mildew resistance, rot resistance, stain resistance, grease resistance, and the like. In general, a web of this invention exhibits enhanced durability.

A web of the present invention preserves much, or even substantially all, of its original untreated hand even after an extended period of use while demonstrating excellent abrasion resistance. In contrast, an untreated web typically loses its original hand and displays reduced abrasion resistance after an extended period of use. This is achieved by the formation of an internal layer that prevents new fiber surfaces from being exposed, thereby minimizing the amount of untreated surfaces that degrade much faster than the treated fibers.

A web of this invention can undergo a large number of machine washings with detergent without experiencing appreciable or significant change or deterioration.

The silicone polymer composition prolongs the use and service life of a web, usually by at least an order of magnitude, depending on such factors as web type, extent and type of treatment by the teachings of this invention, and the like.

Optionally, and as indicated above, agents or additives carried by the silicone polymer composition into a web can be stably fixed in the web with the cured silicone polymer. For example, agents such as ultraviolet light absorbers, dulling agents, reflectivity enhancers, and the like, which modify a web's response to light and radiation are desirably located substantially upon the surfaces of the web's fibers. When these agents are incorporated into the enveloping silicone polymer film, it appears that then they are retained where they are deposited.

A present preference in the practice of this invention is to employ a silicone polymer composition that contains a benzophenone.

In addition, the present invention is directed to processes for making silicone polymer internally coated webs. Such processes involve tensioning a porous, flexible web, applying a curable silicone polymer composition thereto, and then moving a generally uniformly applied localized shear force over and against one surface of the tensioned web. The shear force is sufficient to shear thin the silicone polymer, to distribute the silicone polymer composition within the web as an internal coating in a region extending generally in spaced, parallel relationship to at least one face of the web and to generally envelop surface portions of at least some of the web fibers or form a lining of the cells or pores of the web. The web is then optionally interveningly stored, or is (preferably) immediately subjected to curing conditions (heat, moisture and/or radiation) which converts the polymer composition as deposited in the web into a solid elastomeric polymer.

Various other and further features, embodiments, and the like which are associated with the present invention will become apparent and better understood to those skilled in the art from the present description considered in conjunction with the accompanying drawings wherein presently preferred embodiments of the invention are illustrated by way of example. It is to be expressly understood, however, that the drawings and the associated accompanying portions of this specification are provided for purposes of illustration and description only, and are not intended as limitations on the invention.

DESCRIPTION OF THE PREFERRED EMBODIMENTS

Figure 1:
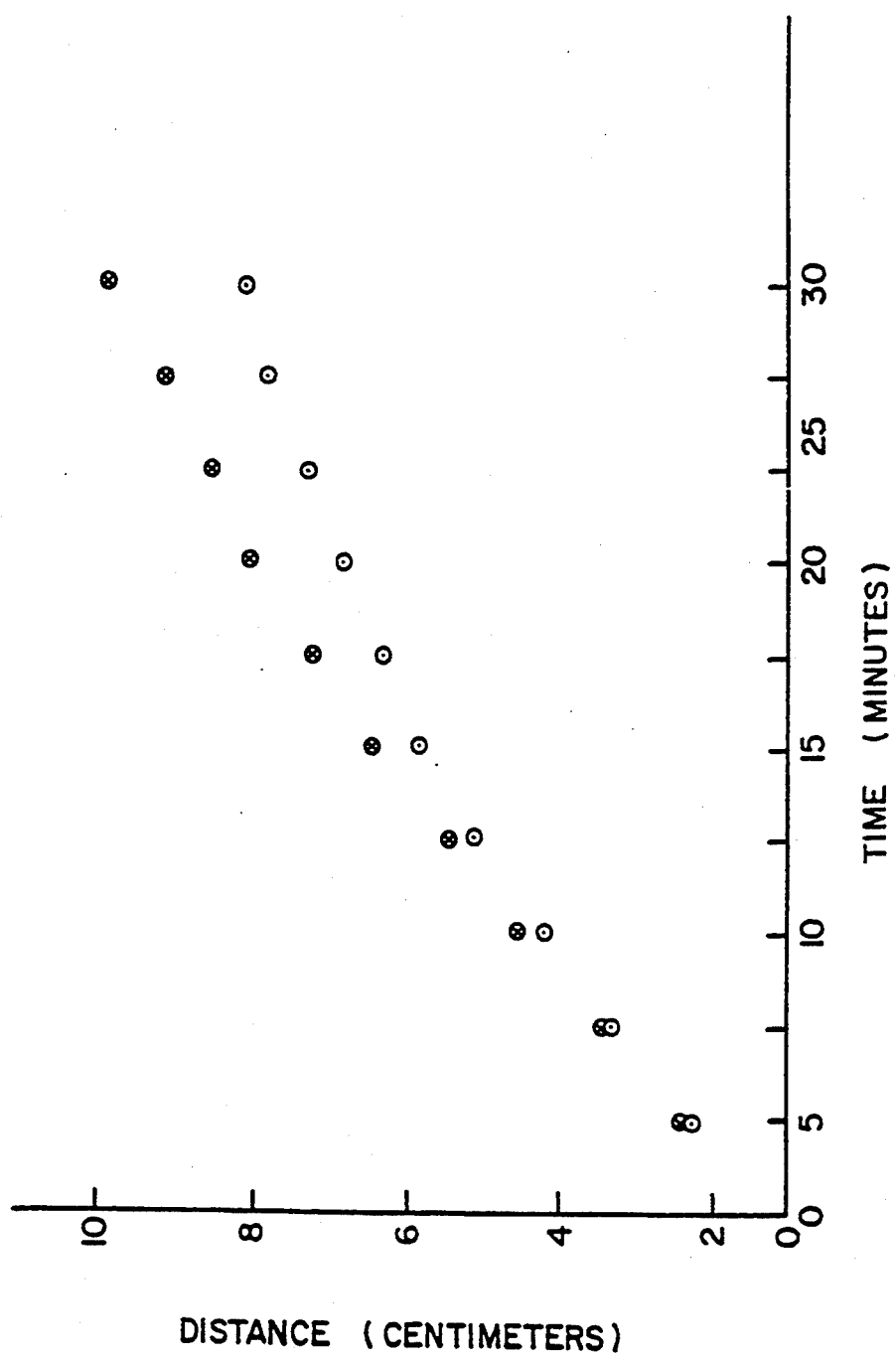
FIG. 1 is a graphical plot illustrating the flow of the silicone polymer composition over time upon and in fabrics both pretreated and untreated with water repellent chemicals, such as fluorochemicals.

Flexible porous webs usable in the practice of this invention can be classified into two general types:
(A) Fibrous webs; and
(B) Substrates having open cells or pores.

A porous, flexible fibrous web is comprised of a plurality of associated or interengaged fibers having interstices defined therebetween. Preferred fibrous webs are (woven or non-woven) fabrics.

Other substrates are comprised of a matrix having open cells or pores therein such as foams or synthetic leathers.

The term "fiber" as used herein refers to a long, pliable, cohesive, natural or man-made (synthetic) thread-like object, such as a monofilament, staple, filament, or the like. A fiber usable in this invention preferably has a length at least 100 times its diameter or width. Fibers can be regarded as being in the form of units which can be formed by known techniques into yarns or the like. Fibers can be formed by known techniques into woven or non-woven webs (especially fabrics) including weaving, knitting, braiding, felting, twisting, matting, needling, pressing, and the like. Preferably, fibers, such as those used for spinning, as into a yarn, or the like, have a length of at least about 5 millimeters. Fibers such as those derived from cellulosics of the type produced in paper manufacture can be used in combination with longer fibers as above indicated, as those skilled in the art will readily appreciate.

The term "filament" as used herein refers a fiber of indefinite length.

The term "yarn" as used herein refers to a continuous strand comprised of a multiplicity of fibers, filaments, or the like in a bundled form, such as may be suitable for knitting, weaving or otherwise used to form a fabric. Yarn occurs as a number of fibers that are twisted together (spun yarn) or a number of filaments that are laid together without twist (a zero-twist yarn).

A flexible porous web used as a starting material in this invention is generally and typically, essentially planar or flat and has generally opposed, parallel facing surfaces. Such a web is a three dimensional structure comprised of a plurality of fibers with interstices therebetween or a matrix having open cells or pores therein. The matrix can be comprised of polymeric solids including fibrous and non-fibrous elements.

The term "web" as used herein is intended to include fabrics and refers to a sheet-like structure (woven or non-woven) comprised of fibers. Included with the fibers can be non-fibrous elements, such as particulate fillers, binders, dyes, sizes and the like in amounts that do not substantially affect the porosity or flexibility of the web. While preferably, at least 50 weight percent of a web used in the practice of the present invention is fibers, more preferred webs have at least about 85 weight percent of their structure as fiber. It is presently preferred that webs be untreated with any sizing agent, coating, or the like, except as taught herein. The web may comprise a laminated fabric and a non-woven porous substrate.

Non-fibrous elements, such as particulate fillers, binders, dyes, sizes and the like can be added to fibers in a web. Preferred webs have at least about 85% of their structure comprised of fibrous or fiber materials and are untreated with any sizing agent, coating, or the like.

Two principal classes of substrates having open pores or cells may be utilized in the present invention: leathers (including natural leathers, and man-made or synthetic leathers), and foamed plastic sheets (or films) having open cells.

Foamed plastic sheet or film substrates are produced either by compounding a foaming agent additive with resin or by injecting air or a volatile fluid into the still liquid polymer while it is being processed into a sheet or film. A foamed substrate has an internal structure characterized by a network of gas spaces, or cells, that make such foamed substrate less dense than the solid polymer. The foamed sheets or film substrates used as starting materials in the practice of this invention are flexible, open-celled structures.

The class of foamed substrate structures known as "structural foams" are not suitable for use in the practice of this invention since such structures involve a solid skin which is believed to be substantially non-porous that is integral with and overlies a cellular core.

Natural leathers suitable for use in this invention are typically split hides.

Synthetic leathers have wide variations in composition (or structure) and properties, but they look like leather in the goods in which they are used. For purposes of technological description, synthetic leathers can be divided into two general categories: coated fabrics and poromerics.

Synthetic leathers which are poromerics are manufactured so as to resemble leather closely in breathability and moisture vapor permeability, as well as in workability, machinability, and other properties. The barrier and permeability properties normally are obtained by manufacturing a controlled microporous (open celled) structure.

Synthetic leathers which are coated fabrics, like poromerics, have a balance of physical properties and economic considerations. Usually the coating is either vinyl or urethane. Vinyl coatings can be either solid or expanded vinyl which has internal air bubbles which are usually a closed-cell type of foam. Because such structures usually have a non-porous exterior or front surface or face, such structures display poor breathability and moisture vapor transmission. However, since the interior or back surface or face is porous, such a coated fabric can be used in the practice of this invention by applying the impregnant silicone polymer to the back fact.

The fibers utilized in a porous flexible web employed in the practice of the present invention can be of natural or synthetic origin. Mixtures of natural fibers and synthetic fibers can also be used. Examples of natural fibers include cotton, wool, silk, jute, linen, and the like. Examples of synthetic fibers include rayon, acetate, polyesters (including polyethyleneterephthalate), polyamides (including nylon), acrylics, olefins, aramids, azlons, glasses, modacrylics, novoloids, nytrils, rayons, sarans, spandex, vinal, vinyon, and the like.

The term "impregnation", or "impregnate", as used herein, refers to forcing a liquid substance into a porous solid, such as a flexible web or substrate.

With respect to the fluorochemical liquid dispersions (or solutions) used for web pretreatment, the term "impregnation" refers to the penetration of such dispersions into a porous web, and to the distribution of such dispersions in a preferably, substantially uniform and controlled manner in such web, particularly as regards the surface portions of the individual web component structural elements and fibers.

With respect to the silicone polymer compositions used in this invention, the term "impregnation" refers to the penetration of such polymeric composition into a porous web, to the distribution of such composition in a controlled manner through such web, and to the resultant, at least partial envelopment of at least a portion of the fibers of such web by such composition in accordance with the present invention.

The term "coating" as used herein, refers to a generally continuous film or layer formed by a material over or on a surface.

The term "internally coated" as used herein, refers to the forming of a film or layer located within a porous solid in a specified region, such as a planar region extending interiorly through a porous web or substrate in spaced, parallel relationship to a surface thereof. Such film or layer envelopes, and/or surrounds, and/or impregnates individual fibers or lines cell or pore walls of the porous web or substrate in the specified region.

The term "envelope" as used herein, refers to the partial or complete surrounding, encasement, or enclosing by a discrete layer, film, coating, or the like, of exposed surface portions of at least some individual fiber or lining of a cell or pore wall of a porous web. Such a layer can sometimes be contiguous or integral with other portions of the same enveloping material which becomes deposited on internal areas of a web which are adjacent to such enveloping layer, enveloped fiber, lined cell or pore wall, or the like.

The term "elastomeric" as used herein refers to the ability of a cured silicone polymer impregnated web to stretch and return to its original state.

A characteristic of a silicone polymer composition, or impregnant, that is used for impregnation into a web or substrate in accordance with the teachings of this invention is that apparently only a minimum quantity of the impregnant appears actually to enter into the fibers, cells or pores comprising such web or substrate. The exact amount of impregnant which enters into individual fibers, cells or pores is unknown, but is now estimated to be typically below about 10 weight percent of the total quantity of impregnant applied to a web or substrate, with the remainder of the impregnant appearing to comprise mainly deposits on and around fibers, cells or pores of a web.

The term "curing", or "cure", as used herein, refers to a change in state, condition, and/or structure in a material, such as a curable silicone polymer composition that is usually, but not necessarily, induced by at least one applied variable, such as time, temperature, radiation, presence and quantity in such material of a curing catalyst or curing accelerator, or the like. In the occurrence of curing in any case, such as the curing of such a polymer composition that has been impregnated into a porous flexible substrate or web, the components of such a composition may experience occurrence of one or more of complete or partial (a) polymerization, (b) cross-linking, or (c) other reaction, depending upon the nature of the composition being cured, application variables, and presumably other factors.

The term "filled" as used herein in relation to interstices or open cells, and to the amount of silicone polymer composition therein in a given web or substrate, designates the presence of such composition therein. When a given interstice or open cell is totally taken up by such composition, it is "completely filled" or "plugged".

Measurements of the degree of envelopment, interstice fillage, plugging, or the like in an internal coating are conveniently made by microscopy, or preferably by conventional scanning electron microscopy (SEM) techniques. Because of the nature of such measuring by SEM for purposes of the present invention, "a completely filled" interstice or open cell can be regarded as a "plugged" interstice or open cell.

A flexible, porous fibrous web is preferably untreated or scoured before being treated in accordance with the present invention. Preferably a web is preliminarily treated, preferably saturated, for example, by padding, to substantially uniformly impregnate the web with a fluorochemical. Typically, and preferably, the treating composition comprises a dispersion of fluorochemical in a liquid carrier. The liquid carrier is preferably aqueous and can be driven off with heat after application. The treating composition has a low viscosity, typically comparable to the viscosity of water or less. After such a treatment, it is presently preferred that the resulting treated web exhibits a contact angle with water measured on an outer surface of the treated web that is greater than about 90 degrees. The treated web preferably contains fluorochemical substantially uniformly distributed therethrough. Thus, the fluorochemical is believed to be located primarily on and in the individual fibers, cells or pores with the web interstices or open cells being substantially free of fluorochemical.

A presently preferred concentration of fluorochemical in a treatment composition is typically in the range of about 1 to about 10% fluorochemical by weight of the total treating composition weight, and more preferably is about 2.5% of an aqueous treating dispersion. Web weight add-ons of the fluorochemical can vary depending upon such factors as the particular web treated, the silicone polymer impregnant to be utilized in the next step of the treatment process of this invention, the ultimate intended use and properties of the treated web of this invention, and the like. The fluorochemical weight add-on is typically in the range of about 0.01 to about 5% of the weight of the untreated web. After fluorochemical impregnation, the web is preferably squeezed to remove excess fluorochemical composition after which the web is heated or otherwise dried to evaporate carrier liquid and thereby also accomplish fluorochemical insolubilization or sintering, if permitted or possible with the particular composition used.

The fluorochemical treated web is thereafter impregnated under pressure by the procedures taught by this invention, with a predetermined amount of a curable silicone polymer impregnant composition to form a web whose fibers, cells or pores are at least partially enveloped or lined with the curable silicone polymer impregnant, whose web outer surfaces are substantially free of the curable impregnant, whose web interstices or open cells are not completely filled with the curable impregnant and which contains an internal layer of silicone polymer. The curable impregnant composition utilized preferably exhibits a viscosity greater than 1,000 centipoise and less than 2,000,000 centipoise at rest at 25° C. at a shear rate of 10 reciprocal seconds.

The silicone polymer impregnant composition can include conventional additives.

The fluorochemical residue that remains after fiber treatment may not be exactly evenly distributed throughout the web, but may be present in the web in certain discontinuities. For example, these discontinuities may be randomly distributed small areas upon an individual fiber's surface. However, the quantity and distribution of fluorochemical through a web is believed to be largely controllable. Some portions of the fluorochemical may become dislodged from the web and migrate through the silicone polymer due to the forces incurred by cause the shear thinning of the silicone polymer.

The curable silicone impregnant composition is believed to be typically polymeric, to be usually a mixture of co-curable polymers and oligomers, and to include a catalyst to promote the cure.

The silicone polymer impregnant composition can include, as additive components, polyurethanes, fluorosilicones, silicone-modified polyurethanes, acrylics, polytetrafluoroethylehe-containing materials, and the like.

The web is thereafter cured to convert the curable composition into a solid elastomeric polymer.

It is to be understood that the depth of silicone polymer impregnation into a web can be controlled by the application procedures herein described to provide a selective placement of the silicone polymer impregnant within the substrate or web. This allows the shear thinning, i.e., viscosity reduction, action to take place throughout the web.

The silicone polymer composition is theorized to be caused to flow and distribute itself over fibers, cells or pores in a web under the influence of the processing conditions provided by this invention. This flow and distribution is further theorized to be facilitated and promoted by the presence of a fluorochemical which has been preliminarily impregnated into a web, as taught herein. The amount of fluorochemical or fluorochemical residue in a web is believed to influence the amount, and the locations, where the liquid silicone polymer impregnant will collect and deposit, and produce an internal coating in the web. However, there is no intent to be bound herein by theory.

Some portion of the residue of fluorochemical resulting from a preliminary web saturating operation is theorized to be present upon a treated fiber's surfaces after envelopment of fibers, cells or pores by the silicone polymer has been achieved during internal web coating by the practice of this invention. This is believed to be demonstrated by the fact that a web of this invention still exhibits an enhanced water and oil repellency, such as is typical of fluorochemicals in porous webs. It is therefore believed that the fluorochemicals are affecting the adherence of the silicone polymer as a thin film enveloping layer about the treated fibers, cells or pores as well as facilitating liquid silicone polymer impregnant pressurized flow within and about the interstices or open cells of the web being treated so that the silicone can assume its position enveloping the fibers or lining the cells or pores of the substrate.

The exact interrelationship between the silicone polymer film and the impregnated fluorochemical is presently difficult, or perhaps impossible, to quantify because of the variables involved and because transparent silicone polymer is difficult to observe by optical microscopy. It can be theorized that perhaps the silicone polymer and the fluorochemical each tend to produce discontinuous films upon fiber surface, and that such films are discontinuous in a complementary manner. It may alternatively be theorized that perhaps the silicone polymer film is contiguous, or substantially so, relative to fluorochemical molecules on a fiber surface, and that the layer of silicone polymer on a fiber surface is so thin that any dislodgement of the fluorochemical may release the fluorochemical into the silicone polymer film thereby allowing the fluoroine to orient with the required cure temperature of the silicone, reactivating the water surface contact angle so that the water repellant properties of an underlying fluorochemical are exertable through the silicone polymer film. However, regardless of physical or chemical explanation, the combination of silicone polymer film and fluorochemical results in a fiber envelopment or cell or pore wall lining and the formation of an internal layer of silicone polymer in a web when this invention is practiced. After curing, the silicone polymer is permanently fixed material.

By using the impregnation method provided by this invention, one can achieve an impregnation of a silicone polymer composition into a porous substrate or web to obtain a desired treated web.

A curable silicone polymer such as used in the practice of this invention is applied under pressure using shear forces onto and into a web or substrate. The shear forces cause the curable silicone polymer to flow into the web. The extent of fiber envelopment and cell or pore wall lining is believed to be regulatable by controlling such factors as the selection and applied amount of fluorochemical and curable silicone polymer in combination with the applied compressive and shear forces employed at a given temperature so that fiber envelopment is achieved while the interstices and/or open cells of the web are not completely filled with such polymer in the region of the internal coating, and the outer opposed surfaces of the web are substantially completely free of silicone polymer coating or residue. After such an impregnation procedure, the curable silicone impregnant is then cured.

The curable silicone polymer impregnant is applied in an amount at least sufficient to partially saturate the web and fill some of the interstices or open cells of the web. Then, the web, while tensioned, is passed over and against shearing means or through a compression zone, such as between rollers or against a shear knife. Thus transversely applied shear force and compressive pressure is applied to the web. The combination of tensioning, shearing forces, and web traveling speed is sufficient to cause the curable silicone polymer impregnant to move into the web, out from the interstices or open cells around the web fibers, cells or pores being enveloped, thereby leaving at least some of the interstices and/or open cells unfilled in regions of the web outside of the region occupied by the interior coating, and preferably substantially free of, silicone polymer impregnant. Excess silicone polymer is removed by the surface wiping action of the shearing means. The curable silicone polymer impregnant enveloping the fibers is thereafter cured.

The desired impregnation or penetration of, and distribution of silicone polymer in, a web is believed to be achieved by localized pressuring forces exerted on a web surface which are sufficiently high to cause the viscosity of a silicone polymer impregnant composition to be locally reduced, thereby permitting such silicone impregnant to flow under such pressuring and to impregnate the web and to envelope its fibers or line the cell or pore walls thereof. To aid in this process, the web is preferably at least slightly distorted by tensioning or stretching, while being somewhat transversely compressed at the location of the impregnation. This distortion is believed to facilitate the entrance of the silicone polymer composition into the web. When the compression and tension are released, the silicone polymer composition is believed to be squeezed or compressed within and through the interstitial spaces, or open cell spaces, of the treated web.

If, for example, too much silicone polymer is present in the finished product, then either or both the tension and shear force can be increased, and vice versa for too little silicone polymer. If flow is not adequate upon the fibers, producing incomplete fiber envelopment, then the viscosity of the silicone impregnant composition can be reduced by reducing the pressures and temperatures employed for the impregnation. Alternatively, if the viscosity is excessive, then the impregnating pressure and/or temperature can be increased. Opposite adjustments should be made if silicone polymer impregnant flow is insufficiently viscous. If the silicone polymer impregnating composition is resistant to being positioned in a desired location in a desired amount in a given web at various viscosities and/or pressures, then the level of fluorochemical pretreatment of the web can be increased, as in the case of overimpregnation, or decreased, as in the case of underimpregnation.

In one embodiment of an impregnation procedure, the pressured impregnation of a web occurs between two rollers. One such roller bears a silicone polymer impregnant, typically and preferably distributed uniformly upon and over a circumferentially extending textured, or gravure surface. Such roller rotates (i) in the same direction as a facing roller and (ii) oppositely to the direction of movement of a continuously moving web traveling past the localized impregnation area achieved between such roller and such moving web. The unidirectional rotation of the two rollers is believed to produce a distorting and stretching force or effect upon the web. This force is believed to promote penetration of the silicone polymer impregnant into the web. This form of impregnant application or coating can be termed "reverse roll coating" for convenience. Preferably, the reverse coating rollers have generally horizontal axes while the moving web moves generally horizontally. The web is further concurrently both longitudinally tensioned and distorted by being stretched against metering bars, bar knives, and the like which are urged against the web.

Such an initial pressured impregnation step is preferably followed by a series of further pressured web treatment steps believed to accomplish impregnant reintroduction, impregnant distribution, impregnant scraping, and excess impregnant removal and recovery. The collective result of such steps gradually produces a web wherein the silicone polymer impregnant envelopes to a desired extent the fibers or lines the cell or pore walls comprising the web and collects within a desired internal region or zone in the web thereby filling or plugging interstitial spaces, or open cells or pores, of the web in such region, but not filling the internal structure of the treated web with silicone polymer beyond a desired extent. Particularly, and for example, in a fabric, a silicone polymer composition may be made to substantially completely envelope the fibers or line the cells or pores thereof and fill the interstitial spaces thereof in such internal region.

In another embodiment of an impregnation procedure, application of silicone polymer impregnant to a web occurs from a reservoir. This reservoir of silicone impregnant is positioned tightly against the tensioned, moving web (or fabric). The linearly extending, preferably vertically upwardly moving, web (or fabric), constitutes a wall portion of the reservoir. Next, along the path of web travel, a bar or shear knife is pressed strongly and transversely against and laterally across the longitudinally tensioned web (or fabric). Further along the path of web movement, a shear blade or flexible scraper knife is also strongly and transversely forced laterally across and against the tensioned web. More than one shear knife, or more than one flexible compressive knife, can be successively positioned along the path of web movement. These blade means are believed to reintroduce the silicone impregnant into the web, to distribute the silicone polymer, and to promote and complete the envelopment of fibers or lining of the cell or pore walls and fillage of interstices and open cells with silicone polymer, and form an internal coating in a desired region in a web. These scraper knives or shear blades are also believed to force the silicone polymer impregnant further into the three-dimensional structure of the web. Also, these knives, particularly the scraper knives, wipe or scrape excess silicone polymer impregnant off the surface of the web, thereby regulating the amount of silicone polymer impregnated.

The transversely applied shear forces applied across and against the web are sufficiently high to achieve temporarily and locally, a lowering of the viscosity of the preferably thixotropic viscous silicone polymer impregnant. The lowered viscosity silicone polymer impregnant is thus enabled to flow into, and upon, the internal three-dimensional structure of the web. Because the silicone polymer composition that is being applied is subject to cure with heat or radiation and time, and because the pressured impregnation is believed to produce localized heat, the shearing conditions used prior to curing are preferably controlled to minimize premature curing. The properties of the silicone polymer impregnant are preferably selected to be such that cure, or excessive cure, does not occur while the web is being treated with silicone polymer during the pressured impregnation. The cure preferably occurs only after the web impregnation procedure has been completed. Preferably, the cure temperature of the silicone polymer composition is relatively high (preferably above about 250° F.) and the heat exposure time is such as is needed to obtain a desired solid resilient elastomeric silicone polymer.

If desired, the rheology of the silicone polymer impregnant may be altered or controlled. Characteristics of a web are believed to be influenced by rheology, but it is believed that, in general, this invention can be practiced without careful control of rheology while controlling viscosity.

The viscosity of the silicone polymer impregnant is preferably lowered by the high pressure (shear) forces exerted during impregnation. However, such a pressure- and/or temperature-induced lowered viscosity should not go down too low, otherwise the impregnant can flow substantially uncontrolled in the web in the manner of a low viscosity liquid that is saturated and impregnated into a web as in prior art web treatments. If the viscosity of the silicone polymer composition is too low at the time of impregnation, then the web interstices or open cells can become excessively filled therewith, and the impregnant is not, for example, reliably and controllably applied to achieve an envelopment of the structural elements (including fibers) of the web being treated together with internal coating formation.

Benzophenones, and particularly 2,4-dihydroxybenzophenone, are believed to be a particularly useful class of additives to the starting silicone polymer composition, as hereinbelow described.

As above indicated, the activity transpiring at a final step in the practice of a method of this invention is generically referred to herein as curing. Conventional curing conditions known to the prior art for curing silicone polymer compositions are generally suitable for use in the practice of this invention. Thus, temperatures in the range of about 250° F. to about 350° F. are used and times in the range of about 30 seconds to about 1 minute can be used, although longer and shorter curing times and temperatures may be used, if desired, when thermal curing is practiced. Radiation curing, as with an electron beam or ultraviolet light can also be used. However, using platinum catalysts to accelerate the cure while using lower temperatures and shorter cure times is preferable.

Because either filled plugged or almost filled interstices or open cells in the region of an internal coating remain transmissive of air in cured webs of this invention, the webs are characteristically air permeable or breathable.

Sample webs or fabrics that are beneficially impregnated, fiber enveloped and internally coated in accordance with the invention are believed to include nylon, cotton, rayon and acrylic fabrics, as well as fabrics that are blends of fiber types. Sample nylon fabrics include lime ice, hot coral, raspberry pulp, and diva blue Tactel ® (registered trademark of ICI Americas, Inc.) fabrics available from agent Arthur Kahn, Inc. Sample cotton fabrics include Intrepid ® cotton cornsilk, sagebrush cotton, and light blue cotton fabrics available also from Arthur Kahn, Inc. Non-woven, mono-filamentous, fabrics such as TYVEK ® (registered trademark of E. I. dupont de Nemours Co., Inc.) and the like are also employable.

As indicated above, a web is preferably pretreated and impregnated with a fluorochemical prior to being impregnated under pressure with a silicone polymer composition as taught herein.

The fluorochemical impregnation is preferably accomplished by first saturating a web with a liquid composition which incorporates the fluorochemical, and then, thereafter, removing the excess liquid composition and residual carrier fluid by draining, compression, drying, or some combination thereof from the treated web.

It is now believed that any fluorochemical known in the art for use in web, particularly fabric treatment in order to achieve water repellency, soil repellency, grease repellency, or the like, can be used for purposes of practicing the present invention.

It is believed that a typical fluorochemical of the type used for web treatment can be characterized as a compound having one or more highly fluorinated portions, each portion being a fluoroaliphatic radical or the like, that is (or are) functionally associated with at least one generally non-fluorinated organic portion. Such organic portion can be part of a polymer, part of a reactive monomer, a moiety with a reactable site adapted to react with a binder, or the like.

Such a compound is typically applied to a fabric or other web as a suspension or solution in either aqueous or non-aqueous media. Such application may be conventionally carried out in combination with a non-fluorine or fluorine containing resin or binder material for the purpose of providing improved durability as regards such factors as laundering, dry cleaning, and the like.

Fluorochemicals are sometimes known in the art as durable water repellant (DWR) chemicals, although such materials are typically believed to be not particularly durable and to have a tendency to wash out from a fabric treated therewith. In contrast, fiber enveloped webs of this invention which have been pretreated with a fluorochemical display excellent durability and washability characteristics. Indeed, the combination of fluorochemical pretreatment and silicone polymer fiber envelopment such as provided by the present invention appears to provide synergistic property enhancement because the effects or properties obtained appear to be better than can be obtained than by using either the fluorochemical or the silicone polymer alone for web treatment.

Exemplary water repellant fluorochemical compositions include the compositions sold under the name Milease ® by ICI Americas Inc. with the type designations F-14N, F-34, F-31X, F-53. Those compositions with the "F" prefix indicate that they contain a fluorochemical as the principal active ingredient. More particularly, Milease ® F-14 fluorochemical, for example, is said to contain approximately 18 percent perfluoroacrylate copolymer, 10 percent ethylene glycol (CAS 107-21-1) and 7 percent acetone (CAS 67-64-1) dispersed and dissolved in 65 percent water. Milease ® F-31X is said to be a dispersion of a combination of fluorinated resin, acetone, and water.

Still another suitable class of water repellant chemicals is the Phobotex ® chemicals of Ciba/Geigy identified as Phototex ® FC104, FC461, FC731, FC208 and FC232 which are each believed to be suitable for use, typically in approximately a 5 percent concentration, in saturating a web for use in the invention. These and many other water repellent fluorochemicals are believed to be capable of creating a surface contact angle with water of greater than about 90 degrees when saturated into a web and to be suitable for use in the practice of this invention.

Another group of useful water repellent fluorochemicals is the TEFLON ®-based soil and stain repellents of E. I. dupont de Nemours & Co. Inc., 1007 Market Street, Wilmington, Del. 19898. Suitable TEFLON ® types for use in the practice of this invention include TEFLON ® G, NPA, SKF, UP, UPH, PPR, N, and MLV. The active water repellent chemical of each composition is believed to be a fluorochemical in polymeric form that is suitable for dispersion in water, particularly in combination with a cationic surfactant as a dispersant. These dispersions are dilutable in all proportions with water at room temperature. One preferred class of fluorochemical treating compositions useful in the practice of this invention comprises about 1 to about 10 weight percent, more preferably about 5 weight percent of one of the above indicated TEFLON ®-type water repellent fluorochemcials in water.

Another major group of suitable water repellent fluorochemical compositions useful in the practice of the invention is commercially available under the designation ZEPEL ® rain and stain repellent chemicals of E. I. dupont de Nemours & Co. Inc., such as ZEPEL ® water repellent chemicals types B, D, K, RN, RC, OR, HT, 6700 and 7040. Each is believed to be a fluorochemical in polymeric form that is disperible in all proportions at room temperature. The dispersants ZEPEL ® B, D, K, and RN are believed to be cationic, while the dispersant ZEPEL ® RC is believed to be non-ionic.

As an exemplary composition, ZEPEL ® 6700 is said to be comprised of 15 to 20 percent perfluoroalklyl acrylic copolymer, 1 to 2 percent alkoxylated carboxylic acid, and 3 to 5 percent ethylene glycol. Exemplary characteristics of the composition include a boiling point of 100° C. at 760 mm Hg and a specific gravity of 1.08. The volatiles are approximately 80 percent by weight. The pH is 2 to 5. The odor is mild; the concentrate form is that of a semi-opaque liquid; and the concentrate color is straw white. The composition and characteristics of ZEPEL ® 7040 repellent chemical are believed to be substantially identical to those of ZEPEL ® 6700 except that the former composition additionally contains 7 to 8 percent acetone.

Another major group of water repellent fluorochemicals comprises the Scotchgard ® water repellent chemicals of 3M Co., St. Paul, Minn. The Scotchgard ® fluorochemicals are believed to be aqueously dispersed fluorochemicals in polymeric form. The compositions of two suitable Scotchgard ® water repellent fluorochemicals are believed to be disclosed in U.S. Pat. Nos. 3,393,186 and 3,356,628, which patents are incorporated herein by reference. Thus, the Scotchgard ® fluorochemical of U.S. Pat. No. 3,356,628 consists of copolymers of perfluoroacrylates and hydroxyalkyl acrylates. These copolymers are suitable for use as an oil and water repellent coating on a fibrous or porous surface. They have a carbon to carbon main chain and contain recurring monovalent perfluorocarbon groups having from 4 to 18 carbon atoms each and also having recurring hydroxyl radicals. From 20 to 70 percent of the weight of such copolymer is contributed by fluorine atoms in the perfluorocarbon groups and from 0.05 to 2 percent of the weight of the copolymer is contributed by the hydroxyl radicals. Such copolymer is said to have improved surface adherability properties as compared to the homopolymer of a corresponding fluorocarbon monomer.

The Scotchgard ® fluorochemical of U.S. Pat. No. 3,393,186 consists of perfluoroalkenylacrylates and polymers thereof. An exemplary fluorinated monomer has the formula:

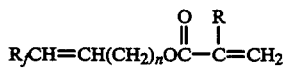

wherein $R_f$ is a fluorocarbon group having from 3 to 18 carbon atoms, R is hydrogen or methyl, and n is 0–16. Such a water repellent fluorochemical composition is supplied and saturated into the substrate web as a readily pourable aqueous dispersion.

U.S. Pat. No. 4,426,476 discloses a fluorochemical textile treating composition containing a water-insoluble fluoroaliphatic radical, an aliphatic chlorine-containing ester and a water insoluble, fluoroaliphatic radical containing polymer.

U.S. Pat. No. 3,896,251 discloses a fluorochemical textile treating composition containing a fluoroaliphatic radical containing linear vinyl polymer having 10 to 60 weight percent fluorine and a solvent soluble carbodiimide preferably comprising fluoroaliphatic groups. A table in this patent lists a plurality of prior art fluoroaliphatic radical containing polymers useful for the treatment of fabrics and the prior art patents where such polymers are taught.

U.S. Pat. No. 3,328,661 discloses textile treating solutions of a copolymer of an ethylenically unsaturated fluorocarbon monomer and a ethylenically unsaturated epoxy group containing monomer.

U.S. Pat. No. 3,398,182 discloses fluorocarbon compounds useful for fabric treatment that contain a highly fluorinated oleophobic and hydrophobic terminal portion and a different non-fluorinated oleophilic portion linked together by a urethane radical.

Water repellent fluorochemical compositions are preferably utilized to saturate a starting untreated porous web substrate so that such composition and its constituents wet substantially completely and substantially uniformly all portions of the web. Such a saturation can be accomplished by various well known techniques, such as dipping the web into a bath of the composition, or padding the composition onto and into the web, or the like. Padding is the presently preferred method of fluorochemical application.

After application of the fluorochemical composition to the web, the water (or liquid carier) and other volatile components of the composition are removed by conventional techniques to provide a treated web that contains the impregnated fluorochemical throughout the web substrate.

In a preferred procedure of fluorochemical impregnation, a web is substantially completely saturated with an aqueous dispersion of a fluorochemical. Thereafter, the resulting impregnated web is compressed to remove excess portions of said dispersion. Finally, the web is heated to evaporate the carrier liquid. If the fluorochemical is curable, then the heating also accomplishes curing.

After the fluorochemical treatment, the fluorochemical is found only on or in the web structural elements or fibers and is substantially completely absent from the web interstices.

The fluorochemical concentration in the treating composition is such as to permit a treated fluorochemical containing web, after volatiles of the treating composition are removed, to exhibit a contact angle with water applied to an outer web surface which is greater than about 90°. More preferably, the contact angle provided is greater than about 130°.

The web weight add-on provided by the fluorochemical after removal of volatiles is usually relatively minor. However, the weight add on can vary with such factors as the nature of web treated, the type of silicone impregnant utilized in the next step of the process, the temperature at which the impregnant is applied, the ultimate use contemplated for a web, and the like.

Typical weight add-ons of fluorochemical are in the range of about 1 to about 10 percent of the original weight of the web. More preferably, such weight add-ons are about 2 to about 4 weight percent of the weight of the starting fabric.

Durability of a web that has been treated with a fluorochemical and durability of a web that is subsequently treated with a silicone polymer can sometimes be improved by the conventional process of "sintering". The exact physical and chemical processes that occur during sintering are unknown. The so-called sintering temperature utilized is a function of the fluorochemical composition utilized and such temperature is frequently recommended by fluorochemical manufacturers. Typically, sintering is carried out at a temperature of about 130° to about 160° C. for a period of time of about 2 to about 5 minutes. Acid catalysts can be added to give improved durability to laundering and dry cleaning solvents.

The fluorochemical is believed to provide more than water or other repellent properties to the resulting treated (impregnated) web, particularly since the curable silicone impregnant is often itself a water repellent.

Rather, and without wishing to be bound by theory, it is believed that the fluorochemical in a treated web provides relative lubricity for the treated fibers during the pressure application of the curable silicone polymer impregnant. The silicone polymer impregnant is applied under pressures which can be relatively high, and this impregnant is itself relatively viscous, as is discussed herein. In order for the curable silicone polymer impregnant to coat and envelope web fibers, but not fill web interstitial voids, the fibers of the web may move over and against each other to a limited extent, thereby to permit entry of the silicone impregnant into and around the fibers. It is thought that the fluorochemical deposits may facilitate such fiber motion and facilitate envelopment during the pressure impregnation and subsequent shearing processing.

Alternatively, the fluorochemical may inhibit deposition of the silicone polymer impregnant at the positions of the fluorochemical deposits which somehow ultimately tends to cause thin enveloping layers of silicone polymer to form on fibers.

The precise physics and chemistry of the interaction between the fluorochemical and the silicone impregnant is not understood. A simple experiment demonstrates movement of the liquid silicone polymer as influenced by the presence of the fluorochemical:

A piece of fabric, for example the Red Kap Milliken poplin polyester cotton blend fabric, is cut into swatches. One swatch is treated with an adjuvant, for example a three percent solution of the durable water-repellent chemical Milease ® F-31X. The treated swatch and an untreated swatch are each positioned at a 45° angle to plumb. A measured amount, for example one-half ounce, of a viscous polymer composition, for example the Mobay ® 2530A/B silicon composition, is dropped onto the inclined surface of each swatch. The distance in centimeters that the composition flows downwards upon the surface of the swatch is measured over time, typically for 30 minutes.

A graphical plot of the flow of the silicone composition respectively upon the untreated and treated swatches over time can be prepared, such as shown in FIG. 1. At the expiration of 30 minutes the viscous composition has typically traveled a distance of about 8.8 centimeters upon the treated swatch, or a rate of about 0.29 centimeters per minute. At the expiration of the same 30 minutes, the viscous composition has typically traveled a lesser distance of about 7.1 centimeters upon the untreated swatch, or a rate of about 0.24 centimeters per minute. Qualitatively commensurate results are obtainable with other DWR fluorochemical adjuvants that facilitate the viscous flow of polymer compositions in accordance with the invention. Indeed, if desired, the simple flow rate test can be used to qualify an adjuvant compound for its employment within the method of the invention. The fluorochemical pretreated web generally increases the surface contact angle of the silicone polymer while reducing the amount of saturation of the silicone polymer into the fibers themselves.

The fluorochemical treated web is thereafter impregnated under pressure with a predetermined amount of a curable silicone polymer impregnant composition to form a web whose fibers are preferably substantially completely enveloped with such curable impregnant and whose outer surfaces and interstices are preferably substantially completely free of the curable impregnant. The silicone polymer impregnant is thereafter cured by heat, radiation, or the like. Even room temperature curing can be used. A silicone polymer impregnated, fluorochemical pretreated web can be interveningly stored before being subjected to curing conditions depending upon the so-called pot life of the treating silicone polymer impregnant.

A curable silicone polymer impregnant composition utilized in the practice of this invention preferably has a viscosity that is sufficient to achieve an internal coating of the web. Generally, the viscosity is greater than about 1000 centipoise and less than about 2,000,000 centipoise at a shear rate of 10 reciprocal seconds. It is presently most preferred that such composition have a viscosity in the range of about 5,000 to about 1,000,000 centipoise at 25° C. Such a composition is believed to contain less than about 1% by weight of volatile material.

The silicone polymer is believed to be typically polymeric and to be commonly a mixture of co-curable polymers, oligomers, and/or monomers. A catalyst is usually also present, and, for the presently preferred silicone polymer compositions discussed hereinafter, is platinum or a platinum compound, such as a platinum salt.

A preferred class of liquid curable silicone polymer compositions comprises a curable mixture of the following components:

(A) at least one organo-hydrosilane polymer (including copolymers);
(B) at least one vinyl substituted polysiloxane (including copolymers);
(C) a platinum or platinum containing catalyst; and
(D) (optionally) fillers and additives.

Typical silicone hydrides (component A) are polymethylhydrosiloxanes which are dimethyl siloxane copolymers. Typical vinyl terminated siloxanes are vinyldimethyl terminated or vinyl substituted polydimethylsiloxanes. Typical catalyst systems include solutions or complexes of chloroplatinic acid in alcohols, ethers, divinylsiloxanes, and cyclic vinyl siloxanes.

The polymethylhydrosiloxanes (component A) are used in the form of their dimethyl copolymers because their reactivity is more controllable than that of the homopolymers and because they result in tougher polymers with a lower cross-link density. Although the reaction with vinyl functional silicones (component B) does reportedly take place in 1:1 stoichiometry, the minimum ratio of hydride (component A) to vinyl (component B) in commercial products is reportedly about 2:1 and may be as high as 6:1. While the hydrosilation reaction of polymethylhydrosilane is used in both so called RTV (room temperature vulcanizable) and LTV (low temperature vulcanizable) systems, and while both such systems are believed to be useful in the practice of the present invention, systems which undergo curing at elevated temperature are presently preferred.

Elastomers produced from such a curing reaction are known to demonstrate toughness, tensile strength, and dimensional stability.

Particulate fillers are known to be useful additives for incorporation into liquid silicone polymer compositions. Such fillers apparently not only can extend and reinforce the cured compositions produced therefrom, but also can favorably influence thixotropic behavior in such compositions. Thixotropic behavior is presently preferred in compositions used in the practice of this invention. A terminal silanol (Si—OH) group makes such silanol siloxanes susceptible to reaction in curing, as is believed desirable.

It is believed that all or a part of component B can be replaced with a so called silanol vinyl terminated polysiloxane while using an organotin compound as a suitable curing catalyst as is disclosed in U.S. Pat. No. 4,162,356. However, it is presently preferred to use vinyl substituted polysiloxanes in component B.

An impregnate composition useful in this invention can contain curable silicone resin, curable polyurethane, curable fluorosilicone, curable modified polyurethane silicones, curable modified silicone polyurethanes, curable acrylics, polytetrafluoroethylene, and the like.

One particular type of silicone impregnant composition which is believed to be well suited for use in the impregnation step of the method of the invention is taught in U.S. Pat. Nos. 4,472,470 and 4,500,584 and in U.S. Pat. No. 4,666,765. The contents of these patents are incorporated herein by reference. Such a composition comprises in combination:

(i) a liquid vinyl chainterminated polysiloxane having the formula,

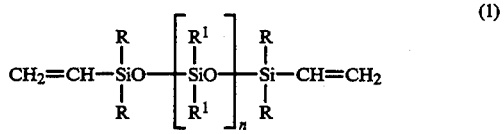

(1)

wherein R and $R^1$ are monovalent hydrocarbon radicals free of aliphatic unsaturation with at least 50 mole percent of the $R^1$ groups being methyl, and where n has a value sufficient to provide a viscosity of about 500 centipoise to about 2,000,000 centipoise at 25° C.;

(ii) a resinous organopolysiloxane copolymer comprising:
  (i) $(R^2)_3SiO_{0.5}$ units and $SiO_2$ units, or
  (ii) $(R^3)_2SiO_{0.5}$ units, $(R^3)_2SiO$ units and $SiO_2$ units, or
  (iii) mixtures thereof, where $R^2$ and $R^3$ are selected from the group consisting of vinyl radicals and monovalent hydrocarbon radicals free of aliphatic unsaturation, where from about 1.5 to about 10 mole percent of the silicon atoms contain silicon-bonded vinyl groups, where the ratio of monofunctional units to tetrafunctional units is from about 0.5:1 to about 1:1, and the ratios of difunctional units to tetrafunctional units ranges up to about 0.1:1;

(iii) a platinum or platinum containing catalyst; and (iv) a liquid organohydrogenpolysiloxane having the formula:

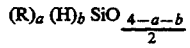

in an amount sufficient to provide from about 0.5 to about 1.0 silicon-bonded hydrogen atoms per silicon-bonded vinyl group of above component (i) or above subcomponent (iii) of, $R_a$ is a monovalent hydrocarbon radical free of aliphatic unsaturation, a has a value of from about 1.0 to about 2.1, b has a value of from about 0.1 to about 1.0, and the sum of a and b is from about 2.0 to about 2.7, there being at least two silicon-bonded hydrogen atoms per molecule.

Optionally, such a composition can contain a finely divided inorganic filler (identified herein for convenience as component (v)).

For example, such a composition can comprise on a parts by weight basis:
(a) 100 parts of above component (i);
(b) 100–200 parts of above component (ii);
(c) a catalytically effective amount of above component (iii), which, for present illustration purposes, can range from about 0.01 to about 3 parts of component (iii), although larger and smaller amounts can be employed without departing from operability (composition curability) as those skilled in the art will appreciate;
(d) 50–100 parts of above component (iv), although larger and smaller amounts can be employed without departing from operability (curability) as those skilled in the art will appreciate; and
(e) 0–50 parts of above component (v).

Embodiments of such starting composition are believed to be available commercially from various manufacturers under various trademarks and trade names.

As commercially available, such a composition is commonly in the two-package form (which are combined before use). Typically, the component (iv) above is maintained apart from the components (i) and (ii) to prevent possible gelation in storage before use, as those skilled in the art appreciate. For example, one package can comprise components (i) and (ii) which can be formulated together with at least some of component (ii) being dissolved in the component (i), along with component (iii) and some or all of component (v) (if employed), while the second package can comprise component (iv) and optionally a portion of component (v) (if employed). By adjusting the amount of component (i) and filler component (v) (if used) in the second package, the quantity of catalyst component (iii) required to produce a desired curable composition is achieved. Preferably, component (iii) and the component (iv) are not included together in the same package. As is taught, for example, in U.S. Pat. No. 3,436,366 (which is incorporated herein by reference), the distribution of the components between the two packages is preferably such that from about 0.1 to 1 part by weight of the second package is employed per part of the first package. For use, the two packages are merely mixed together in suitable fashion at the point of use.

Other suitable silicone polymer compositions are disclosed in the following U.S. patents:

U.S. Pat. No. 4,032,502 provide compositions containing a linear polydiorganosiloxane having two siloxane bonded vinyl groups per molecule, organosiloxane that is soluble in such linear polydiorganosiloxane and comprised of a mixture of a polyorganosiloxane and a polydiorganosiloxane, platinum-containing catalyst, a platinum catalyst inhibitor, and a reinforcing silica filler whose surface has been treated with an organosilicone compound.

U.S. Pat. No. 4,108,825 discloses a composition comprising a triorganosiloxy end-blocked polydiorganosiloxane, an organohydrogensiloxane having an average of at least 2.1 silcon-bonded hydrogen atoms per molecule, a reinforcing silica filler having a surface treated with an organosilicone compound, a platinum catalyst, and ceric hydrate. Such silicone polymer composition is desirable when a web is being prepared which has flame retardant properties.

U.S. Pat. No. 4,162,243 discloses a silicone composition of 100 parts by weight triorganosiloxy endblocked polydimethylsiloxane, reinforcing amorphous silica that is surface treated with organosiloxane groups, organohydrogensiloxane, and platinum catalyst.

U.S. Pat. No. 4,250,075 discloses a liquid silicone polymer composition that comprises vinyldiorganosiloxy endblocked polydiorganosiloxane, polyorganohydrogensiloxane, platinum catalyst, platinum catalyst inhibitor, and carbonaceous particles. Such a silicone polymer composition is useful when a web of this invention is being prepared that has electrically conductive properties.

U.S. Pat. No. 4,427,801 discloses a curable organopolysiloxane of liquid triorganosiloxy endblocked polydiorganosiloxane wherein the triorganosiloxy groups are vinyl dimethylsiloxy or vinylmethylphenylsiloxy, finely divided amorphous silica particles treated with mixed trimethylsiloxy groups and vinyl-containing siloxy groups, organopolysiloxane resin containing vinyl groups, organohydrogensiloxane, and a platinum containing catalyst.

U.S. Pat. No. 4,500,659 discloses a silicone composition of liquid triorganosiloxy endblocked polydimethylsiloxane wherein the triorganosiloxy units are dimethylvinylsiloxy or methylphenylvinylsiloxy, a reinforcing filler whose surface has been treated with a liquid hydroxyl end-blocked polyorganosiloxane which is fluorine-substituted, a liquid methylhydrogensiloxane, and a platinum-containing catalyst.

U.S. Pat. No. 4,585,830 disccloses an organosiloxane composition of a triorganosiloxy-endblocked polydiorganosiloxane containing at least two vinyl radicals per molecule, an organohydrogensiloxane containing at least two silicone-bonded hydrogen atoms per molecule, a platinum-containing hydrosilation catalyst, optionally a catalyst inhibitor, a finely divided silica filler, and a silica treating agent which is at least partially immiscible with said polydiorganosiloxane.

U.S. Pat. No. 4,753,978 discloses an organosiloxane composition of a first diorganovinylsiloxy terminated polydiorganosiloxane exhibiting a specified viscosity and having no ethylenically unsaturated hydrocrabon radicals bonded to non-terminal silicon atoms, a second diorganovinylsiloxy terminated polydiorganosiloxane that is miscible with the first polydiorganosiloxane and contains a vinyl radical, an organohydrogensiloxane, a platinum hydrosilation catalyst, and a treated reinforcing silica filler.

U.S. Pat. No. 4,785,047 discloses silicone elastomers having a mixture of a liquid polydiorganosiloxane containing at least two vinyl or other ethylenically unsaturated radicals per molecule and a finely divided silica filler treated with a hexaorganodisilazane which mixture is then compounded with additional hexaorganodisiloxane.

U.S. Pat. No. 4,329,274 discloses viscous liquid silicone polymer compositions that are believed to be suitable and which are comprised of vinyl containing diorganopolysiloxane (corresponding to component B), silicon hydride siloxane (corresponding to component A) and an effective amount of a catalyst which is a halogenated tetrameric platinum complex.

U.S. Pat. No. 4,442,060 discloses a mixture of 100 parts by weight of a viscous diorganopolysiloxane oil, 10 to 75 parts by weight of finely divided reinforcing silica, 1 to 20 parts by weight of a structuring inhibitor, and 0.1 to 4 parts by weight of 2,4-dichlorobenzoyl peroxide cross-linking agent.

Silicone resin compositions shown in Table I below have all been used in the practice of this invention. Such compositions of Table I are believed to involve formulations that are of the type hereinabove characterized.

TABLE I

Illustrative Starting Silicone Polymer Compositions

| Manufacturer | Trade Designation | Components[1] |
|---|---|---|
| Mobay | Silopren ® LSR 2530 | Vinyl-terminated polydimethyl/siloxane with fumed silica, methylhydrogen polysiloxane |
| Mobay | Silopren ® LSR 2540/01 | |
| Dow Corning | Silastic ® 595 LSR | polysiloxane |
| General Electric | SLE 5100 | polysiloxane |
| General Electric | SLE 5106 | siloxane resin solution |
| General Electric | SLE 5300 | polysiloxane |
| General Electric | SLE 5500 | polysiloxane |
| Shin-Etsu | KE 1917 | |
| Shin-Etsu | DI 1940-30 | |
| SWS Silicones Corporation | Liquid Rubber BC-10 | silicone fluid with silicone dioxide filler and curing agents |

Table I footnote:
[1]Identified components do not represent complete composition of the individual products shown.

When a polymer composition of a silicone polymer and a benzophenone is impregnated into a porous web as taught herein, protection of an organic web against ultraviolet radiation is improved, and the degradation effects associated with ultraviolet light exposure are inhibited, as may be expected from prior art teachings concerning the behavior of benzophenones.

Surprisingly and unexpectedly, however, when silicone polymer compositions such as used in this invention contain a benzophenone, the resulting composition is believed to display improved viscosity characteristics, particularly thixotropic characteristics, and also curing acceleration, when such a composition is subjected to high shear forces.

The normal (ambient conditions or rest) viscosity and rheology characteristics of a composition useful in the present invention are lowered by high pressure (shear) forces applied thereto, such as the shear forces that occur during pressured impregnation. However, this pressure- and temperature-induced lower viscosity does not reach inoperative harmful levels, such as hereinabove discussed.

A presently preferred benzophenone additive useful in the present invention is 2,4-dihydroxygenzophenone.

The regulation of internal and external rheology, and of viscosity, achieved in a characteristically highly viscous polymer composition of the invention is believed to be an important and desirable feature of the benzophenone and silicone polymer compositions which find use in internally coated web manufacture as taught herein.

In such compositions useful in the present invention, a control of compositional rheology, and particularly of complex viscosity, is accomplishable, if desired, by the selective addition of diluent and additives. These polymer compositions characteristically exhibit performance curves indicating substantially level and constant loss modulus, storage modulus, and complex viscosity over extended temperature ranges. The graphic plots of loss modulus, storage modulus, and complex viscosity versus temperature all are believed to characteristically exhibit a sharp knee that shows the moduli to increase in value rapidly at cure temperatures.

Preferably, the curing proceeds to a point where the silicone polymer composition is no longer sticky, or tacky, but preferably curing is not allowed to continue to a point where the resulting polymer composition becomes excessively hard, rigid, or brittle. Compositions of this invention are controllably curable into polymeric materials which are preferably not sticky or tacky, and which have desirable elastomeric, flexural, and resiliency characteristics.

To prepare a silicone polymer composition which incorporates a benzophenone, one preferably admixes the benzophenone with the silicone polymer composition at the time of use. The benzophenone component can be regarded as, or identified herein for convenience as, component (vi). On the same parts by weight basis above used, a composition of this invention preferably contains from about 0.3 to about 10 parts of such component (vi), although larger and smaller amounts can be used, if desired, without departing from the spirit and scope of the invention.

One class of derivitized benzophenones useful in the practice of this invention is characterized by the generic formula:

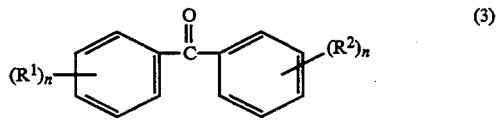

where:
R$^1$ and R$^2$ are each selected from the group consisting of hydroxyl, lower alkoxy, and hydrogen, and n and m are each an integer of 1 or 2

Examples of substituted benzophenones of formula (3) include

TABLE II
Substituted Benzophenones

| ID No. | (Name) | (Commercially available under specified trademark from BASF) |
|---|---|---|
| 1 | 2,4-dihydroxybenzophenone | "Uvinul" 400[1] |
| 2 | 2-hydroxy-4-methoxy-benzophenone | "Uvinul" M-40 |
| 3 | 2,2',4,4'-tetrahydroxybenzophenone | "Uvinul" D-50 |
| 4 | 2,2'-dihydroxy-4,4'-dimethoxybenzophenone | "Uvinul" D-49 |
| 5 | mixed tetra-substituted benzophenones | "Uvinul" 49D |

Table II footnote:
[1]Presently most desired substituted benzophenone

Another class of derivitized benzophenones useful in the practice of this invention is characterized by the generic formula:

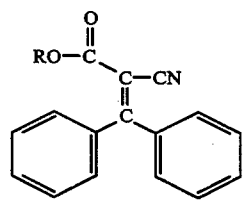

where:
R$^3$ is a lower alkyl radical.

An example of a substituted benzophenone of formula (4) is: 2-ethylhexyl-2-cyano-3,3-diphenylacrylate (available from BASF under the trademark "Uvinul N-539").

In the preceding formulas (3) and (4), the term "lower" has reference to a radical containing less than about 8 carbon atoms.

The contact angle exhibited by a silicone impregnant composition of this invention varies with the particular web which is to be saturated therewith. However, the contact angle of water is generally lower for the non-impregnated side than the impregnated side. The combination of the processed web, the silicone polymer and the fluorochemical generally produces higher water contact angles than webs treated only with fluorochemicals. The performance of an impregnant composition may be determined by the nature of a previously applied saturant such as a fluorochemical. Suitable starting compositions include 100% liquid curable silicone rubber compositions, such as SLE5600 A/B from General Electric, Mobay LSR 2580A/B, Dow Corning Silastic ® 595 LSR and Silastic ® 590 which when formulated with substituted benzophenone as taught herein will form a contact angle of much greater than 70 degrees, and typically of 90+ degrees, with typical porous webs (such as fabrics) that have a residue of fluorochemical upon (and within) the web from a prior saturation.

The silicone polymer composition of this invention can also carry additives into the three-dimensional structure of the web during the pressured impregnation. Further, it is preferable, that any additives be bound into the cured composition permanently as located in the three-dimensional structure of the web. Particularly in the case of fabrics, this desirably positions the additives mainly on surface portions of the treated yarns and fibers in positions where they typically are beneficially located and maintained.

Control of the pressurized impregnation step can be provided at a number of areas since the impregnation is sensitive to the viscosity of the impregnant both at atmospheric pressure and at superatmospheric pressure. The ambient temperature affecting the impregnant as it is applied, and the pressure-induced temperature changes occurring during application of the impregnant also play roles in viscosity and therefore the shear process. Of course, the chemical composition of the silicone polymer impregnant composition of this invention also plays a role in the shear process and assists in the formation of an internal coating.

The amount of silicone polymer impregnant utilized and the weight add-on thereof are again variable and dependent upon several things such as the treated web, the desired end use of the web, cost and the like. Web weight add-ons can be as little as about 5 weight percent up to about 200 weight percent of the untreated web. For producing breathable, water-repellant fabric webs of this invention, weight add-ons are preferably in the range of about 10 to about 100 weight percent of the weight of the untreated web.

The fluorochemical saturant composition may also contain a bonding agent. The bonding agent can facilitate the bonding of the water repellant chemical and/or the impregnate to the three-dimensional structure of the web within which it is saturated. Mobay Silopren® bonding agent type LSR Z 3042 and Norsil TM 815 primer are representative compositions that can be used to facilitate bonding of the water repellant chemicals and/or impregnant to and within the web. Use of the bonding agents is not essential to the practice of this invention, but may improve bonding of the fluorochemical and/or the silicone polymer composition to fibers.

The fluorochemical particularly, and also the bonding agents when used, are preferably affixed to the three-dimensional structure of the web prior to a subsequent pressured impregnation. Complete affixing is not necessary for the fluorochemical. The fluorochemical will apparently facilitate the pressured impregnation of a silicone polymer composition even if the fluorochemical is not preliminarily fixed within or located within the web being treated. However, fixing, especially by sintering, appears to cause the water repellant chemicals to flow and to become better attached to the three-dimensional structure of the web. In this regard, a lesser amount of fluorochemical will remain in place better, and will better facilitate the subsequent pressure impregnation of the silicone polymer, if the sintering or insolubilizing step is performed prior to such a pressured impregnation.

After fluorochemical saturation followed by silicone polymer impregnation and curing, a web may have a surface contact angle of greater than about 70 degrees, and more typically greater than about 90 degrees. Web impregnation pressures can involve transverse force or pressure in the range of tens to hundreds of pounds per square inch of web surface.

Similar to the functional qualifications achieved by the use of a fluorochemical in the preferred saturating pretreatment step, the silicone impregnant introduced by the pressured impregnation step can be defined by its functional qualifications. For example, the silicone impregnant produces a contact angle with a fluorochemical treated web of greater than about 70 degrees. In measuring the liquid contact angle with a fluorochemical trated surface and a silicone treated surface, it will be understood that such a contact angle cannot exceed 180 degrees. The contact angle of a fluorochemical will be within a range of about 90 degrees to about 180 degrees while the contact angle of the silicone polymer will be within a range of about 70 degrees to about 180 degrees.

The contact angle exhibited by the silicone impregnant can be, if desired, qualified against the particular web saturated with the particular fluorochemical saturant. The selection of a suitable silicone polymer composition may be determined by the nature of the previously applied fluorochemical saturant. The fluorochemical saturant and silicone polymer compositions are, however, not critical to the practice of this invention since wide respective compositional ranges may be involved. In particular, a substantially undiluted liquid silicon rubber which is available from suppliers, such as GE, Dow Corning, and Mobay-Bayer, will characteristically form a contact angle of much greater than about 70 degrees, and typically greater than about 90 degrees, with typical porous webs (such as fabrics) that have a residue of fluorochemical upon (and within) the web resulting from a prior saturation.

The silicone polymer composition can carry additives into the three-dimensional structure of the web in the pressured impregnation step of the method of the invention. Further, the silicone polymer composition, when cured, is capable of adhering to structural elements, fibers, yarns, and the like, and any additives dispersed therein. Thus, additives are positioned adjacent to or on surfaces of structural elements, yarns, fibers and the like, in a position where they can be beneficial.

Examples of additives that are dispersible in effective amounts in a viscous silicone polymer composition typically at a concentration of about 0.1 to 20 weight percent (based on total composition weight) include ultraviolet absorbers, flame retardants, aluminum hydroxide, filling agents, blood repellents, flattening agents, optical reflective agents, hand altering agents, biocompatible proteins, hydrolyzed silk, and the like. Hydrolyzed silk is a texturing agent that imparts a substantially silky feel to a fabric treated in accordance with the method of the invention regardless of whether or not such treated web or fabric is itself silk.

Examples of other silicone polymer dispersible agents include those affecting thermal conductivity, radiation reflectivity, electrical conductivity, and other properties. For example, if a metallic sheen and/or thermal or electrical conductivity or infrared background blending is desired, powdered metals may be dispersed therein.

The impregnation is sensitive to the viscosity of the silicone polymer composition. The impregnation temperature affects the silicone polymer composition by reducing or altering its viscosity. Shear-induced temperature changes occurring during application or during subsequent shear processing of the silicone polymer can affect viscosity. The chemical composition of the silicone polymer also plays a role in the treating process and can assist in the treatment of web structural elements (including fibers) and the regulation of the filling of interstices and open cell voids.

Various machines and procedures can be used for performing the process of the invention. Illustrative machines and processes of use are now described which are suitable for use in the practice of this invention.

Figure 4A:
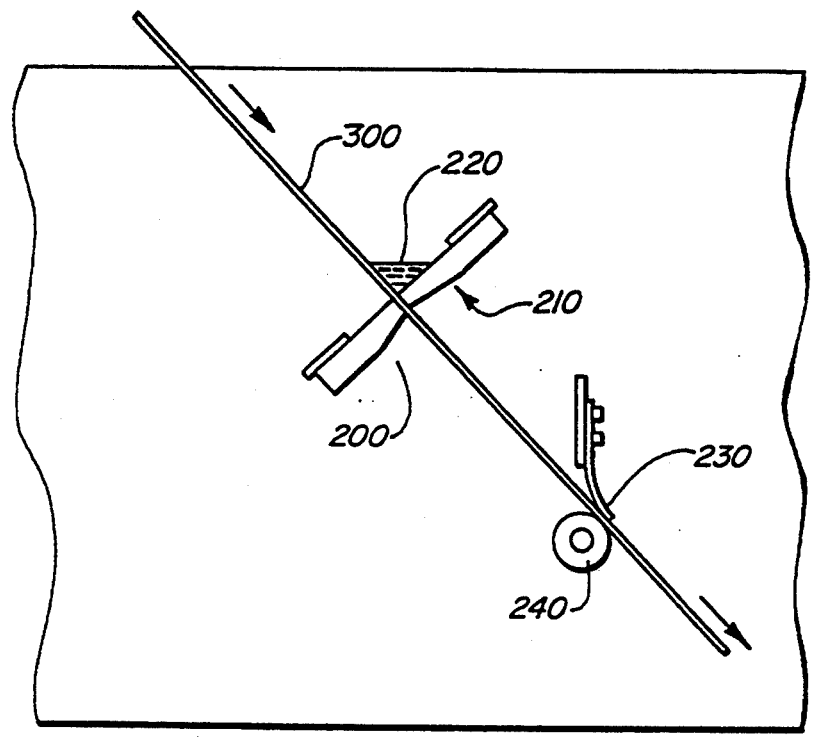
FIGS. 4a and 4b illustrate diagrammatically one embodiment of an apparatus suitable for use in the practice of the present invention.
Figure 4B:
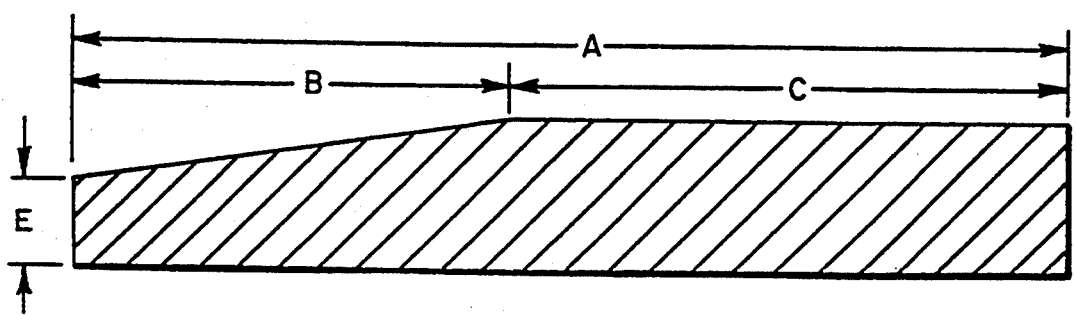

An embodiment of a machine suitable for accomplishing pressured impregnation in accordance with this invention is illustrated in side elevational view in FIG. 4a. Two blades 200 and 210 in opposed relationship to one another are provided in functional combination with means for providing a precisely adjustable gap therebetween through which a web or fabric 300 is drawn while having a silicone polymer composition 220 applied to either one or both surfaces thereof. An enlarged side view of a typical blade 200 or 210 is shown in FIG. 4b. Dimensions A, B, C, D, and E are typically and exemplarily illustrated as, respectively, about 3½ inches, about 1½ inches, about 2 inches, about ½ inch, and about 5/16 inch. The narrow edge is preferably milled to a tolerance of about 1/10,000 inch continuously along the edge surface of each blade which is typically and illustratively about 38 inches long. Each of the corners of the narrow edge is preferably and illustratively a hard (not beveled or ground) angular edge. Each blade 200 or 210 is typically and illustratively made from carbon steel or stainless steel. A reservoir of silicone polymer composition is formed preferably on one upper surface of the fabric 300 behind (relative to the direction of fabric movement) an upper one of the blades 200 and 210 which are mounted on a frame (not shown) so as to extend horizontally. As the fabric 300 is drawn through the slit orifice defined between blades 200 and 210, some impregnant becomes entrained on the web or fabric surface and moves through such slit orifice, thereby accomplishing pressurized impregnation of web or fabric 300. The slit orifice gap is chosen preferably and illustratively to be slightly smaller than the relaxed thickness of the starting web or fabric.

Referring to FIG. 4a, a second pressured impregnation station is seen to be positioned downstream (relative to the direction of fabric movement) from the pair of opposed blades 200 and 210. At this station, a knife blade 230 is provided which has an edge that presses against the web or fabric 300 to reintroduce the silicone polymer composition into the fabric 300. One side of blade 230 adjacent the edge thereof is strongly biased against an adjacent cylinder or bar 240, which, in the embodiment shown, does not rotate. If desired, bar 240 can be journaled for rotational movement. As the fabric is moved between the blade 230 and the bar 240, it is preferably uniformly compressed. Preferably, the compression force is in the range of about 10 to about 500 inch pounds, although higher and lower forces can be employed. As the fabric 300 passes over the edge of blade 230, it is drawn away at an angle from the blade edge under longitudinal tension. For example, longitudinal tension in the range of from about 0.5 to 10 pounds per inch can be employed. Such pressured impregnation serves to distribute and reintroduce the polymer composition in the web. Excess polymer composition is removed by blade scraping. Passage of the fabric 300 between the blade 230 and the bar 240 and over the edge of the blade 230 is believed to produce shear forces in the impregnant 220 (within the fabric 300) that facilitate flow and distribution thereof within the three-dimensional matrix of the fabric 300. Concurrently, blade 230 also scrapes excess silicone polymer composition impregnant off the fabric's surface in contact with the edge of blade 230.

Both the steps of fluorochemical saturation and of subsequent silicone polymer composition impregnation are performable, if desired, in production volumes, and at speeds which can be typical of the so called high end range of fabric finishing lines. The fluorochemical saturation is conveniently accomplished conventionally by using a padbath in which the fabric is run through a dilute treating bath followed by squeeze rollers to remove excess liquid and overdrying. In general, any method of applying the fluorochemical would be acceptable.

Figure 5:
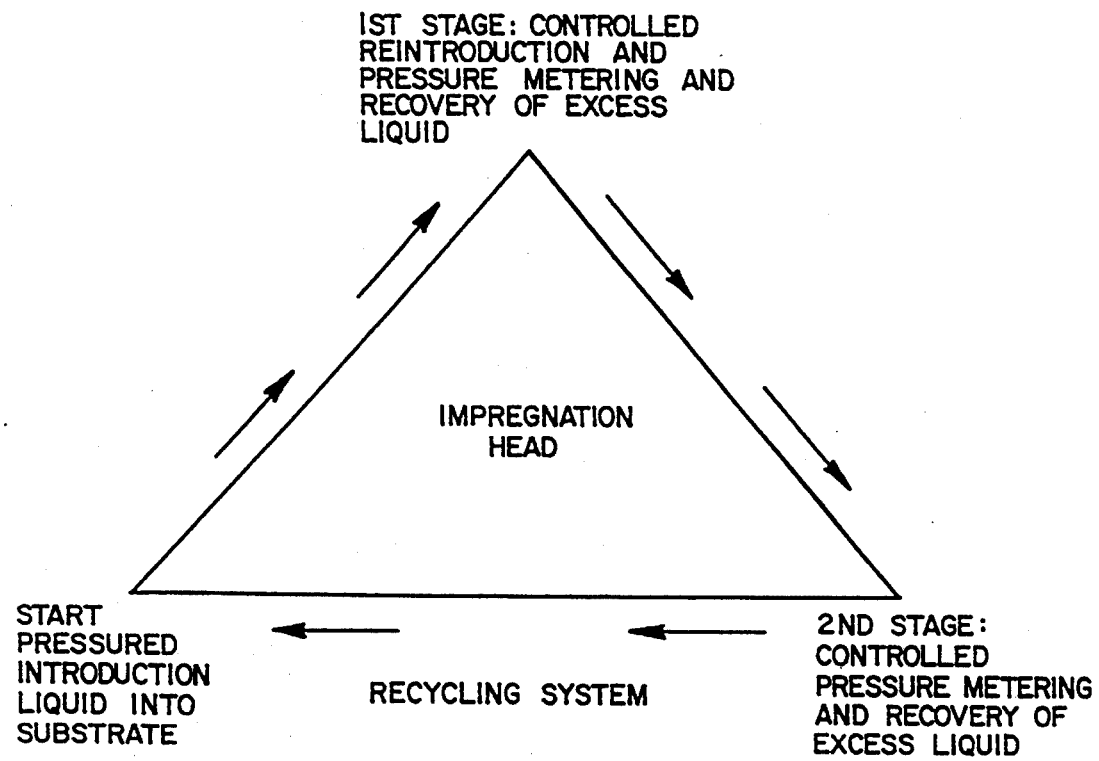
FIG. 5 is a diagrammatic representation illustrating the process in accordance with the present invention.

Another embodiment of a machine suitable for accomplishing pressurized impregnation in accordance with this invention is shown diagrammatically in FIG. 5 which also illustrates a process embodiment of this invention. At an impregnation head, pressurized introduction of the silicone polymer composition into the web is first carried out. At a subsequent stage, controlled pressure reintroduction, distribution, and metering of the silicone polymer impregnant and recovery of excess impregnant transpires using a shear knife or blade which applies transverse force against the impregnated web laterally across the web. In a subsequent stage, further controlled pressure reintroduction and metering takes place by means of a flexible blade, such as a so-called flex-knife or Spanish knife. Here, additional recovery of excess liquid impregnant is accomplished. In all knife-applying states, the excess impregnant removed is collected and preferably passed by a recycling system back to the initial, pressured introduction stage to achieve process operating economies. Still further successive impregnant pressure reintroduction stages may be used if desired. The direction of the arrows in the diagrammatic representation of FIG. 5 shows the general direction of movements in the region of the impregnation head, including the general direction of impregnant movement in the practice of such process.

The apparatus employed in the present invention functions first to apply and preferably concurrently impregnate a silicone polymer composition into a web under pressure. Such silicone polymer composition is then reintroduced, distributed, and metered in a controlled manner in the web with the aid of transversely applied shearing force and compressive force such that the impregnated composition becomes distributed in the web so that an internal layer of silicone is formed while the fibers are at least partially enveloped while the interstices or open cells are substantially completely filled with the silicone polymer composition in the region of the internal coating. During treatment, the web is longitudinally tensioned and the pressurized application and impregnation and the subsequent shearing and compressive actions are successively accomplished in localized zones preferably extending generally laterally across the web (that is, generally perpendicularly to the direction of such longitudinal web tensioning) using transversely applied force exerted locally against surface portions of the web during each impregnation and shearing operation. The web is conveniently and preferably, but not necessarily, moved longitudinally relative to such laterally extending web processing zones. The impregnation, shearing and compressing steps are preferably carried out successively or sequentially. Such zones are themselves preferably at stationary locations while the web is moved, but if desired, the web can be stationary while the zones are moved, or both. The result is that the silicone polymer composition impregnant flows into the web and is distributed internally generally uniformly to a predeterminable and controllable extent.

Figure 6:
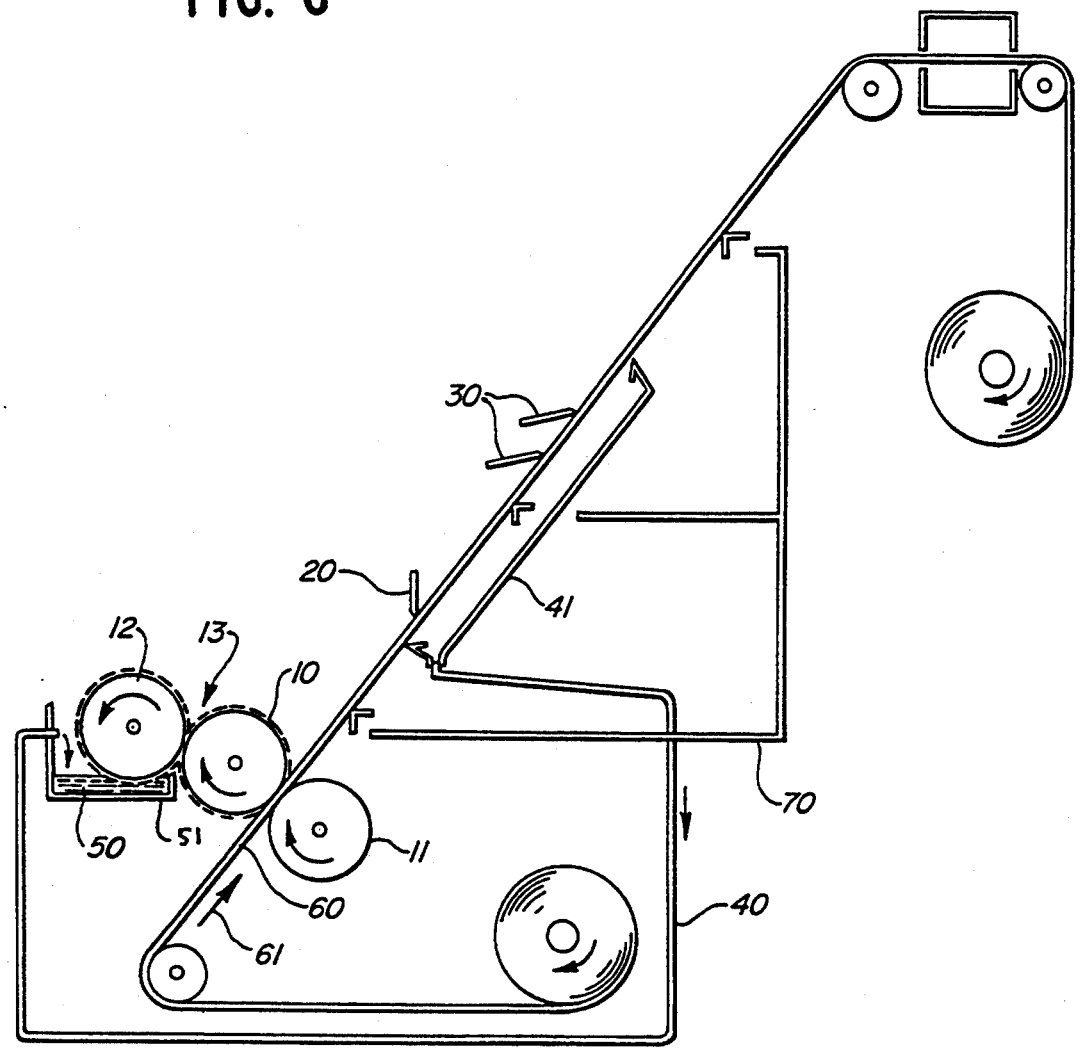
FIG. 6 illustrates diagrammatically another embodiment of an apparatus suitable for use in the practice of the present invention.

A schematic side elevational view of another embodiment of a suitable pressurized impregnation machine for use in the practice of the invention is shown in FIG. 6. This machine continuously moves a longitudinally tensioned web 60 successively through a pressure impregnation station which incorporates a reverse roll coater having rollers 10 and 11, a shear station which incorporates a shear knife 20, and a finishing station which employs at least one so called flex-knife (or Spanish knife) 30. Optionally, but preferably (for reasons of process operating economics) excess silicone polymer composition that is removed from web surfaces in the shear station and finishing station is returned to the pressure impregnation station for reuse using liquid recovery and recycle system 40. In the pressure impregnation station, a silicone resin impregnant 50 is contained within reservoir 51. Roller 12 rotates in the indicated direction so that its circumferential surface, preferably a textured or gravure surface, picks up liquid 50 from reservoir 51 and deposits it on the circumferential surface of roller 10 across a controlled width gap 13 between rollers 10 and 12. Typically, gap 13 is actually less than the unencumbered thickness of the starting web 60. Roller 10 also preferably has a textured or gravure surface. Roller 10, rotating in the roller arrow indicated direction, which is opposite to the direction of travel of web 60, applies the silicone polymer impregnant to one surface of the moving web 60, which is typically a fabric. Roller 11 is urged with a compressive force against the back or opposed surface of web 60 and roller 11 rotates in a direction which is the same as that in which web 60 travels. Roller 11 aids in achieving the desired pressured impregnation of web 60 by impregnant from the surface of roller 10.

Referring to FIG. 6, the impregnant is believed to be introduced into the web and into the interstices or open cells of the web 60 by the aid of a back-pulling or shearing action resulting from the distorting and pressuring of web 60 caused by rollers 10 and 11 rotating in the same direction. This direction may be the indicated direction with roller 10 rotating against the linear movement of web 60 indicated by web directional arrow 61, or all rollers 10, 11 and 12 may be reversed in respective rotational direction so as to cause each roll to turn in an opposite direction relative to that direction which is illustrated by the respective roller arrows in FIG. 6. Regardless of which side of web 60 is back-pulled or subjected to shearing action by a reverse rotating roller, the web 60 is stretched and distorted to pull open the interstices of the web and to aid in impregnating web 60 with silicone polymer impregnant 50. This distorting, and particularly this stretching, is believed to facilitate the full and deep introduction of the impregnating liquid into the moving web 60.

The extent of pressured impregnation of the silicone polymer impregnant 50 into the web 60 which occurs between rotating rollers 10 and 11 is controllable to some extent by such variables as the speed of roller rotation, the pressure exerted by rollers 10 and 11 on web 60, the durometer hardness and surface characteristics of each roll 10 and 11 (particularly of the preferred textured or gravure surface of roll 10). However, the pressurized impregnation may also be carried out with rollers 10 and 11 which have finely milled, smooth circumferential surfaces. The viscosity of impregnant liquid 50 and the amount of impregnant liquid 50 transferred from roll 12 to roll 10 across gap 13 may also be varied to regulate impregnation. Feed roller 12 preferably rotates counter to application roller 10. The impregnant 50 can be monitored to assure that its homogeneous composition is maintained. If desired, the impregnant 50 formulation can be altered to adjust to process needs during a continuous treating operation.

The result of the pressured web 60 impregnation which is accomplished between rollers 10 and 11 using a silicone polymer composition impregnant 50, which can have the viscosity or consistency of a conventional bathtub caulk composition, is to produce a web 60, or fabric, whose interstices or open cells are substantially completely filled with impregnant in the region of the internal coating. In, for example, the case of a fabric, the impregnation extent can be such that spaces (i.e., interstices or open cells) between the fabric's fibers/filaments, or the fabric's yarn members (as the case may be) are filled with impregnant 50. However, the amount of impregnant 50 which is thus introduced into web 60 can be much less than a saturation level; for example, the amount introduced can be insufficient even to coat or substantially completely envelope individual fibers of the web. Actually, the impregnant 50 can be relatively non-uniformly distributed in the web after such pressurized impregnation. The action of the shear knife 20 in the next zone of processing is such as to smooth out and to make uniform the distribution of impregnant 50 in web 60. Also, the shear knife 20 helps regulate the amount of impregnant 50 that is allowed to remain in web 60.

After the shear zone, if desired, a top coat polymer can additionally be introduced; for example, just before or after a flex knife 30. By overcoating, for example, the original impregnant with a dilute or very thin second or top coat, a more tightly cross linked impregnated or enveloped product may be achieved, or surface properties of the product can be varied or improved. For example, the top coating can comprise a dilute dispersion of a fluorochemical fabric treating composition. In a web treated therewith, such treatment enhances surface properties of the web, such as by increasing grease or chemical penetration resistance, or soil resistance, or the like. The dilute fluorochemical dispersion can be applied by spraying, misting, or the like. Both treating agents then enter a curing stage, which can be accomplished conveniently by passing the treated web through an oven wherein the temperature and web residence time are sufficient to cure both the fluorochemical and silicone polymer impregnants to a desired extent, or by radiation, if desired.

The amount of silicone polymer impregnant actually introduced through the pressured impregnation, and into the preferably stretched openings of the interstices of the web 60 is influenced by such factors as the velocity of movement of web 60, the viscosity characteristics of impregnant 50, the compressive pressure exerted by roll 10 against roll 11, the longitudinal tension exerted upon the tensioned web 60, impregnant distribution achieved by shear blade 20 and by scraper flex knive(s) 30, and the like. In particular, the impregnant reintroduction and distribution believed to be achieved by bar or shear knife 20 is achieved by the exertion of a pressure against moving tensioned web 60. The shear force and the temperature elevation due to such shear force results in the impregnant 50 flowing upon the three dimensional structure of the web 60 and the knife 20.

Preferably, the impregnant 50 is thixotropic. The flowing of the impregnant 50 into the web 60 using controlled liquid rheology preferably does not result at the time of impregnation in a fluid viscosity which is so low as to cause the impregnant to spread into and be distributed substantially uncontrolled throughout the web 60. However, the flowing activity of the impregnant is preferably accomplished using an impregnant 50 which has a controllable rheology and viscosity such that an impregnant 50 will achieve a desired envelopment of individual fibers of the web 60. Particularly when the web 60 is a fabric, this envelopment is preferably a surrounding of the fabric's individual fibers with a localized layer or film of silicone polymer while an internal layer is formed.

A plurality of web tension control devices 70 can be used in the region of metering bar or shear knife 20 and in the region of reintroduction scraper flex knives 30 along web 60 in order to provide the capacity for precision control of the tension exerted on web 60 and of the compressive pressures and shear forces exerted on web 60 at the metering bar or shear knife 20 and flexible knives 30.

As shown in FIG. 6, the machine preferably includes an impregnant 50 recovery and recycling system which more preferably also includes a filtering subsystem, such system being diagrammatically represented and indicated by dashed line path 40. This system includes a collection tray, or pan, 41, positioned under and behind the moving web 60 to collect along the sides of web 60, the excess impregnating liquid as it is wiped from the web surface contacted by the metering bar 20 and/or by the recovery knives 30 and passed laterally into pan or tray 41. From the recovery collection tray 41, the excess impregnant 50 is pumped back through filter 42 into the reservoir 51 of the reverse roll coater for loading and distribution on the surface of roller 12, transfer to roller 10, and reapplication to portions of continuously moving web 60. The ability to reuse the excess impregnant 50 wiped from the moving web 60 rather than losing such impregnant within the process makes the entire process more economically attractive.

Figure 7:
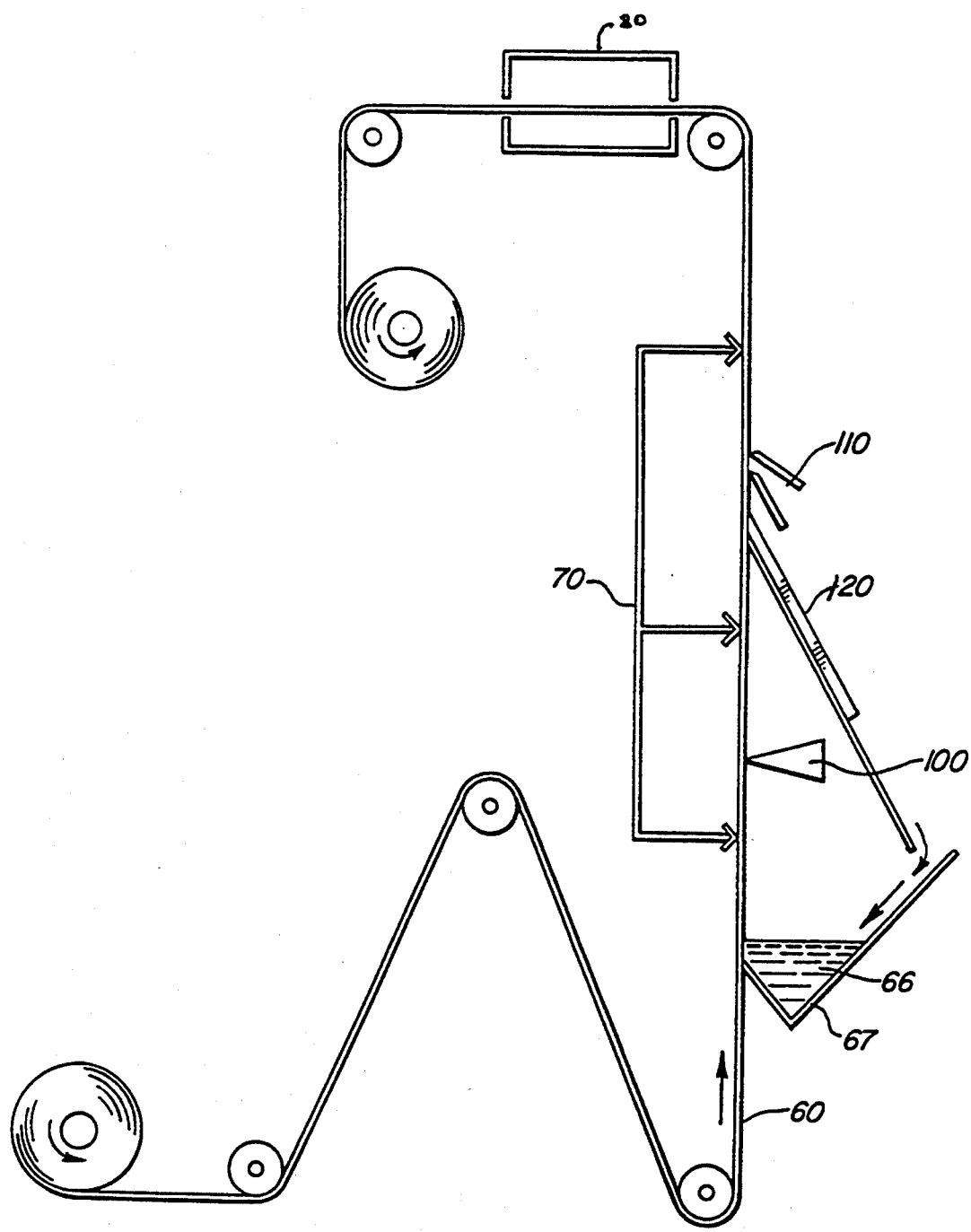
FIG. 7 illustrates diagrammatically another embodiment of an apparatus suitable for use in the practice of the present invention.
Figure 8A:
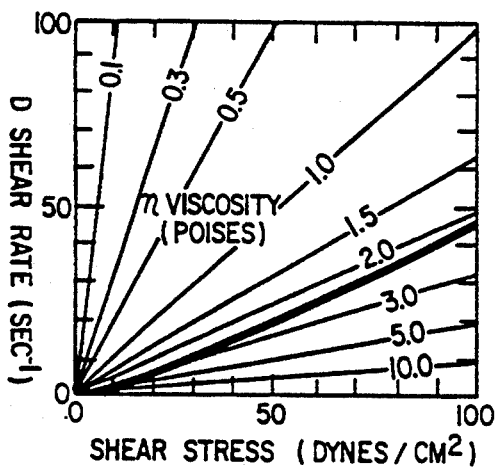
FIGS. 8a through 8d are graphs illustrating ways of plotting rheological behavior.
Figure 8B:
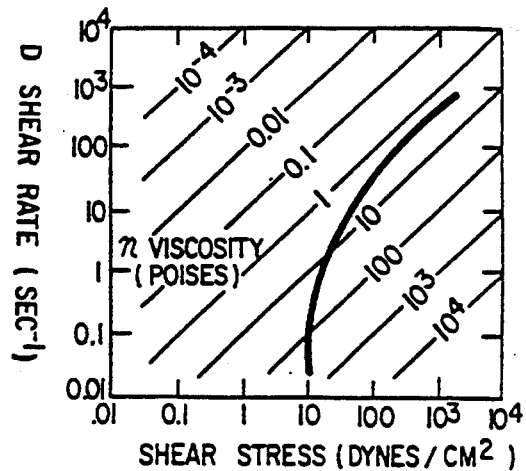
Figure 8C:
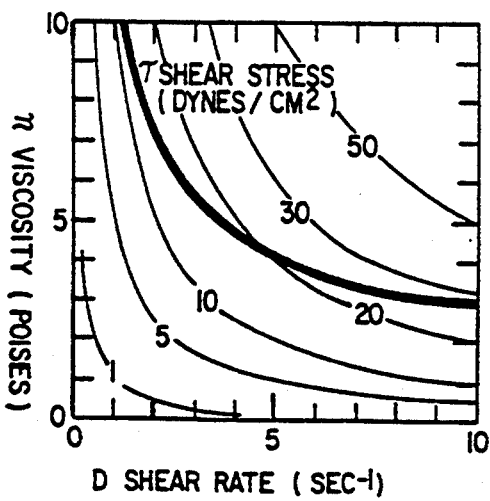
Figure 8D:
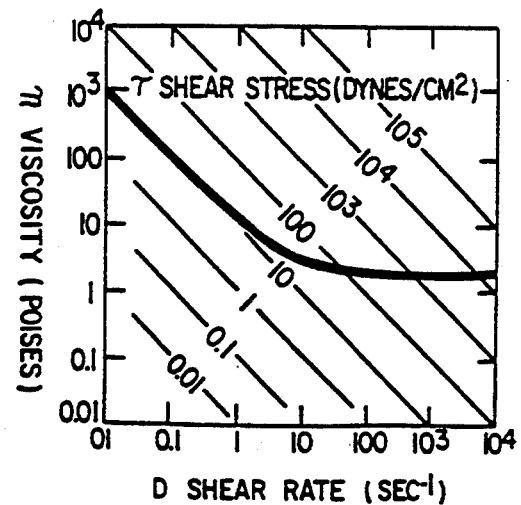

Another embodiment of a machine suitable for use in the practice of this invention is shown schematically in side elevation in FIG. 7. In this embodiment, rollers 10 and 11 of the FIG. 6 apparatus are replaced with a combination of a reservoir 51, and a bar or shear knife 100. The reintroduction bar or shear knife 100 pressurizes the impregnant liquid 50 which is applied or deposited onto the moving web 60 from the reservoir 51 as a liquid or bath. The web 60 in effect constitutes a retaining wall for a part of the reservoir 51. The reservoir 51 thus functions to hold a pool of the silicone polymer composition impregnant 50 against a surface of the moving web 60 which in the embodiment shown, is moving vertically upwardly. The bar or shear knife 100 functions to apply pressure or force upon the silicone polymer composition impregnant 50 that was deposited on the web 60, thereby to cause the impregnant 50 to penetrate the web 60. The knife 100 also serves to distribute and move the impregnant in the web and to accomplish envelopment of the fibers thereof. Excess impregnant 50 is also scraped away by knife 100. Optionally, one or more of flex knives 100 function to further reintroduce, distribute the impregnant 50 and to envelope fibers of web 60 while forming an internal silicone polymer coating within the web. The knives 110 can be considered to function in a manner which is equivalent to the knives 30 on the treated surface of web 50 in the FIG. 6 apparatus.

Typically, any impregnant scraped from the moving web 60 by bar knife 100 falls directly back into the reservoir 51. Impregnant scraped from the moving web 60 by scraper knife 110 is collected in sloping trough 120 and returned by falling along the indicated dotted line path to the reservoir 51. Longitudinal tension control of the moving web 60 is regulated by tension control devices 70 (as in the FIG. 6 embodiment) from a region beginning after reservoir 51 and extending to an oven 80 along the path of web 60 travel.

Relative to the FIG. 7 embodiment, the FIG. 6 embodiment is believed to exhibit a wider degree of control in the practice of the present impregnation process. Particularly, both the initial applied amount and the successive pressurings of, a silicone polymer impregnant 50 are precisely controllable. Relative to the FIG. 6 embodiment, the FIG. 7 embodiment is characterized by the capability for operation at higher web 60 transport speeds, typically at speeds characteristic of higher end commercial fabric finishing line operations. The embodiment shown in FIG. 6 is believed to be suitable for producing internally coated fabrics when the fabrics are of the thicknesses characteristic of garments, and where deeply controlled pressured impregnation over distances extending perpendicularly into and through a web of fabric greater than about 1/16 inch is not generally required.

Illustrative parameters of the adjustments of the first embodiment of apparatus shown in FIG. 6, are contained within the following three Tables III, IV and V. The first column of each Table lists a parameter that is adjustable. For Table III, these parameters concern top roller 10 shown in FIG. 6. For Table IV, these parameters concern reintroduction metering bar or shear knife 20 shown in FIG. 6. For Table V, these parameters concern web tensioning devices 70. The second column of each Table indicates the typical respective ranges of parameter adjustment. The third column of each Table indicates the effect of such adjustments on web impregnation.

TABLE III

MACHINE ELEMENT PARAMETERS
First Stage Introduction Pressure Rollers:

| Top Roller Adjustment Parameters | Variability to Adjustment | Effect of Adjustment of Web |
|---|---|---|
| Top roller pressure down and in at an angle or in front of roller | 0 to 500 lbs/ linear inch | Delivery quantity, depth, residue presence both at lower yarn level and a fiber or filament level |
| Top roller surface | Smooth to highly textured | Degree of agitation and distortion or friction action |
| Top roller speed | 50 to 1,000 RPM | Varies quantity by varying speed and distortion independent of web speed in relation to second and third stage systems |
| Metered Film Thickness on top roller | .05 mil thick non-contiguous film to 10 mil on roller | Contiguous film delivery quantity controlling thicker film presence and allows more impregnant to dam at either second or third stage |
| Lower roller surface and composition | Low durometer material surface to high strength metals | Low durometer material allows pressure from upper roller to be agitation of yarn bundles or filament's metal surface causes more complete distortion and agitation of yarn and fiber/filament |

TABLE IV

MACHINE ELEMENT PARAMETERS
Second Stage Reintroduction Bar Knife:

| Adjustment Parameters | Variability to Adjustment | Effect of Adjustment of Web |
|---|---|---|
| Angle of bar knife | Bar knife faces forward to meet web coming to bar; bar knife to web, bar faces away or racked back from web run direction | Angle effects shear forces on impregnate and determines distortion or vertical agitation as it relates to causing flow of impregnate; can determine reintroduction of impregnate by dammed quantity of impregnate |
| Edge Shape | Knife very | Sharpness of knife |

TABLE IV-continued

MACHINE ELEMENT PARAMETERS
Second Stage Reintroduction Bar Knife:

| Adjustment Parameters | Variability to Adjustment | Effect of Adjustment of Web |
|---|---|---|
| | sharp | affects shear forces. The sharper and thinner the edge, the greater the shear forces at the contact edge |
| Pressure | Relates to web tautness | Greater pressure increases forces at contact edge |

TABLE V

MACHINE ELEMENT PARAMETERS

| Adjustment Parameters | Variability to Adjustment | Effect of Adjustment of Web |
|---|---|---|
| I. Second Stage Bars Below Web: | | |
| Web Speed | Range of machine speed possible | Affects the shear forces at contact edge above, where impregnant is being forced into the web |
| Pressure on web | Range of motion of bar | Tightens or loosens tension on web which in turn affects shear forces at contact edge |
| II. Third Stage Reintroduction Flex Knife: | | |
| Recovery system | | Filters and pumps deliver impregnant back to first introduction stage |

Figure 12A:
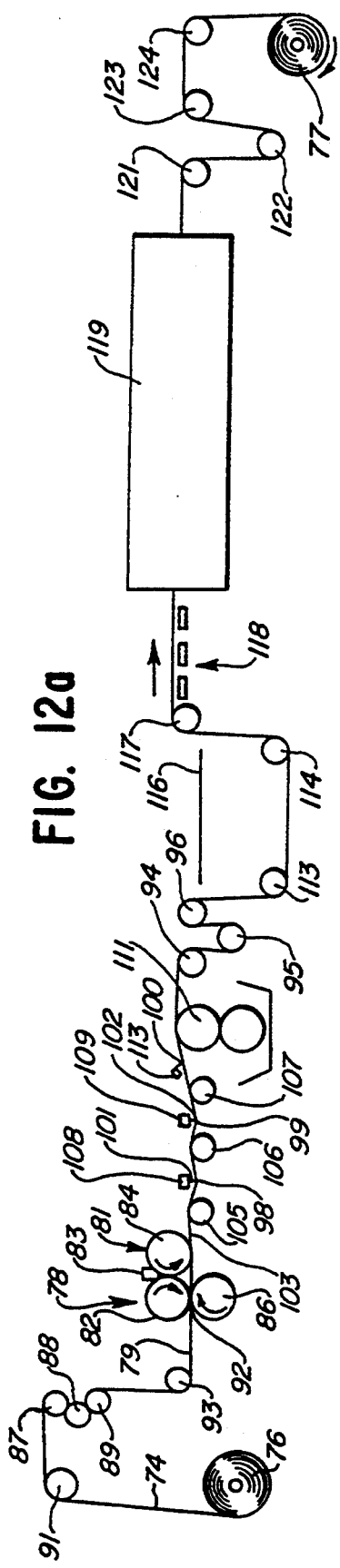
FIGS. 12a through 12c illustrate diagrammatically another and presently preferred embodiment of apparatus suitable for use in the practice of the present invention.

A schematic, side elevational view of another suitable pressurized impregnation system or apparatus 73 for practicing the present invention is shown in FIG. 12a. In this apparatus, a continuous web 74 is moved along a web pathway from a supply roll 76 to a take-up roll 77.

In a first functional processing station 78, a silicone polymer composition is applied to one face (here, the upper face 79) of web 74 by a conventional reverse roll coater apparatus 81 wherein such composition is applied to the surface of a reversely rotating (relative to the direction of travel for web 74) coating roll 82 from a nip region reservoir 83 formed between the coating roll 82 and a transfer roll 84 (which rotates in the direction of travel for web 74, but whose surface does not contact web 74). The web 74 is transversely compressed between coating roll 82 and drive roll 86 as it passes through station 78. Thus, the polymer composition is applied under a positive pressure against face 79 by coating roll 82 which functions to cause the composition to be impregnated into web 74. A present preference is to use a coating roll 82 which has smooth, chrome plated surfaces.

Largely for purposes of controlling the alignment of web 74 with rolls 82 and 86, the web 74 is pretensioned by coacting clutching rolls 87, 88 and 89. After it passes over guide roller 91 on the web pathway from supply roll 76, the web 74 passes over roll 87, between rolls 87 and 88, around roll 88, and between rolls 88 and 89. The clutching rolls 87, 88 and 89 are components of a conventional web clutching mechanism (not detailed) which provides for adjustments between rolls 87, 88 and 89 so that selective tensioning of web 74 is achieved along the web pathway between the clutching rolls 87, 88 and 89 and the nip region 92 defined between rolls 82 and 86 with the intervening roller roll 93 being used for guidance of web 74. The clutching rollers 87, 88 and 89 also function to smooth out and extend web 74 before it enters the coater apparatus 81 so that in the apparatus 81, the web will have polymer composition uniformly applied thereto.

After passing nip region 92 the web 74 is preferably highly longitudinally tensioned along the web pathway extending from nip region 92 to compensating and regulating coacting tension rollers 94, 95 and 96. The tension rollers 94, 95 and 96 are components of a conventional web tension adjusting and regulating mechanism (not detailed) which provides for on-line, in-stream operator controlled adjustments between rollers 94, 95 and 96 that permit selective control of the tautness of web 74 particularly in the web pathway region from nip region 92 to rollers 94, 95 and 96.

Along the tensioned web pathway region, the web 74 successively passes through each one of a series of processing stations 98, 99 and 100.

At each of the stations 98 and 99, a substantially non-flexible shear knife 101 and 102, respectively, extends laterally across web 74 with the web 74 being entirely unsupported on the lower face 101 thereof which is opposed to upper face 79 and to the respective blades of each shear knife 101 and 102. Both to control the amount and type of shear force independently applied by each knife 101 and 102 the web 74 passes over each knife edge in a contacting relationship and three idler rolls 105, 106 and 107 that are provided in a typically fixed (but off-line adjustable) relationship relative to knives 101 and 102 as apparatus 73 is operated.

Relative to the direction of web 74 travel, idler rolls 105 and 106 thus are positioned so that roll 105 is on the lead side, and roll 106 on the trailing side, of knife 101 while idler rolls 106 and 107 are positioned so that roll 106 is on the lead side, and roll 107 is on the trailing side of knife 102. The angle of inclination or tilt of each blade 101 and 102 relative to the vertical is adjustable over a wide range, but it is presently preferred to adjust the blade inclination angle for each blade between about ±45° relative to the vertical with the bar 74 being horizontal. In the apparatus embodiment 73 shown, each respective blade is functionally associated with a knife back support 108 and 109, respectively. Each support 108 and 109 permits its associated blade 101 and 102 to be adjustably inclined in relation to the vertical relative to a supporting frame (not shown).

Another adjustable variable is the amount of angular web depression which, in the embodiment shown, extends downwardly, achieved by the web in its passage over the circumferential edges of adjacent rolls 105 and 106 relative to knife 101, and in its passage over the circumferential edges of rolls 106 and 107 relative to knife 102. Considering the place where the knife 101 or knife 102 contacts the web to be a hypothetical point, the angle of the knife 101 or knife 102 relative to the web can be in the range of about 30° to about 140°.

While it is presently preferred to employ shear knives 101 and 102 which have straight edges, it will be appreciated that shear knives having somewhat curved edges can be used, if desired. For example, when treating a web which displays differential longitudinal stretch characteristics laterally thereacross in response to a uniform laterally applied warp tension, it appears to be possible to equalize the shear forces applied to a web by employing a suitably curved shear knife which appears to compensate for such a differential stretch characteristic.

While it is presently preferred to employ shear knives 101 and 102 which have sharp edges, more preferably edges which are sharpened to a micro edge uniformity of at least about root mean squared (RMF) 8 shear knives can be used which have dull or rounded edges.

While it is presently preferred to employ shear knives 101 and 102 which are formed of steel, other materials of knife construction could be used if desired, such as metal alloys, non-metallic composites, and the like.

Those skilled in the art will appreciate that the amount of shear force applied by a shear knife 101 or 102 transversely against a web 74 is a function of many variables with probably the most important or principal variables being the fluorochemical pretreatment, the silicone polymer viscosity and the longitudinal web tension (assuming a fixed spatial position for idler rolls 105, 106 and 107 and shear knives 101 and 102 during operation).

When a suitable and preferred level of applied shear force and web tensioning has been achieved to produce a product having enveloped fibers and an internal silicone coating, one can usually hear a distinctive sound in the region of a shear blade 101 and 102. This sound can also be heard in the vicinity of shear blades being used in the operation of other processes described herein. This sound can in fact be used by an operator as a rough guide as to whether or not he is succeeding in producing a silicone polymer impregnated product containing enveloped fibers and an internal coating.

Idler roll 105 also functions as a compensator roll for mechanically adjusting and controlling web tension after coating apparatus 81 and before knife processing begins. Also, conveniently and preferably the web tension is sensed electronically, and then roll 105 is automatically raised or lowered to achieve web tensioning adjustments so as to maintain a preset tension in web 74.

After passing over roll 107, the web 74 is passed over the circumferential surface of a conventional padder roll 111.

Between the idler roll 107 and the padder roll 111, a flexible so-called "flex-knife" or "Spanish knife" 100 is positioned. Preferably, the blade of this flexible knife 100 is inclined at an angle with respect to the web 74 passing thereagainst so that the knife 100 exerts a compressive force against the face 79 of web 74 with opposed face 103 being entirely unsupported. The angle with respect to a (hypothetical) perpendicular line extending into a (hypothetical) straight line extending from the circumferential edge of roll 107 to the circumferential edge of roll 111 can range from about 30° to about 140° for the adjustment of the inclination angle of the flex knife. To provide adjustability for flexible knife 100, knife 100 is functionally associated with a mounting bracket or back support 113 which in turn is adjustable relative to an apparatus frame (not shown).

In the embodiment shown in FIG. 12a, the padder roll 111 is not employed as a web 74 treating means.

After leaving the mechanical tension compensator rolls 94, 95 and 96, web 74 is under reduced or preferably minimal tension and is led along a pathway which extends over spacer rolls 113 and 114. In the region over spacer rolls 113 and 114, and generally between tension roll 96 and idler roll 117, a platform 116 is conveniently positioned which can incorporate suitable instrumentation panels, operating controls and the like so that an operator can observe the operation of the apparatus 73 in the practice of the process of this invention and then control and regulate the same. A position which is suitable for operator observation of a web in progress that is located in the vicinity of the tenter frame 118 is desirable because it has been observed that a web being processed can experience some distortion owing to the forces exerted thereon. These distortions can be metered and observed and then the tenter frame 118 adjusted by the operator so that, as the web passes therethrough, the web can be straightened or shaped either longitudinally or laterally, as desirable or considered necessary for an individual web. If desired, the tenter frame 118 can be automatically operated to apply tensioning forces to a web in accordance with a predetermined program, or the like.

The tenter frame 118 also provides the start of a new zone of limited longitudinal and transverse tensioning which extends forwardly along the web pathway from tenter frame 118 through oven 119 to a tension compensator, here shown as utilizing three tension rolls 121, 122 and 123 which are part of a conventional mechanical tension compensator subassembly which is similar in structure and function to the compensator subassembly incorporating the previously described tension rolls 94, 95 and 96. The tensioning longitudinally of web 74 as it passes through oven 119 is employed to control the web 74 as it passes through oven 119 as regards web dimensional limits. This tensioning is chosen to be at a level which does not introduce significant distortion into the web, yet web sagging is avoided, as from thermal expansion and elongation. Rollers (not shown) can be used in the oven 119 to avoid sagging and to maintain uniform heat exposure.

In addition to serving as tension regulating means, the rolls 121, 122 and 123 also serve to provide a cooling pathway for the web 74 as it emerges from the oven 119 before it passes over guide roller 124 and into take-up roll 77.

The oven 119 functions to cure the silicone polymer composition thus impregnated into web 74. Oven 119 can be operated with gas or other energy source oven 119 can extend for from about 12 to 20 yards, a 15 yard long oven being convenient.

Curing temperatures of from about 320° to about 500° F., applied for times of from about 2 minutes to about 30 seconds (depending upon the temperature) are desirable. If a curing accelerator is present in the silicone polymer, curing temperatures can be dropped down to temperatures of about 265° F. or even lower (with times remaining in the range indicated).

In place of an oven, or in combination with an oven, a source of radiation can be employed (electron beams, ultraviolet light, or the like) to accomplish curing, if desired.

Less than the full heating capacity of the oven 119 can be used, if desired, or if full oven capacity is not needed, either longitudinally or vertically. For example, only top heating or only bottom heating with respect to the web can sometimes be used as compared to a combination of both top and bottom heating.

The take-up roll 77 is operating at approximately the same speed as the supply roll 76. When the rotational speeds of take-up roll 77 are not synchronized with rotational speeds of the supply roll 76, the tension roll combination of rolls 121, 122 and 123 can be used to take up or reduce web slack, as the case may be.

Web transport speeds can vary widely; for example, from about 2 yards per minute to about 90 yards per minute.

Figure 12B:
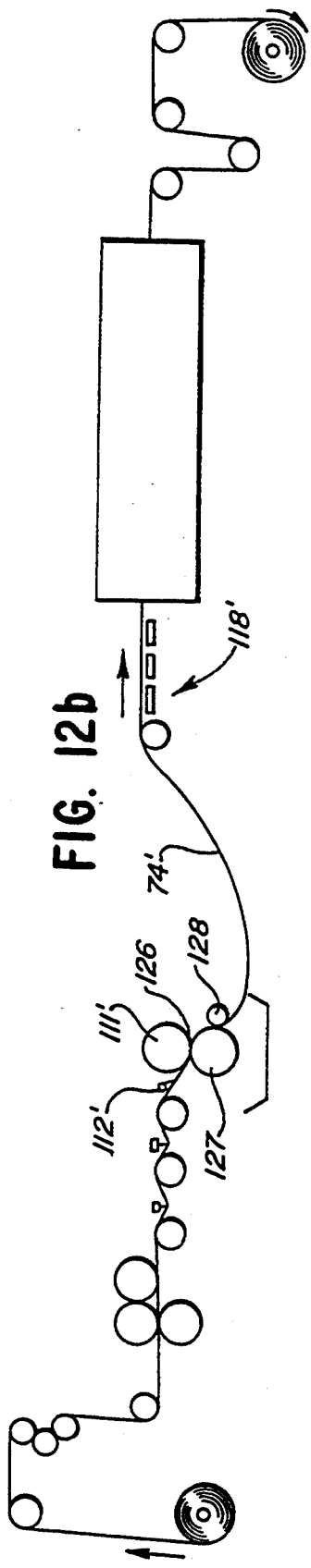
Figure 12C:
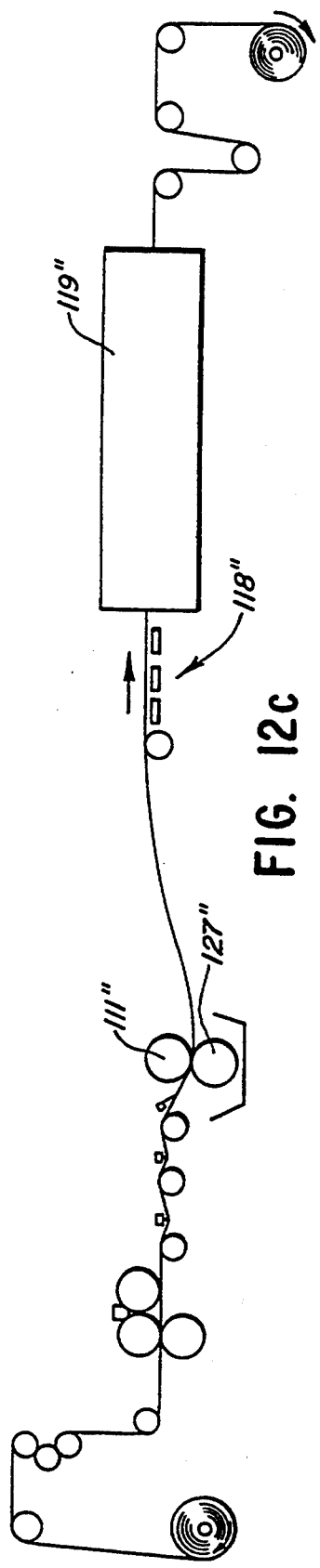

The process described above can be used in various forms or embodiments. Referring to FIGS. 12b and 12c, two alternate variations or modes are seen. In such views, similar components are similarly numbered but with the addition of single prime marks thereto in the case of FIG. 12b and double prime marks thereto in the case of FIG. 12c.

In FIG. 12b, a further stage of web pressurization is introduced after the flex knife 112' and before the tenter frame 118'. Here, the web 74' after passage through the flex knife 112' is passed through the nip region 126 existing between padder roll 111' and associated transfer roll 127 where the web 74' is subjected to compression between such rolls 127 and 111' for the purpose of achieving a better distribution of silicone polymer composition on web 74'.

After leaving nip region 126, the web 74' is retained under some compression against roll 127 by means of retaining bar or roll 128 for similar purposes.

If desired, the roll 128 can be replaced by a flex knife (not shown) over whose edge the web 74' passes after departure or preparation from roll 127. The flex knife can accomplish substantial further polymer distribution in web 74'.

Referring to FIG. 12c, there is seen an embodiment where the web 74" is passed through the nip region of rolls 111" and 127". Here not only is use of the mechanical tension roll combination having rolls 94, 95 and 96 (as in FIG. 12a) eliminated, but also the rolls 111" and 127" serve to end the region of high longitudinal tension in the stages of blade or knife application to web 74" and to provide the desired reduced pressure for web passage through a curing station, here illustrated by oven 119" which succeeds the desirable and preferred intervening tenter 118".

Typically, and preferably, webs of this invention are characterized by having fiber envelopment layers which range from about 0.1 to about 50 microns.

A presently preferred web which is both fluorochemical and silicone resin treated and which is breathable, water resistant and rewashable is characterized as being a longitudinally tensionable porous flexible fibrous web having opposed, substantially parallel surfaces that are comprised of associated fibers with interstices between the fibers or is a matrix having cells or pores therein. The web is substantially uniformly impregnated with a fluorochemical and thereafter impregnated with a silicone polymer composition, to form a web having an internal layer within the web wherein the outer surfaces of the web are substantially full of silicone polymer and the web is breathable and water resistant or waterproof. At least a portion of the fibers or cell walls are enveloped. At least one surface thereof is characterized by having a visual appearance which is substantially the same as the visual appearance of one surface of the starting porous web.

When the web has fibers comprised of a synthetic polymer, the polymer is preferably selected from the group consisting of polyamides, polyesters, regenerated cellulose, cellulose acetate, and mixtures thereof.

Preferred webs of this invention are more specifically characterized by having a water drop contact angle in the range of about 90° to about 160°; a rewash capability of at least about 3; a breathability of at least about 35% of untreated substrate web; and a water repellency rating of at least about 80 prior to washing.

A general process for making a porous web of this invention comprises the steps of: tensioning a flexible, porous web as above characterized, applying a curable silicone polymer composition to at least one web surface and then moving over and against one surface of the tensioned web a uniformly applied localized shear force to: uniformly distribute the composition within the web, at least partially individually envelope surface portions of at least some of said fibers or passageways through the web matrix with said composition in a desired web internal region. Thereafter, the web is subjected to conditions sufficient to cure the composition in said web. Curing is accomplished by heat, by radiation, or both.

A presently preferred process for making a fluorochemical and silicone resin treated web having breathability, water resistance and rewashability which is adapted for continuous operation comprises the successive steps of: impregnating the web with a fluorochemical, longitudinally tensioning the fluorochemical impregnated web while sequentially first applying to one surface thereof a curable silicone polymer composition and concurrently applying a transversely exerted localized compressive force against said surface, and moving over said surface of the web substantially rigid shearing means which exerts transversely an applied, localized shear force against said surface and wipes away exposed portions of silicone polymer composition on said surface, thereby forming an internal layer of silicone polymer while enveloping at least some of the fibers or passageways through the matrix; and curing the silicone polymer composition in the web.

The fluorochemical impregnation operation is conveniently and preferably carried out by the steps of: substantially completely saturating the web with a solution or dispersion of a fluorochemical composition in a carrier liquid; compressing the saturated web to remove therefrom excess portions of said dispersion; and heating said web to evaporate the carrier liquid therefrom. However, any convenient process can be used for accomplishing fluorochemical pretreatment of a web to be used in this invention.

The following text concerns the theory of the invention as it is now understood; however, there is no intent herein to be bound by theory.

The presently preferred polymer impregnant used in the pressure impregnation and knife blade treatment of webs by this invention is a non-Newtonian liquid exhibiting thixotropic, pseudo-plastic behavior. Such a liquid is temporarily lowered in viscosity by high pressure shear forces.

One aspect of the invention is a recognition that when high forces are applied to curable silicone polymer compositions, such as those as viscous as bathtub caulk, then the viscosities of these materials can be lowered perhaps up to 99% or more. Conversely, when cured (polymerized and/or cross-linked) these compounds increase in viscosity up to perhaps 1,000,000% or more. The internal and external rheological control of silicone impregnant materials achieved by the present invention is believed to be of an extreme level even for thixotropes. When subjected to shear force, the liquid silicone polymer composition can flow more readily, perhaps comparably, to water. When subsequently subjected to curing, the same liquid composition sets to a solid form which can have a consistency comparable to that of a hard elastomeric rubber.

The invention preferably employs a combination of: (i) mechanical pressure to squeeze a silicone polymer composition impregnant into a porous web; (ii) a porous web pretreatment with a water repellent chemical, such as a fluorochemical, which is theorized to reduce the surface tension characteristics of the web and create a favorable surface contact angle between the silicone polymer composition and the treated web which subsequently allows, under pressure and shear force exerted upon an applied silicone polymer composition, the production and creation of an internal coating or layer which envelopes fibers or lines cell walls in a localized region within the web as a result of impregnant flow in the web; and (iii) a liquid silicone polymer composition impregnant preferably having favorable rheological and viscosity properties which responds to such working pressures and forces, and in controllably impregnated into, and distributed in a web. This combination produces a web having the capability for a high degree of performance. This product is achieved through pressure impregnation and applied shear forces brought to bear upon a web so as to cause controlled movement and flow of a silicone polymer composition into and through a web. Preferably, repeated compressive applications of pressure or successive applications of localized shear forces upon the impregnant in the web are employed.

By the preferred use of such combination, a relationship is established between the respective surface tensions of the impregnant and the web, creating a specific contact angle. The impregnant responds to a water repellent fluorochemical pretreatment of the substrate so as to permit enhanced flow characteristics of the impregnant into the web. However, the boundary or edge of the impregnant is moved, preferably repeatedly, in response to applied suitable forces into the interior region of a porous web so as to cause thin films of the impregnant to develop on the fiber surfaces.

The word "thixotropy" refers herein to liquid flow behavior in which the viscosity of a liquid is reduced by shear agitation or stirring. It is theorized to be caused by the breakdown of some loosely knit structure in the starting liquid that is built up during a period of rest (storage) and that is torn down during a period of suitable applied stress.

Thixotropic behavior is preferably built into an impregnant used in the invention by either polymer design or additive/filler design. For example, it now appears that thixotropic behavior can be accentuated by introducing into a silicone polymer composition certain additives that are believed to impart enhanced thixotropy to the resulting composition. A lower viscosity at high shear rates (during application to a web) is believed to faciliate impregnant flow and application to a web, whereas an impregnant with high viscosity, or applied at a low shear rate (before and/or after application) actually may retard or prevent structural element (including fiber) envelopment.

Illustratively, the practice of this invention can be considered to occur in stages:

In stage 1, silicone polymer composition impregnant is prepared can be purchased commercially and comes in typically two parts, designated as A and B. For example, in a silicone polymer composition as taught in U.S. Pat. No. 4,472,470, a base vinyl terminated polysiloxane is the A part, while a liquid organohydrogensiloxane crosslinking agent is the B part. Certain remaining components, such as a resinous organopolysiloxane copolymer and a platinum catalyst may (or can) apparently initially be in either part A or part B.

Stage 2 can be considered to involve the mixing of such a product's parts with or without additives. Changes in viscosity can be obtained and measured based on applied shear rates and shear stresses. Such changes can be experienced by an impregnant with or without additives. Up to a 99% reduction in viscosity of a liquid silicone polymer composition is believed to be obtainable by the shear forces involved in the mixing or infusion of a silicone polymer composition impregnant into a web during, the elapsed applied combination of processing time, temperature, radiation, and/or chemical changes involved. Thereafter, a very substantial increase in impregnant viscosity is believed to be obtainable taking into account these same factors. Normally, the most significant factor is now believed to be the mixing shear gradient that typically reduces the viscosity of the impregnant about 50% below the starting or rest viscosity.

Stage 3 can be considered to be the pressure introduction stage. Up to a 99% reduction of the impregnant viscosity is believed to be obtainable due to the applied shear forces, elapsed time, temperature, radiation and/or chemical changes. Thereafter, a 10,000% increase or even more in the resulting impregnant viscosity is believed to be obtainable. In this stage, curing of the impregnant can take place. Most commonly, impregnant viscosity is decreased during the pressure introduction stage 3 by the application of shear forces.

Stage 4 can be considered to be the first stage internal matrix dispersing and reintroduction with metering, and also recovery and recycle of excess impregnant. Typically, within this stage 4, the shear forces cause a temporary lowering of impregnant viscosity, causing it to flow upon and into the three-dimensional structure of the web. The initial viscoelastic character of the impregnant is typically theorized to be recovered almost immediately after shear forces are removed.

Stage 5 can be considered to be a second stage internal matrix dispersing and reintroduction with metering and also recovery and recycling of excess impregnant. The variations in the viscosity of the impregnant are equivalent to stage 4. The viscosity of the impregnant is again lowered causing it to flow within the web. Because of the application of repeated shear force induced reductions in viscosity, the thixotropic behavior of an impregnant may not undergo complete recovery, following each application of shear force and the viscosity of the impregnant may not revert to its pre-impregnation values. The silicone polymer composition impregnant is believed to have the capacity to form enveloping internal coating in a predetermined region wherein the interstices or open cells are substantially completely filled within the three-dimensional matrix constituting a web during the time intervals that the impregnant is caused to flow under pressure in and about matrix components. In between these times, the impregnant may recover substantially all of its initial high viscosity, although perhaps slightly less so with each repeated application of shearing pressure or force.

Stage 6 can be considered to be occurring just as curing is begun, and just as heat is introduced.

Stage 7 can be considered to be occurring with regard to the exertion of control of curing. Typically, at least a partial curing (including cross-linking and/or polymerizing), is obtained by relatively low temperatures applied for relatively short times, for example, temperatures under about 350° F. applied for under about 3 minutes, when, for example, light cotton, nylon or like fabrics are being impregnated.

FIG. 8, consisting of FIGS. 8a through 8d, shows four graphs illustrating four ways that could be used for plotting impregnant rheological behavior: (a) shear rate versus shear stress (uniform scales), (b) shear rate versus shear stress (log scales), (c) viscosity versus shear rate (uniform scales), and (d) viscosity versus shear rate (log scales), if desired, in the practice of this invention. Only the log versus log scales are believed to be capable of encompassing a full range of values for the three indicated variables. The graphs represent some broad ranges of viscosity changes relative to shear stress that could be undergone by a given silicone polymer composition impregnant during execution of a given pressured impregnation procedure as taught herein.

For the purposes of the present invention, the term "surface tension" can be considered to have reference to a single factor consisting of such variables as intermolecular, or secondary, bonding forces, such as permanent dipole forces, induced forces, dispersion or nonpolar van der Waals forces, and hydrogen bonding forces. The strong primary bonding forces at an interface due to a chemical reaction are theorized to be excluded from surface tension effects; however, it is noted that even a small degree of chemical reactivity can have a tremendous influence on wetting effects and behavior affected by surface tension.

Surface tension is believed to induce wetting effects which can influence the behavior of a silicone polymer composition impregnant relative to the formation of a fiber enveloped layer therewith in a fibrous porous web. For example, adhesion is theorized to be a wetting effect. Spontaneous adhesion always occurs for contact angles less than about 90°. However, for a combination of a rough surface and a contact angle over 90°, adhesion may or may not occur. In fact, roughness becomes antagonistic to adhesion, and adhesion becomes less probable as roughness increases.

Also, penetration is theorized to be a wetting effect. Spontaneous penetration occurs for contact angles less than about 90°, and does not occur for contact angles over about 90°. The roughness of a solid surface accentuates either the penetration or the repellency action, but has no influence on which type of wetting takes place.

In addition, spreading is theorized to be a wetting effect. Retraction occurs for contact angles over 90° or over planar surfaces for any contact angle. However, spontaneous spreading for contact angles less than 90°, especially for small contact angles, may be induced by surface roughness.

Figure 9:
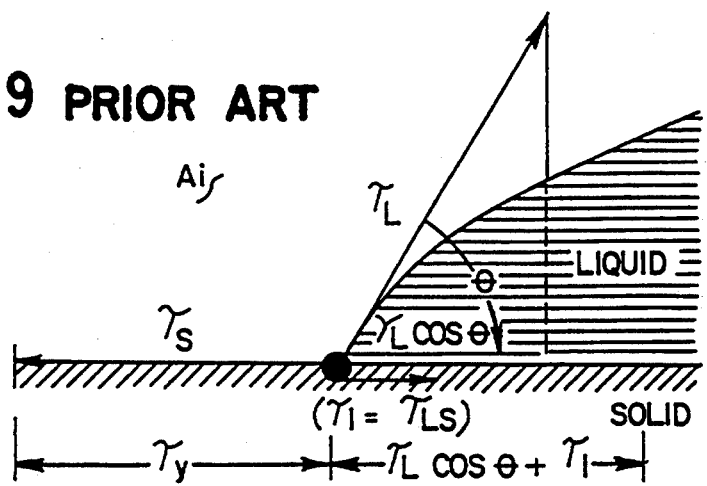
FIG. 9 is a schematic vector diagram illustrating surface tension forces.

FIG. 9 is a schematic vector diagram illustrating the surface tension forces acting at the vertex boundary line of a liquid contact angle on a planar solid surface. It illustrates how surface tension forces might be measured between a silicone polymer composition impregnant and a fiber of a web (or a fabric) as treated by the invention.

Figure 10:
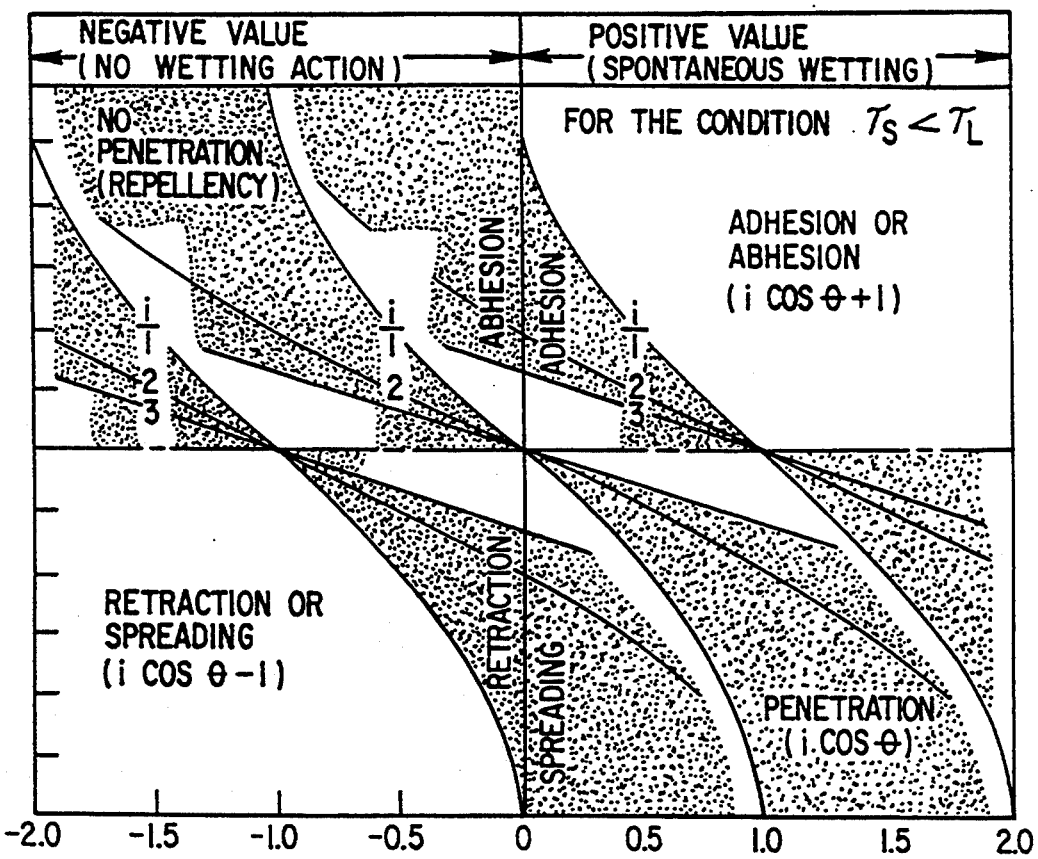
FIG. 10 is a graph relating contact angle over a smooth, solid surface.
Figure 11A:
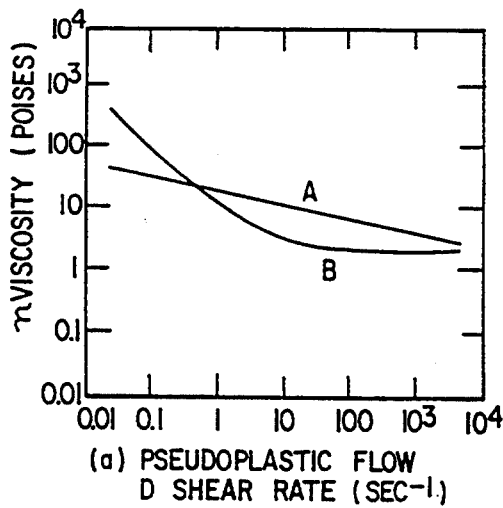
FIGS. 11a through 11d show representative velocity profiles.
Figure 11B:
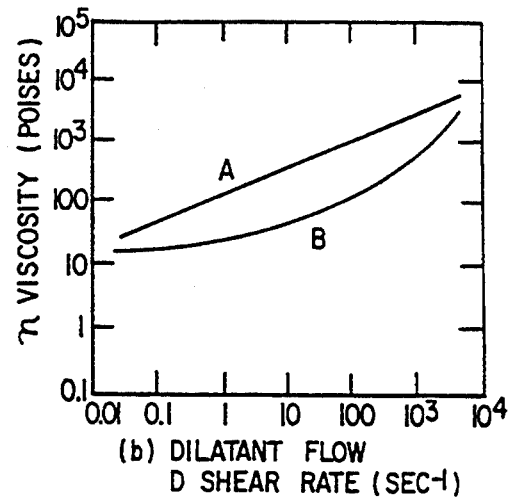
Figure 11C:
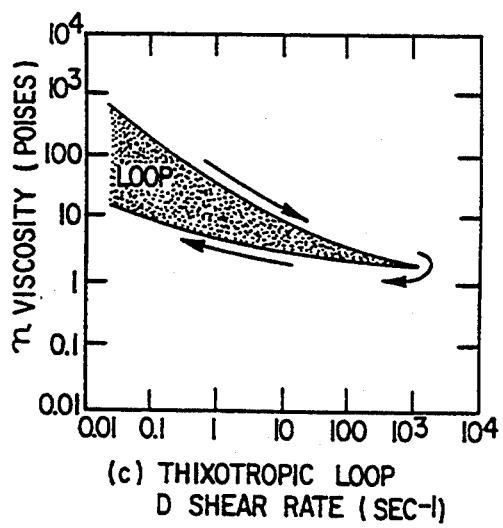
Figure 11D:
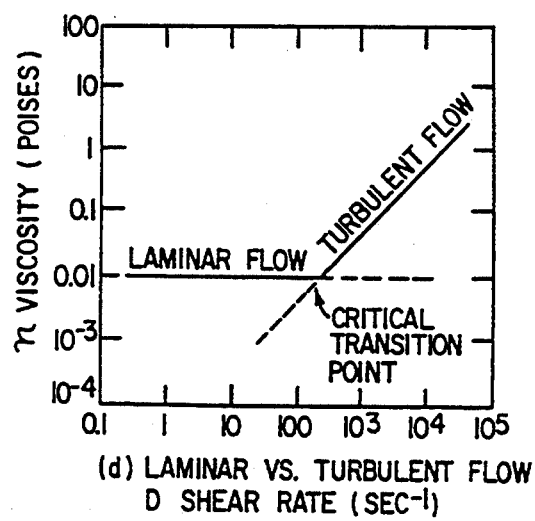

FIG. 10 is a graph relating the contact angle over a smooth solid surface as a function of $\theta$ and i that apply respectively, to adhesion (i cos $\theta$ + 1), penetration (i cos $\theta$), and spreading (i cos $\theta$ − 1).

Regions of adhesion versus abhesion, penetration versus repellency, and spreading versus retraction are shown by shaded areas. FIG. 10 illustrates what is theorized to be the relationship of a silicone polyer composition impregnant to silicone polymer composition solids in a treated web as regards such factors as adhesion, penetration, spreading, and retraction.

FIG. 11, consisting of FIGS. 11a through 11d, shows representative viscosity profiles plotted on log viscosity versus log shear rate graphs for (a) pseudoplastic flow, (b) distant flow, (c) pseudoplastic flow with superimposed thixotropic behavior, and (d) laminar Newtonian flow that erupts into turbulent flow at a critical transition point.

FIGS. 11a through 11d show a broad range of illustrative flow characteristics that could be demonstrated by silicone polymer composition impregnants suitable for use in this invention using pressured impregnation of a web as taught herein.

For purposes of this invention, the term "wetting" is used to designate such processes as adhesion, penetration, spreading, and cohesion. If wetting transpires as a spontaneous process, then adhesion and penetration are assured when the solid surface tension exceeds the liquid surface tension. Surface roughness promotes these spontaneous wetting actions. On the other hand, no such generalizations can be made when the solid surface tension is less than the liquid surface tension.

Surface tension is measured as by S.T.L. units for liquid and by S.T.S. units for solids; both units are dyns/centimeter. When S.T.S. is less than S.T.L., then wetting is less ubiquitous and prediction of wetting behavior is more difficult. However, by taking advantage of the liquid/solid contact angle that forms when a liquid retracts over a solid, it is possible to calculate with reasonable accuracy the wetting behavior that can be expected. The reduction in liquid surface area can be computed in terms of the contact angle that the liquid makes with the solid surface. Contact angles are always measured in the liquid phase). There is a point of equilibrium where the surface tension forces become balanced.

By measuring the contact angle of a liquid on a solid, the wetting behavior of the liquid impregnant can be measured.

The following examples are offered to specifically illustrate this invention. These examples are not to be construed as limiting the scope thereof, however.

EXAMPLE 1

Liquid Silicone Polymer Preparation 100 parts by weight of the curable liquid silicone polymer available commercially from Mobay as "Silopren ® LSR 2530" was mixed in a 1:1 ratio, as recommended by the manufacturer. A Hockmayer F dispersion blade at low torque and high shear was used to do the mixing. To this mixture were added 5 parts by weight of BSF "Uvinul 400" and 5/10 parts by weight Dow Corning 7127 accelerator, believed to be a polysiloxane but containing an undisclosed active accelerated ingredient.

EXAMPLES 2-19

Liquid Silicone Polymer Preparation

The procedure of Example 1 was repeated with various other curable viscous liquid silicone polymer composition commercially available. To this product system is added a substituted benzophenone and other additives, the result of which are shown in Table VII below. All parts are by weight.

TABLE VI

Illustrative Silicone Resin Compositions

| Example # | Starting Silicone Resin | Mixture Ratio of Packaged Components[1] | Substituted Benzophenone Name | Parts | Other Additives Name | Parts |
|---|---|---|---|---|---|---|
| 1 | Silopren ® LSR 2530 | 1:1 | Uvinul 400 | 5 | 7127 Accelerator | 5/10 |
| 2 | Silastic ® 595 LSR | 1:1 | Uvinul 400 | 5 | Syl-off ® 7611[2] | 50 |
| 3 | SLE 5100 Liquid BC-10 | 10:1 1:1 1:1 | Uvinul 400 | 5 | Sylox ® 2[3] | 8 |
| 4 | Silopren ® LSR 2530 | 1:1 | Uvinul 400 | 5 | Hydral ® 710[4] | 10 |
| 5 | Silopren ® LSR 2530 | 1:1 | Uvinul 400 | 5 | Silopren ® LSR Z3042[5] | 1 |
| 6 | SLE 5500 | 10:1 | Uvinul 400 | 5 | | |
| 7 | Silopren ® LSR 2540 | 1:1 | Uvinul 400 | 5 | | |
| 8 | SLE 5300 | 10:1 | Uvinul 400 | 5 | | |
| 9 | SLE 5106 | 10:1 | Uvinul 400 | 5 | | |
| 10 | Silopren ® LSR 2530 | 1:1 | Uvinul 400 | 5 | Flattening Agent OK412 ®[6] | 4 |
| 11 | Silopren ® LSR 2530 | 1:1 | Uvinul 400 | 5 | Nalco[5] 1SJ-612 Colloidal Silica[7] | 50 |
| 12 | Silopren ® LSR 2530 | 1:1 | Uvinul 400 | 5 | Nalco ® 1SJ-614 Colloidal Alumina[8] | |
| 13 | Silastic ® 595 LSR | 1:1 | Uvinul 400 | 5 | 200 Fluid[7] | 7 |
| 14 | Silopren ® LSR 2530 | 1:1 | Uvinul 400 | 5 | | |
| 15 | Silastic ® 595 LSR | 1:1 | Uvinul 400 | 5 | Zepel ® 7040[10] | 3 |
| 16 | Silastic ® 595 LSR | 1:1 | Uvinul 400 | 5 | Zonyl ® UR[11] | 1/10 |
| 17 | Silastic ® 595 LSR | 1:1 | Uvinul 400 | 5 | Zonyl ® FSN-100[12] | 1/10 |
| 18 | Silopren ® LSR 2530 | 1:1 | Uvinul 400 | 5 | DLX-600 ®[13] | 5 |
| 19 | Silopren ® LSR 2530 | 1:1 | Uvinul 400 | 5 | TE-3608 ®[14] | 5 |

Table VI Footnotes:
[1] Ratio listed is that recommended by the manufacturer.
[2] Syl-off ® (registered trademark of Dow Corning) is a cross-linker.
[3] Sylox ® 2 (registered trademark of W.R. Grace & Co.) is a synthetic amorphous silica.
[4] Hydral ® 710 (registered trademark of Alcoa) is a hydrated aluminum oxide.
[5] Silopren ® LSR Z/3042 (registered trademark of Mobay) is a silicone primer (bonding agent) mixture.
[6] Flattening Agent OK412 ® (registered trademark of Degussa Corp.) is a wax coated silicon dioxide.
[7] Nalco ® 1SJ-612 Colloidal Silica (registered trademark of Nalco Chemical Company) is an aqueous solution of silica and alumina.
[8] Nalco ® 1SJ-614 Colloidal Alumina (registered trademark of Nalco Chemical Company) is an aqueous colloidal alumina dispersion.
[9] 200 Fluid (registered trademark of Dow Corning) is a 100 centistoke viscosity dimethylpolysiloxane.
[10] Zepel ® 7040 (registered trademark of dupont) is a nonionic fluoropolymer.
[11] Zonyl ® UR (registered trademark of dupont) is an anionic fluorosurfactant.
[12] Zonyl ® FSN-100 (registered trademark of duPont) is a nonionic fluorosurfactant.
[13] DLX-6000 ® (registered trademark of dupont) is a polytetrafluoroethylene micropowder.
[14] TE-3608 ® (registered trademark of dupont) is a polytetrafluoroethylene micropowder.

EXAMPLE 20

Internally Coated, Fiber Encapsulated, Interstice Filled Fabric Preparation

A complete, stepwise, application of the inventive method in the production of an encapsulated-fiber fabric was as follows.

The selected base fabric was TACTEL ® (gold color) #612071 available from ICI Americas, Inc. through their agent, Arthur Kahn, Inc. This fabric was 100% woven nylon. If desired, this and other fabrics may be calendered to modify surface texture.

The fabric was weighed and measured. Its initial weight is 3.1 ounces per square yard. Its thickness equals 9 mils.

The fabric was next washed with detergent, rinsed thoroughly, and hung to air dry.

The fabric was soaked in water, wrung dry, and weighed. The water retained was equal to 0.8 g water/g fabric.

The fabric was then treated with a water repellant fluorochemical, a 2% solution by weight of Zepel ® 7040. In order to do so the fabric must be soaked in a 2.5% solution of Zepel ® water-repellant chemical in distilled water. This was because $$\frac{1 \text{ g fabric } (.02)}{0.8 \text{ g water}} = 0.025$$

The treated fabric was then run through a wringer and air dried.

Next, the fabric was heated in an oven for 1 minute at 350° F. This heating sinters the water repellant fluorochemical. The fabric with its fluorochemical residue is then run as in the preferred production embodiment, FIG. 7, in a vertical configuration and is described below. The fabric is run from a roll that incorporates significant braking or clutching to initiate the tension required for controlled material alignment and coating during application. The fabric web travels through a series of idler rolls ending at the application trough. As it passes the application trough, it picks up a thin coating of silicone impregnant and then moves under a shear blade that is parallel to the floor. The silicone impregnant is applied at 1.0 oz/sq. yd. and continues under a flex blade that is also parallel to the floor.

Multiple process stages of running the fabric with applied impregnant under the blades are preferably made. The multiple process stages are important, and are normally necessary. The impregnant is Mobay 2530 A/B in a 1:1 ratio and can be considered to be a viscoelastic liquid that flows only under the shear forces resulting from the pressured impregnation. The impregnant is believed to return very substantially to its original viscous condition almost immediately upon release of the pressure. The impregnant was believed to flow a short distance within the matrix of the fabric during the short time that it was, because of pressure shearing forces, of lowered viscosity. Therefore, a number of "flows" may be usefully generated in a number of passes in order to properly distribute the impregnant in its preferred position substantially encapsulating the surfaces of the fabric's fibers.

Finally, the impregnated fabric was run through a line oven, of approximately 10 yards in length, at 4–6 yards per minute, and was cured at 325°–350° F. It then passes through a series of idler rollers and is rolled up on a take-up roll, completing the tension zone. The resultant fabric has a non-tacky thin film of silicone that was internally coated to form a fiber encapsulated, interstice-filled fabric.

EXAMPLE 21

Evaluation of Fiber Encapsulated Fabric Properties

The test results of the original versus the produced fiber encapsulated fabric of Example 20 were as follows:

| Fabric | Original Fabric | Encapsulated |
|---|---|---|
| Spray Rating (1) | 20 | 100 (reverse = 100) |
| Rain Test (2) | Fail | Pass |
| Abrasion Test (cycles) (3) | 1,800 | 3,200 |
| Moisture Penetration (4) | Saturated | 0.0 g |
| Hydrostatic Resistance (psi) (5) | 1 | 2 |
| MVTR (g/m²/day)* (6) | 4,414 | 2,362 |
| Weight (oz/yd²) | 3.1 | 4.1 |

Amount Impregnated = 1.4 oz/yd²

*Environmental chamber at 104° F. and 74% humidity.

| Laundering Test (7) | Timer Washed | | | |
|---|---|---|---|---|
| (spray ratings) | Initial | 5× | 10× | 15× |
| impregnated side | 100 | 90 | 90 | 90 |
| reverse side | 100 | 90 | 90 | 90 |
| unimpregnated treated fabric | 100 | 80 | 80 | 40 |

Accelerated Weathering Test (8)

Samples placed in QUV weatherometer for 72 hours.

original = 7 impregnated side = 9 reverse side = 8

Footnotes:
(1) The spray test was conducted in accordance with AATCC 22-1974. It measures water repellency of a fabric sample on a scale of 0–100, with a reading of 100 designating a completely water repellent fabric.
(2) The rain test was conducted in accordance with AATCC 35-1985. It measures resistance of a fabric sample to penetration of water under static pressure from a shower head of 3 feet/5 minutes. A fabric is stormproof when less than 1.0 gram of water is absorbed by a standardized blotter used in the test.
(3) The abrasion test was conducted in accordance with Fed. Test Method Std. 191 A, Method 5306. Abrasion resistance is measured by mounting a fabric sample on a Taber Abraser Model 174 and measuring the number of cycles before the fabric begins tearing apart.
(4) The hydrostatic resistance test was conducted in accord with Fed. Test Method Std. 191A, Method 5512. The test measures a fabric sample's resistance to water under pressure using the Mullen's Burst Test apparatus. Test results are expressed in pounds per square inch at which water beads penetrate the fabric.
(5) The moisture vapor transmission (MVTR) test was conducted in accordance with ASTM E96-B. The test measures the amount of moisture vapor passing through a fabric sample in a controlled environment during a 24 hour period. The obtained MVTR figure is expressed in grams of water/square meter of surface/24 hour day. The environmental chamber was held at 104° F. and 47% humidity.
(6) The moisture vapor transmission (MVTR) test was conducted in accordance with ASTM E96-B. The test measures the amount of moisture vapor passing through a fabric sample in a controlled environment during a 24 hour period. The obtained MVTR figure is expressed in grams of water/square meter of surface/24 hour day. The environmental chamber was held at 104° F. and 47% humidity.
(7) A laundering test of the conventional household type was performed. Fabric samples were washed with Tide ® detergent. There was no drying. A spray test was subsequently carried out after each wash to determine the effect of the washing.
(8) The accelerated weathering test was conducted in accordance with ASTM G-53. Samples of original and impregnated fabrics were placed in the weatherometer of QUV Company and results were compared. (All readings were based on a graduated color scale of 0–20; 10 designated the original color, while 0 designated a white out).

EXAMPLE 22

Figure 3A:
FIG. 3a is a photomicrograph of a fabric of the invention magnified 120 times.
Figure 3B:
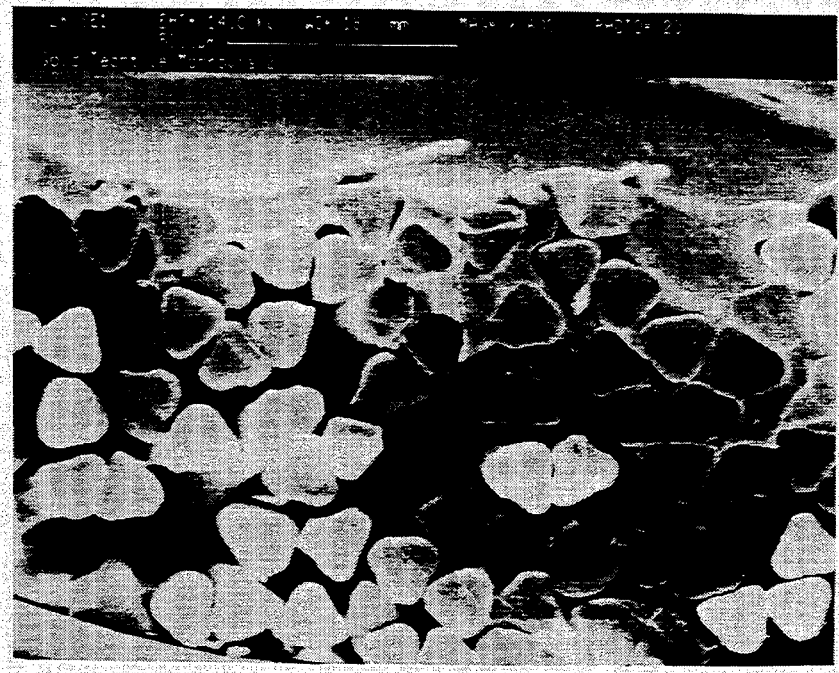
FIG. 3b is a cross section of a fiber bundle fabric of FIG. 3a magnified 600 times.
Figure 3C:
FIG. 3c is a view of the side of the fabric of FIG. 3a that is the opposite of the side to which silicone polymer was applied.

Description of Fabric Impregnation Through Scanning Electron Microscope Photomicrographs FIGS. 3a, 3b and 3c were taken using a Cambridge 360 scanning electron microscope. The samples were cut using teflon coated razor blades, mounted on ½ inch diameter aluminum stubs, and coated with a gold/palladium alloy.

FIG. 3a is a photomicrograph of the gold color Tactel fabric described in Example 20. The surface of the material has been magnified 120 times and shows that the cured silicone polymer impregnant is present as a thin film, or coating, or layer within the material and envelopes at least a portion of the fibers. The fiber bundles are somewhat distinguishable in the weave, but each filament in the fiber bundles is not individually distinct.

The sample in FIG. 3b has been magnified 600 times and shows the cross-section of a fiber bundle from the same Gold Tactel in FIG. 3a. The cured silicone polymer impregnant envelopes at least a portion of the fibers. The interstices or void areas between filaments in the region of the internal coating are mostly filled or plugged by such impregnant. However, the web remains breathable and because of the impregnant barrier is either water resistant or waterproof.

FIG. 3c is the side of the fabric in FIG. 1 opposite from which the silicone polymer impregnant was applied. The silicone polymer impregnant is most readily apparent at the fiber bundle interstices and not visible in the fiber bundles themselves.

EXAMPLE 23

Fiber Enveloped Fabric Preparation

The selected base fabric was Arthur Kahn TAC-TEL ® (hot coral) #70146. This fabric is 100% nylon.

The fabric was pretreated at Cal-Pacific (a commercial finisher of fabrics) with dupont ZEPEL ® 6700.

The impregnant composition is Mobay LSR 2530 A/B in a 1:1 ratio=5% UVINUL ® 400 (5% of total weight of Mobay LSR).

Impregnation of this composition was performed in a three stage continuous process using equipment as shown in FIG. 7 consisting of the following procedure:

The composition was applied to the fabric at (a) a pressure of 3 lbs/linear inch, utilizing (b) a shear (bar) knife at a high pressure, and at a 90° angle to the fabric (the edge of the knife is milled sharp). The rate of application is at approximately 1.0 oz/sq yd.

A flex knife was then applied at a 45° angle with the recovery system utilizing gravity.

For both (a) and (b) above, the microweb pressure was applied at a low web speed on a roller system varied at from about 260–400 yards per hour.

Next, the fabric is cured using an upper oven (lower oven turned off) at a temperature of about 320°–330° F. The fabric was in the oven for approximately 3 to 4 minutes. The impregnant cures to a non-tacky thin film, as in the previous example.

EXAMPLE 24

Prior Art Silicone Polymer Treated Fabric

Figure 2:
FIG. 2 is a plan view of a prior art silicone polymer treated fabric magnified 150 times.

The fabric resulting from a prior art application of a viscous liquid curable silicone polymer composition is shown in FIG. 2. The photographic view of FIG. 2 is at 150× magnification. It shows a polyester and cotton cloth blend into which Dow Corning 590 LSR silicone polymer composition has been coated by a procedure of the prior art. The fabric side shown in FIG. 2 is the top, or treatment, side, which was the fabric side upon which coating was accomplished.

As shown by the example of the treated fabric of FIG. 2, the prior art impregnated fabric is characterized by a high degree of disorder. A large number of particulates (typical) appear to litter the surface of the fabric. A substantial portion of the area of the surface, which appears to be a solid layer, is silicone polymer composition. Certain yarn fragments can be observed to protrude through the surface of this silicone polymer composition. Additionally, the silicone polymer composition on either the polyester or the cotton fibers is not an encapsulation layer, but rather a matrix with the coated fibers being in general disarray, probably from forces occurring during the indicated prior art silicone polymer composition application procedure. Although silicone polymer composition is present upon the yarn or fiber surfaces of the substrate, and certainly is present as a layer upon the exterior surface of the three-dimensional fabric body, the silicone polymer composition has not controllably and individually encapsulated the fibers and left the interstices between fibers largely devoid of such polymer. In the prior art, a placement of silicone polymer composition in a fabric is not controlled to such a degree so as to produce a product in accordance with the present invention.

EXAMPLE 25

Figure 13A:
FIGS. 13a through 13c are scanning electron microscope photomicrographs of another representative fabric of the present invention.
Figure 13B:
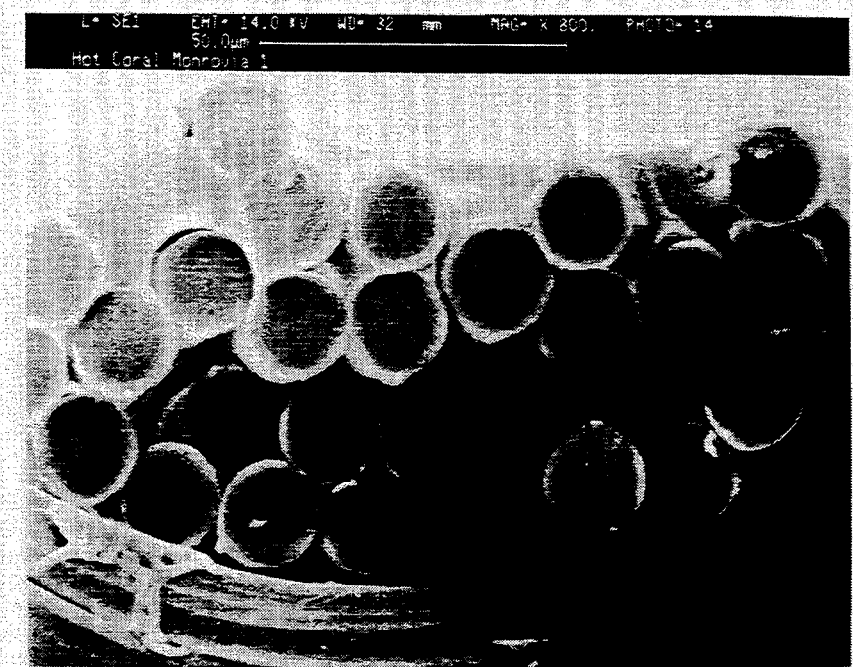
Figure 13C:
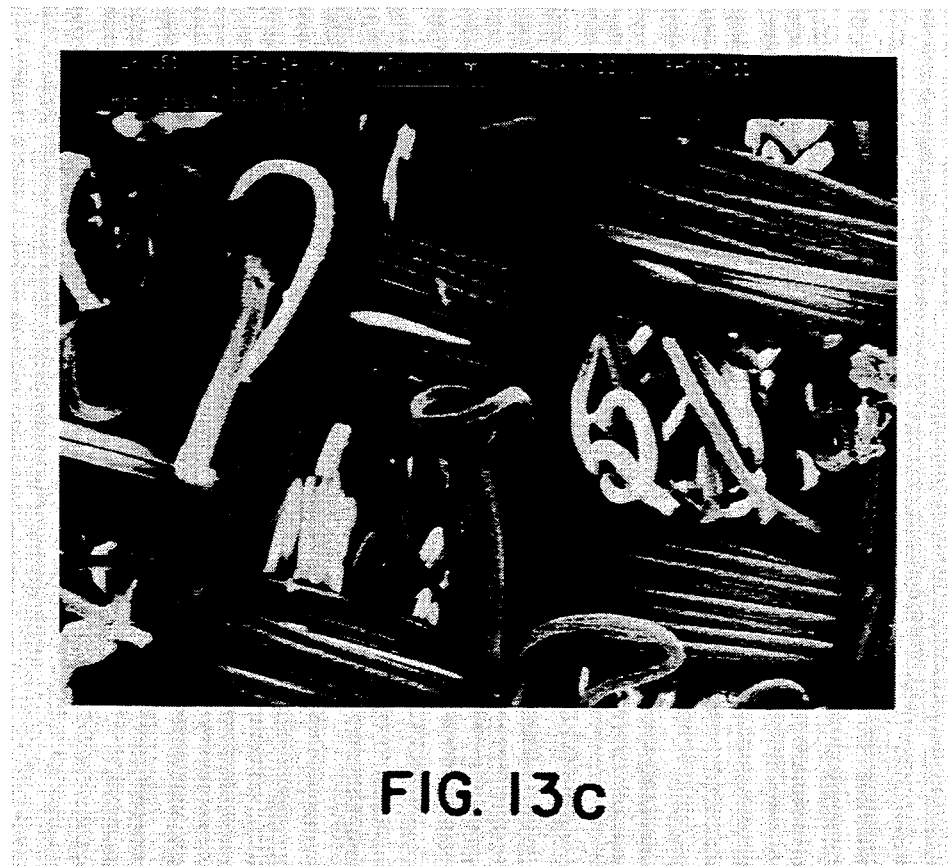

Description of Fabric Impregnation Through Scanning Electron Microscope Photomicrographs FIGS. 13a, 13b and 13c were taken using a Cambridge 360 scanning electron microscope. The samples are cut using teflon coated razor blades, mounted on ½ inch diameter aluminum stubs, and coated with a gold-/palladium alloy.

FIG. 13a is a photomicrograph of the Tactel (hot coral) fabric described in Example 23. The surface of the material has been magnified 120 times and shows that the cured silicone polymer impregnant is present as a thin film, or coating, or layer within the material and envelopes at least a portion of the fibers. The fiber bundles are somewhat distinguishable in the weave, but each filament in the fiber bundles is not individually distinct.

The sample in FIG. 13b has been magnified 800 times and shows the cross-section of a fiber bundle from the same Tactel in FIG. 13a. The cured silicone polymer impregnant envelopes at least a portion of the fibers. The interstices or void areas between filaments in the region of the internal coating are mostly filled or plugged by such impregnant. However, the web remains breathable and because of the impregnant barrier is either water resistant or waterproof.

FIG. 13c is the side of the fabric in FIG. 1 opposite from which the silicone polymer impregnant was applied. The silicone polymer impregnant is most readily apparent at the fiber bundle interstices and not visible in the fiber bundles themselves.

In the next examples that involve accelerated weathering, abrasion, water repellency, moisture penetration, and rain testing, data is provided for a Tactel fabric identified as Deva Blue. The fabric is 100% nylon, available from Arthur Kahn and identical in composition, preparation, and enveloping specification to that of the Hot Coral presented in previous examples.

EXAMPLE 26

Accelerated Weathering Test

The results of weathering upon a treated web of this invention are shown in actual tested sample pieces comparing original fabrics with embodiments of the enveloped fiber fabrics of this invention.

In every case, the enveloped fiber fabric samples were found to have significantly better weathering characteristics than the original untreated fabrics as determined by accelerated weathering tests. Even the reverse side (compared to the treated side) of an enveloped fiber nylon fabric of the Tactel ® type was improved over the original fabric. In addition, the excellent "hand" of the enveloped fiber fabric was found to have been maintained after the accelerated weathering test.

The test performed conforms to each of the following performance standards:

ASTM G-53 light/water exposure-materials
ASTM D-4329 light/water exposure-plastics
General Motors Test spec TM-58-10
ISO 4892 Plastics exposure to lab light The procedure used for the accelerated weathering testing involved subjecting fabric samples to four hours of high-intensity ultraviolet light, alternating continuously with four hours of water condensation wetting the fabric in the dark. This alternating exposure (four hours on, four hours off) to high-intensity ultraviolet light and water wetting simulates outdoor environmental conditions in a vastly accelerated manner, quickly degrading unprotected dyes and fibers.

The apparatus used for this test was a QUV Accelerated Weathering Tester from The Q-Panel Company, 26200 First Street, Cleveland, Ohio 44145.

The results obtained on some sample fabrics are expressed in the following Table. In this Table, results are expressed in the form of "A/B" where A and B are numbers. The number "A" is the color rating on a graduated scale from 0 to 10. The number 10 equals perfect (original) condition where 0 equals a white color and a completely faded fabric. The number "B" is the number of hours of weathering transpiring when the number "A" rating was obtained.

TABLE X

Accelerated Weathering Testing

| Original Fabric | Original Fabric Weathered | Enveloped Fabric Weathered | Reverse Side Weathered | Color Rating (Rating/Hours) 10 = Perfect 0 = White Color Fades Out |
|---|---|---|---|---|
| 1. TACTEL ® Deva Blue 9-420-6-1 | | | | |
| 10/0 | 3/159 | 8/159 | | After 159 hrs., enveloped fabric significantly less weathered than original; original nearly white; enveloped fabric still light blue. |
| 2. TACTEL ® Hot Coral 9-420-6-2 (AKA 18) | | | | |
| 10/0 | 5/24 | 10/24 | 9/24 | After 24 hrs., enveloped fabric is significantly less weathered than original, as was reverse side. |

EXAMPLE 27

Abrasion Resistance Testing

The results of abrasion resisting testing clearly show that enveloped fiber fabrics of this invention have superior wear characteristics compared to the untreated original (starting) fabrics. In most cases, the enveloped fiber fabric samples underwent twice as many cycles as the untreated samples without evidencing tearing in the samples. Such results can be explained by theorizing that the envelopment with silicone polymer of the yarns and fibers comprising a fabric, provides such treated yarns and fibers with a lubricity agent so that abrasive action was minimized and the integrity of the fabric was preserved significantly longer. The anti-abrasion character also applied to the minimized effects of one fiber rubbing against another fiber, or of one yarn against another yarn.

This experiment compared the abrasion resistance of embodiments of the enveloped fiber fabrics of this invention with untreated fabrics.

The durability of each fabric test specimen was determined by the Taber Abraser. Each specimen is abraded for the number of cycles indicated. Comparisons were then made between the enveloped fiber fabrics of the invention and untreated fabrics.

Specifically, this test method utilizes the Taber Abraser No. 174. An important feature of this abrader was that its wheels traverse a complete circle on the test specimen surface. Thus, the surface was abraded at all possible angles relative to the weave or grain of the specimen. Comparisons of the enveloped fiber fabric to the untreated fabric were based upon a scale 0 through 10, where 0 was a completely torn specimen, and 10 was the new (or starting) sample.

Each test procedure used a single 7 inch diameter fiber enveloped fabric specimen, and a single 7 inch diameter original (untreated) fabric specimen. The procedure used was as follows:

1. A test specimen of the fiber enveloped fabric with a 7 inch diameter was cut.
2. An equally-sized specimen of control (untreated) fabric was cut.
3. The fabric specimen was mounted on the rotating wheel securely and the clamps were screwed down.
4. The counter was set.
5. The vacuum power adjustment was set. (For this experiment, vacuum was set at 80.)
6. The abraser was started.
7. At the procedurally specified number of revolutions, the abraser was stopped and each fabric sample was rated at a value between 0 and 10.

Illustrative results of the test on some sample fabrics are shown in the following Table:

| | Abrasion Testing | | |
|---|---|---|---|
| | Numeric Grade of Abrasion 0-10 | | |
| | 0 - Total failure of fabric specimen. Fibers are torn apart. | | |
| | 5 - Fabric specimen is starting to tear. Fabric is noticeably thinner. | | |
| | 10 - Original unabraded fabric specimen. | | |
| SPECIMENS | UNTREATED FABRIC | ENCAPSULATED FABRIC | COMMENTS |
| Hot Coral Tactel | 5 1000 cyc. | 7 1000 cyc. | Untreated sample is starting to tear, and enveloped sample was still intact. |
| Deva Blue Tactel | 4 1000 cyc. | 7 1000 cyc. | Visible rips in untreated sample. Enveloped sample fibers were frayed. |

EXAMPLE 28

Breathability Testing

This test procedure followed the Modified ASTM E96-B test.

As shown by the results of this testing in the following Table, the fiber enveloped fabrics of this invention were found to have high breathability. This breathability was in excess of that needed to remove the average value of several thousand grams of perspiration generated daily by the human body. The results for the fiber enveloped fabrics of this invention were generally superior to the corresponding results measured under the same conditions for prior art treated fabrics, such as Gore-Tex ® brand fabric.

Breathability of a fabric sample was determined by accurately weighing the amount of water passing through such fabric sample under carefully controlled temperature and relative humidity conditions in an environmental chamber. The water weight loss from a cup whose mouth is sealed with a fabric sample was expressed as grams of water vapor per square meter of fabric per 24 hour day.

In an attempt to more realistically simulate what is actually occurring inside apparel during exercise, a specially designed test was performed to measure outward water vapor transport (MVTR) in a "Bellows" effect. The test simulates the high volumes of moisture and air that mix within a garment that pass outward through it as air is drawn in resultant from activity. The enveloped fabrics of this invention were found to provide increased performance at higher activity, or air exchange level than is achievable with corresponding untreated fabrics.

The "Bellows" MVTR breathability test was run inside of a controlled temperature/humidity chamber similar to the foregoing cup test. However, instead of a standard cup, each fabric sample was sealed over the open top of a special cup which was provided with an air inlet aperture in its bottom, thereby allowing air to be bubbled up through the sealed container at a controlled rate. A check valve at the air inlet operation prevents backup or loss of water from the container. The air bubbles passed upwardly through the water and out through the fabric sample mounted sealingly across the cup top along with the water vapor. The following Table illustrates some representation results obtained.

TABLE

| Fabric | Moisture Vapor Transport (MVTR) MVTR[1] |
|---|---|
| Made by a method of the invention | |
| Enveloped fiber fabric, Hot Coral Tactel ® | 13,600 |
| Commerical Products | |
| Gore-Tex 3-ply fabric | 10,711 |

Table Footnote:
[1]MVTR here references moisture vapor transport through a fabric sample as measured by the "Bellows" test with air delivered to the bubbler at 2 to 4 psi air pressure, in an Environmental Chamber at 100 to 102° F. and 38–42% relative humidity. MVTR is expressed as grams of water per square meter of surface per 24 hour day.

EXAMPLE 29

Water Repellency: Spray Testing

Water repellency spray testing is carried out according to AATEC Test Method 22-1974.

The results of such testing show that the fiber enveloped Tactel ®-type fabrics of the invention show excellent initial spray ratings initially, as do the original untreated fabrics which have been treated with water repellent chemicals such as fluorochemicals. Specifically, as the results shown below demonstrate, after ten machine washes, the treated side of a fiber enveloped fabric of the invention was found to remain highly water repellent, while, on the reverse side thereof, the original water repellency rating was found to have fallen significantly. The water repellency spray rating on the untreated fabric fell even more drastically. Excellent "hand" was retained after the test. It is believed that pretreatment with a fluorochemical having good water repellent properties can augment and even synergistically coact with the silicone resin used to produce fiber enveloped fabrics of this invention to produce superior spray ratings in such a fiber. The results are shown in the following Table.

This test method is believed to be applicable to any textile fabric, whether or not it has been given a water resistant or water-repellent finish. The purpose of the test is to measure the resistance of fabrics to wetting by measuring the water-repellent efficiency of finishes applied to fabrics, particularly to plain woven fabrics. The portability and simplicity of the instrument, and the shortness and simplicity of the test procedure, make this method of test especially suitable for mill production control work. This test method is not intended, however, for use in predicting the probable rain penetration resistance of fabrics, since it does not measure penetration of water through the fabric.

The results obtained with this test method are believed to depend primarily on the resistance to wetting, or the water repellency, of the fibers and yarns comprising a fabric, and not upon the construction of the fabric.

This test involves spraying water against the taut surface of a test fabric specimen under controlled conditions which produce a wetted pattern whose size depends on the relative water repellency of the fabric. Evaluation is accomplished by comparing the wetted pattern with pictures on a standard chart.

The apparatus and materials employed for this test were an AATCC Spray Tester, a beaker, distilled water, and the specimen fabrics.

The procedure followed for this test was as follows: a test specimen, which had been conditioned as procedurally directed, was fastened securely in a 15.2 cm (6") metal hoop so that it presented a smooth wrinkle-free surface. The hoop was then placed on the stand of the tester so that the fabric was uppermost in such a position that the center of the spray pattern coincided with the center of the hoop. In the case of twills, gabardines, piques or fabrics of similar ribbed construction, the hoop was placed on the stand in such a way that the ribs were diagonal to the flow of water running off the fabric specimen.

250 milliliters (ml) of distilled water at 27° C.±1° C. (80° F.±2° F.) was poured into the funnel of the tester and allowed to spray onto the test specimen, which took approximately 25 to 30 seconds. Upon completion of the spraying period, the hoop was taken by one edge and the opposite edge tapped smartly once against a solid object, with the fabric facing the object. The hoop was then rotated 180 degrees and then tapped once more on the location previously held.

The procedure and apparatus of this test were slightly modified from the specifications, as follows:
1. The spray nozzle holes were slightly larger than specified, but the flow rate of the nozzle was 250 ml/30 sec., as required.
2. The number of taps of the hoop was two instead of one.

For each wash test, a fabric sample was washed using a warm wash/cold rinse cycle with one cup of Tide ® detergent and dried at a hot/dry cycle in a dryer, unless otherwise indicated.

The test results were evaluated by comparing the wet or spotted pattern on the fabric sample after tapping the hoop with the standard rating chart. Results produced surface wetting, with no water completely soaking through the test fabric sample. The numbers were ratings based upon the standard chart. Such values are thus subjective deductions by an experienced experimenter.

TABLE

| | SPRAY TEST RESULTS | | | | | | | |
|---|---|---|---|---|---|---|---|---|
| | ENVELOPED-FIBER FABRIC OF THE INVENTION | | | | | | | |
| ORIGINAL FABRIC | | | Initial | | After 5 Washes | | After 10 Washes | |
| Tactel ® Color & Number | Initial | After 4 Washes | Enveloped Side | Reverse Side | Enveloped Side | Reverse Side | Enveloped Side | Reverse Side |
| Deva Blue 9-420-6-1 | 100 | 10 | 90 | 100 | 90 | 70 | 80 | 50 |
| Hot Coral 9-420-6-2 | 100 | 30 | 90 | 100 | 70 | 55 | 70 | 30 |
| Gold Tactel 8-100-1 | 100 | 100 | 90 | 90 | 90 | 90 | 90 | 80 |

EXAMPLE 30

Moisture Penetration Test

The results shown in the Table below demonstrate that all of the fiber enveloped fabrics of this invention test were significantly better than the original untreated fabrics with regard to resisting the penetration of water under the test conditions used. After the test, the "hand" of the tested fabric samples remained excellent.

The purpose of this test was to evaluate how well a fabric stands up to wetness under continuous pressure, such as kneeling on wet ground, or sitting in a wet chairlift, for a period of 30 minutes.

This test involves placing both a fabric sample and a standard blotter sample on top of a water container which contains 700 ml of tap water. The fabric sample and the blotter sample are each then subjected to a continuous pressure of 87 lbs. distributed evenly over 100 square inches of surface area for a period of 30 minutes. After this time, a visual inspection of the fabric is made for any water penetration, and the paper blotter is weighed to detect water gain or penetration.

The apparatus employed for each such test was one 20 inch diameter aluminum pan, one 87 lb weight distributed evenly over 100 square inches of fabric, one paper blotter, 700 ml water, miscellaneous fabric scraps for cushioning and the test fabric sample pieces.

| Paper blotter dry weight: | 4.7 gm |
|---|---|
| Total weight applied to fabric: | 87 lbs. |
| Pressure evenly distributed over surface area of | 100 sq. in. |

$$\text{Pressure} = \frac{87 \text{ lbs.}}{100 \text{ sq. in.}} = 0.87 \text{ lbs./sq. in.}$$

The procedure observed for this test was as follows:
1. 700 ml tap water was placed in the round pan.
2. The fabric sample was placed with one side facing the water.
3. One piece of dry blotter paper was placed over the fabric to cover the pan.
4. Scrap fabric was placed over the blotter paper to cushion the weight.
5. The 87 lb. weight was distributed evenly over the 100-square-inch area.
6. This assembly was left undisturbed for 30 minutes.
7. After this time period, the visual results were recorded.

TABLE

| FIBER ENVELOPED FABRIC OF THE INVENTION | | | |
|---|---|---|---|
| Fabric Sample and Thickness | Enveloped Side of Fabric Facing Water | Non-Enveloped Side of Fabric Facing Water | Control Fabric |
| Deva Blue Tactel ® 0.009 microns | No water penetration through the fabric. No visible water spots. Paper weight = 4.7 gm Water gain = 0.0 gm | No water penetration through the fabric. No visible water spots. Paper weight = 4.7 gm Water gain = 0.0 gm | Failure - total saturation of fabric and blotter. |

EXAMPLE 31

Rain Test

In this testing, the rain test procedure of AATCC Method 35-1985 was followed.

The rain test results obtained demonstrate the clear superiority of the fiber enveloped fabric of the present invention as compared to the original untreated fabric. The data in the Table below shows that fiber enveloped fabrics pass this test by allowing virtually no water to pass therethrough. This result is comparable to the results obtained with higher cost so-called breathable waterproof fabrics currently commercially available in the market. In contrast, the original, untreated fabrics fail to pass this test because they demonstrate complete saturation. The fiber enveloped fabric samples retain excellent "hand" after the test.

The purpose and scope of this ASTM test is to evaluate resistance of a fiber enveloped fabric to water under simulated storm conditions. The test specifies that a test fabric is stormproof if less than one gram of water is absorbed by blotter paper with a shower head pressure of 3 feet exerted for 5 minutes. This test method is applicable to any textile fabric, whether or not it has a water repellent finish. It measures the resistance of a fabric to the penetration of water by impact, and thus can be used to predict the probable rain penetration resistance of a fabric. The results obtained with this method of test depend on the water repellency of the fibers and yarns in the fabric tested, and on the construction of the fabric.

This test involves a test specimen backed by a pre-weighed standard blotter. The assembly is sprayed with water for 5 minutes under controlled conditions. The blotter then is separated and weighed to determine the amount of water, if any, which has leaked through the specimen fabric during the test and has been absorbed by the blotter.

The apparatus and materials employed in each test were a modified rain tester, blotter paper, water at 80° F.±2° F., a laboratory balance, 8"×8" fabric specimens which had been pre-conditioned in an atmosphere of 65% (±2%) relative humidity and 70° F. (±2° F.) for four hours before testing, and tape.

The procedure followed for this test was as follows:
1. A 6"×6" paper blotter was weighed to the nearest 0.1 gm and placed behind the test specimen.
2. The test fabric with the paper blotter in registration therewith was taped on the specimen holder.
3. A tube in the rain tester was filled with water up to the 3 foot level. It was confirmed that water was flowing out of the overflow tube which maintains the 3 foot column of water.
4. The water spray distance from the tip of the nozzle to the specimen holder was measured and adjusted to 12 inches.
5. The specimen holder was left in place and the rain tester was turned on for five minutes.
6. After the test period, the paper blotter was removed and reweighed to the nearest 0.1 gm.

The results of the test on selected fabric samples are shown in Table:

TABLE

| Fabric Sample | Original Not Washed | After 5 Machine Washes | After 10 Machine Washes |
|---|---|---|---|
| RAIN TEST: GRAMS OF WATER PENETRATING THE FABRIC | | | |
| Hot Coral Tactel ® | 0 | 0 | 0 |
| Deva Blue Tactel ® | 0 | 0 | 0 |
| Prior Art Treated Fabrics | | | |
| Ultrex ® | 0 | — | 0.1 |
| Gore-Tex ® | 0 | 0 | — |

Original Fabrics-Water Repellant Chemicals Only, No Encapsulation
　Hot Coral Tactel/Failed-saturated
　Deva Blue Tactel/Failed-saturated

EXAMPLE 32

Comprehensive Composite Measurement of Fiber Enveloped Fabric Performance

The preceding examples demonstrate the impressive performance of the fiber enveloped fabric of the fabric's invention in diverse areas. Yet, the results of each of these tests and performance capabilities expressed individually fails to capture the comprehensively enhanced range of performance capabilities of the fiber enveloped fabric of the invention. For example, the impregnation process of the this invention produces a fiber enveloped breathable waterproof fabric that produces equal, or superior, test results over a broad range of different performances at a lighter, more insubstantial fabric weight compared, for example, to the untreated fabric. In other words, less fabric can be used, or worn in the case of garments, in order to obtain equal or superior performance.

What is claimed is:
1. A flexible, porous substrate having a matrix with open cells therein, at least some of said cells being at least partially individually lined with a curable shear thinning thixotropic polymer composition, and at least some of said cells being open.
2. The substrate of claim 1 wherein said substrate is a leather.
3. The substrate of claim 1 wherein said substrate is a porous paper.
4. The substrate of claim 1 wherein said substrate is an open celled foamed plastic structure.
5. The substrate of claim 1 wherein said substrate is a synthetic leather.
6. The substrate of claim 1 wherein said substrate comprises a laminate comprising a layer of an open celled porous flexible material and a layer of a non-porous, flexible material.
7. The substrate of claim 1 wherein said polymer composition is from the group consisting of silicones, polyurethanes, fluorosilicones, modified polyurethane silicones, modified silicone polyurethanes, acrylics, and polytetrafluoroethylene.
8. The substrate of claim 1 which has been impregnated with a fluorochemical prior to treatment with the polymer composition.
9. The substrate of claim 8 wherein the fluorochemical is positioned on the surface of the lined cells.
10. The substrate of claim 8 wherein the quantity of said fluorochemical is in the range of about 0.01 to about 5 weight percent of the weight of untreated substrate.
11. The substrate of claim 10 wherein said polymer composition is cured and wherein the total weight of said fluorochemical and said polymer composition is in the range of about 5 to about 200 weight percent of the total weight of untreated substrate.
12. The substrate of claim 11 wherein said polymer composition contains a benzophenone.
13. The substrate of claim 1 wherein the composition includes a functional additive and said additive is positioned on the surface of the lined cells.
14. The substrate of claim 13 wherein the functional additive includes one or more additives from the group of reflective agents, mildew resistent agents, conductive agents, biocompatible proteins, hand altering agents, blood repellents, viscosity agents, rheology agents, flexibility agents, light fastness agents, rot resistent agents, stain resistent agents, grease resistent agents, ultraviolet absorbers, aluminum hydroxide, filling agents, flattening agents, electrical conductive agents, thermal conductive agents, flame retardants and radiation reflectivity agents.
15. The substrate of claim 1 wherein said polymer composition is silicone.
16. The substrate of claim 15 wherein said silicone polymer composition has an uncured liquid viscosity of at least about 1,000 and no more than about 2,000,000 centipoise.
17. The substrate of claim 15 wherein said silicone polymer is cured and elastomeric.
18. The substrate of claim 5 wherein the quantity of said silicone polymer composition is in the range of about 5 to about 200 weight percent of the weight of untreated substrate.
19. The substrate of claim 18 wherein said substrate is water resistant and rewashable.
20. A fluorochemical and shear thinning thixotropic resin treated porous substrate which is breathable, water resistant and rewashable comprising:
　(A) a tensionable porous substrate having opposed, substantially parallel surfaces and comprised of a matrix having open cells therein:
　(B) said substrate having been preliminarily generally uniformly impregnated with a fluorochemical; and

(C) said substrate having been thereafter impregnated under tension with a shear thinning thixotropic polymer composition that is present in amount in the range from about 5 to about 200 weight percent of the weight of the untreated substrate, with at least some of said cells remaining open.

21. The substrate of claim 20 wherein said substrate is also laterally tensionable.

22. The substrate of claim 20 wherein said substrate is leather.

23. The substrate of claim 20 wherein said substrate is a porous paper.

24. The substrate of claim 20 wherein said substrate is an open-celled plastic structure.

25. The substrate of claim 20 wherein said substrate is a synthetic leather.

26. The substrate of claim 20 wherein said substrate comprises a layer of an open celled, porous, flexible material and a layer of a non-porous flexible material.

27. The substrate of claim 20 which is characterized by having:
(A) a water drop contact angle in the range of about 90° to about 160°;
(B) a rewash capability of at least about 3;
(C) a breathability of at least about 35% of untreated substrate fabric; and
(D) a water repellency rating of at least about 80 prior to washing.

28. A flexible porous web which has an internally located coating that is comprised of a curable shear thinning thixotropic composition, said coating being positioned in an approximately planar region extending through the web in a direction generally parallel to and spaced from at least one major surface thereof, said web, upon curing the said curable composition thereof, being breathable and highly water repellent and exhibiting a hand and flexibility comparable to the hand and flexibility of an untreated web.

29. The web according to claim 28 wherein said composition is nonelastomeric.

30. The web of claim 28 wherein said composition is curable at room temperature.

31. The web of claim 28 wherein said composition comprises a thermoplastic material.

32. The web of claim 28 wherein the polymer composition is from the group consisting of silicones, polyurethanes, fluorosilicones, modified polyurethane silicones, modified silicone polyurethanes, acrylics, and polytetrafluoroethylene.

33. The web of claim 28 wherein the polymer composition includes an ultraviolet absorber.

34. The web of claim 28 wherein the polymer composition includes a flame retardant.

35. The web of claim 28 wherein the polymer composition includes aluminum hydroxide.

36. The web of claim 28 wherein the porous web has a plurality of structural elements which define a plurality of interstices between adjacent structural elements and wherein the structural elements between the planar region and said major surface are substantially enveloped by said shear thinning thixotropic composition and the interstices are substantially open.

37. The web of claim 36 wherein the shear thinning thixotropic composition includes one or more additives from the group of reflective agents, mildew resistent agents, conductive agents, biocompatible proteins, hand altering agents, blood repellents, viscosity agents, rheology agents, flexibility agents, light fastness agents, rot resistent agents, stain resistent agents, grease resistent agents, ultraviolet absorbers, aluminum hydroxide, filling agents, flattening agents, electrical conductive agents, thermal conductive agents, flame retardants and radiation reflectivity agents, and said additive or additives are positioned on the surface of the enveloped structural elements.

38. The web of claim 36 wherein the composition includes a functional additive, and said additive is positioned on the surface of the enveloped structural elements.

39. The web of claim 38 wherein the functional additive includes one or more additives from the group of reflective agents, mildew resistent agents, conductive agents, biocompatible proteins, hand altering agents, blood repellents, viscosity agents, rheology agents, flexibility agents, light fastness agents, rot resistent agents, stain resistent agents, grease resistent agents, ultraviolet absorbers, aluminum hydroxide, filling agents, flattening agents, electrical conductive agents, thermal conductive agents, flame retardants and radiation reflectivity agents.

40. A flexible porous web comprising a plurality of structural elements which define a plurality of interstices between adjacent structural elements, at least a portion of said structural elements being substantially enveloped by a curable shear thinning thixotropic polymeric composition in an approximately planar region extending through the web in a direction generally parallel to and spaced from at least one major surface of the web with at least some of said interstices being open, said web, upon curing the said curable composition thereof, being breathable and highly water repellent and exhibiting a hand and flexibility comparable to the hand and flexibility of an untreated web.

41. The web of claim 40 wherein said composition is non-elastomeric.

42. The web of claim 40 wherein said composition is curable at room temperature.

43. The web of claim 40 wherein said composition comprises a thermoplastic material.

44. The web of claim 40 wherein said composition is from the group consisting of silicones, polyurethanes, fluorosilicones, modified polyurethane silicones, modified silicone polyurethanes, acrylics, and polytetrafluoroethylene.

45. The web of claim 40 wherein the composition includes a functional additive, and said additive is positioned on the surface of the enveloped structural elements.

46. The web of claim 45 wherein the functional additive includes one or more additives from the group of reflective agents, mildew resistent agents, conductive agents, biocompatible proteins, hand altering agents, blood repellents, viscosity agents, rheology agents, flexibility agents, light fastness agents, rot resistent agents, stain resistent agents, grease resistent agents, ultraviolet absorbers, aluminum hydroxide, filling agents, flattening agents, electrical conductive agents, thermal conductive agents, flame retardants and radiation reflectivity agents, and said additive or additives are positioned on the surface of the enveloped structural members.

47. A method of controllably impregnating an impregnant into a web, the method comprising:
providing a web having a plurality of structural elements defining a plurality of interstices between adjacent structural elements;

saturating the web with a liquid saturant containing a water repellent chemical that has a capacity and a concentration sufficient to create a surface contact angle with water of greater than 90 degrees when within the web;

wherein the saturating leaves a residue of the water repellent chemical upon the structural elements of the web;

pressuring a shear thinning thixotropic impregnant that has a surface contact angle with the saturated web of greater than 70 degrees into the web to substantially envelop the structural elements while not substantially filling the web's interstices;

wherein the impregnant is facilitated to flow in the web and upon the structural elements by the residue of the water repellent chemical.

48. The method of claim 47 wherein the impregnant includes one or more additives that serve a functional purpose within the impregnated web and the method further includes the step of passing the impregnated web under tension into contact with one or more shear blades to position the additives on the surface of the enveloped structural elements.

49. The method according to claim 47 wherein the saturating comprises padding.

50. The method according to claim 47 which between the saturating and the pressuring further comprises sintering the water repellant chemical residue in situ within the web in order to cause it to flow upon the three-dimensional structure of the web and to become affixed within the three-dimensional structure of the web.

51. The method according to claim 47 wherein the saturating is with a liquid saturant containing fluorochemicals, thereby leaving a fluorochemical residue upon the three-dimensional structure of the web.

52. The method according to claim 51 wherein the saturating is with a liquid saturant containing a water repellant chemical that is perfluorinated.

53. The method according to claim 47 wherein the saturating is with a saturant containing a perfluorinated durable water repellant chemical consisting of polyperfluoroethylene.

54. The method according to claim 47 wherein the saturating further comprises calendering under pressure and heat to create at least one smooth side to the web.

55. The method according to claim 47 wherein the saturating is with a liquid saturant also containing a bonding agent as well as a water repellant chemical.

56. The method according to claim 47 that following the saturating further comprises fixing the water repellant chemical to the three dimensional structure of the web.

57. The method according to claim 56 wherein the fixing comprises sintering.

58. The method according to claim 47 that between the saturating and the pressuring further comprises adding diluents as required to the impregnant to decrease viscosity and adding solids as required to the impregnant to increase viscosity in order to adjust the viscosity of the impregnant to be within a range of 5,000–2,000,000 centipoise.

59. The method according to claim 58 wherein the adding of diluents and solids comprises adding substances that variously serve as diluents and solids that also serve an additional, functional, purpose within the impregnated web other than the purpose of viscosity adjustment.

60. The method according to claim 59 wherein the adding is of one or more substances having the additional functional purpose that are from the group consisting of:
ultraviolet absorbers;
flame retardants;
aluminum hydroxide;
filling agents; and
flattening agents.

61. The method according to claim 58 wherein the adding of solids is of solids from the group consisting of:
molecular sieves;
fumed silica; and
colloidal silica.

62. The method according to claim 47 wherein the pressuring is with an impregnant from the group consisting of:
silicones;
polyurethanes;
fluorosilicones;
modified polyurethane silicones;
modified silicone polyurethanes;
acrylics; and
polytetrafluoroethylene.

63. The method according to claim 47 wherein the impregnant comprises an admixture of:

(i) a liquid vinyl chainstopped polysiloxane having the formula,

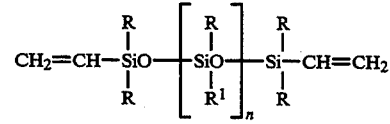

where R and R$^1$ are monovalent hydrocarbon radicals free of aliphatic unsaturation with at least 50 mole percent of the R$^1$ groups being methyl, and where n has a value sufficient to provide a viscosity up to about 5,000 centipoise to about 2,000,000 centipoise at 25° C.;

(ii) a resinous organopolysiloxane copolymer comprising:
(i) (R$^2$)$_3$SiO$_{0.5}$ units and SiO$_2$ units, or
(ii) (R$^3$)$_3$SiO$_{0.5}$ units, (R$^3$)$_2$SiO units and SiO$_2$ units, or
(iii) mixtures thereof, where R$^2$ and R$^3$ are selected from the group consisting of vinyl radicals and monovalent hydrocarbon radicals free of aliphatic unsaturation, where from about 1.5 to about 10 mole percent of the silicon atoms contain silicon-bonded vinyl groups, where the ratio of monofunctional units to tetrafunctional units is from about 0.5:1 to about 1:1, and the ratios of difunctional units to tetrafunctional units ranges up to about 0.1:1;

(iii) a platinum or platinum containing catalyst; and (iv) a liquid organohydrogenpolysiloxane having the formula:

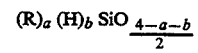

sufficient to provide from about 0.5 to about 1.0 silicon-bonded hydrogen atoms per silicon-bonded vinyl group, R is a monovalent hydrocarbon radical free of aliphatic unsaturation, and has a value of from about 1.0 to about 2.1, b has a value of from about 0.1 to about 1.0, and the sum of a and b is from about 2.0 to about 2.7, there being at least two silicon-bonded hydrogen atoms per molecule.

64. The method according to claim 47 wherein said impregnant exhibits a viscosity of about 5000 to about 1,000,000 centipoise at 25° C. prior to said pressure step.

65. The method according to claim 47 wherein said water-repellant chemical is saturated substantially upon fibers of a fabric web with interstices between adjacent fibers remaining substantially free of the water repellant chemical.

66. The method according to claim 65 wherein the water repellant chemical is deposited discontinuously on the fibers.

67. The method according to claim 65 wherein the impregnant is impregnated substantially only on the fibers, the impregnant being discontinuous and substantially at locations on said fibers other than those occupied by said discontinuously deposited water repellant chemical.

68. The method according to claim 47 wherein said pressuring is carried out by contacting one surface of the web with the impregnant carried by a roller.

69. The method according to claim 68 that further includes a second roller juxtaposed opposite said first-named roller and on the surface of the web opposite to that on which the impregnant is applied, said second roller rotating in the same direction as said first-named roller, thereby creating shearing forces within said web.

70. The method according to claim 47 wherein said pressuring is carried out by contacting one surface of said web with the impregnant followed by scraping said surface of excess impregnant.

71. The method according to claim 70 including the additional step of further scraping the surface, said further scraping providing further pressure to said web and removing any excess of said impregnant from the surface of the web.

72. The method according to claim 47 wherein the impregnant is curable and following the pressuring further comprising curing the impregnant in situ within the web in order to create a cured impregnant substantially enveloping the structural elements of the web.

73. The method according to claim 47 wherein said saturating with saturant and the pressuring with impregnant is upon a web consisting of fabric.

74. The method according to claim 73 wherein the fabric contains a plurality of yarns, each of the yarns comprising a plurality of fibers, the yarns defining major interstices between adjacent yarns through which both the saturant and the impregnant can permeate, said major interstices being greater in size than are the interstices defined by the adjacent fibers.

75. The method according to claim 74 wherein said fabric is woven.

76. The method according to claim 74 wherein said fabric is knitted.

77. The method according to claim 47 wherein the saturating with saturant and the pressuring with impregnant is upon a web consisting of leather.

78. A product produced by the method in accordance with claim 47.

79. A method of controllably impregnating an impregnant into a web having a plurality of structural elements defining a plurality of interstices therebetween, the method comprising:

providing an impregnant that (i) forms a surface contact angle of greater than 70° upon the surface of the web and will not appreciably flow into the web under atmospheric pressure within a time of 1 hour, and (ii) is a psuedoplastic or thixotropic non-Newtonian polymeric composition exhibiting reduced viscosity under shear forces;

saturating the web with a water repellent chemical of a capacity and concentration sufficient so as to, when left as a residue within the web upon the structural elements, create a surface contact angle with water of greater than 90° and a surface contact angle of greater than 70° with the impregnant at the exterior surface of the web; and pressuring the impregnant so that, by combination of shear forces from above and chemically reduced surface tension from below, the impregnant flows into the web in a thin film flow and substantially envelops the structural elements.

80. The method of claim 79 wherein the impregnant includes an additive that serves an additional functional purpose within the impregnated web and the method further includes the step of passing the impregnated web under tension into contact with one or more shear blades to position the additive on the surface of the enveloped structural elements.

81. The method according to claim 79 wherein the water repellant chemical comprises a fluorochemical.

82. The method according to claim 79 wherein the impregnant comprises a silicone.

83. The method according to claim 79 wherein the pressuring is by action of rolling against a tensioned web.

84. The method according to claim 79 wherein the web comprises fabric.

85. A method of treating a fabric made of fibers to substantially encapsulate the fabric's fibers, the method comprising:

saturating the fabric with liquid containing fluorochemicals, leaving fluorochemical residue upon the surfaces of the fabric's fibers to provide a fabric having a contact angle with water on an outer surface of the fabric of greater than 90°;

adding a substance into an impregnant comprising a curable polymeric, shear thinning, thixotropic composition that forms a surface contact angle of greater than 70° with the fabric containing the residue of the fluorochemicals; and impregnating the impregnant into the fabric sufficiently so that it substantially envelops the fibers of the fabric;

wherein the substance in the impregnant cannot adhere to surface regions of the fibers as a result of chemical repulsion of the impregnant by the fluorochemicals;

wherein the impregnant is facilitated to flow onto and into position substantially enveloping the fibers by the fluorochemical residue upon the surface of the fibers.

86. A flexible, porous substrate having a matrix with open cells therein, at least some of said cells being at least partially individually lined with a curable shear thinning thixotropic polymer composition in an approximately planar region spaced from and generally parallel to at least one major surface of said substrate, and at least some of said lined cells being open.

* * * * *

UNITED STATES PATENT AND TRADEMARK OFFICE
CERTIFICATE OF CORRECTION

PATENT NO. : 5,418,051
DATED : May 23, 1995
INVENTOR(S) : J. Michael Caldwell

It is certified that error appears in the above-indentified patent and that said Letters Patent is hereby corrected as shown below:

On the title page, item [63], after "Continuation of", insert --Ser. No. 680,645, Apr. 2, 1991, Pat. No. 5,209,965 which is a continuation of--.

On the title page, in the Abstract, line 9, correct the spelling of "therewithin"; line 14, delete "procuded" and insert --produced--.

Column 1, line 7, after "This application is a continuation of" insert --application Ser. No. 07/680,645, filed Apr. 2, 1991, now U.S. Pat. No. 5,209,965, which is a continuation of--.

Column 3, line 36, delete "the".

Column 4, line 17, delete "wed" and insert --web--.

Column 5, line 7, delete "differece" and insert --difference--.

Column 8, line 41, delete "fact" and insert --face--.

Column 11, line 1, delete "cause".

Column 16, line 60, delete "disperible" and insert --dispersible--; line 66, correct the spelling of "perfluoroalkyl".

Column 18, line 14, delete "carier" and insert --carrier--.

Column 27, line 48, delete "trated" and insert --treated--.

Column 53, line 56, delete "AATEC" and insert --AATCC--.

UNITED STATES PATENT AND TRADEMARK OFFICE
CERTIFICATE OF CORRECTION

PATENT NO. : 5,418,051
DATED : May 23, 1995
INVENTOR(S) : J. Michael Caldwell

It is certified that error appears in the above-indentified patent and that said Letters Patent is hereby corrected as shown below:

Col. 58, line 38, correct the spelling of "resistant; line 41, correct the spelling of "resistant"; line 42, in two places, correct the spelling of "resistant".

Col. 58, line 55, delete "5" and insert --15--.

Col. 59, line 65, correct the spelling of "resistant".

Signed and Sealed this

Fifth Day of September, 1995

Attest:

BRUCE LEHMAN

*Attesting Officer*  *Commissioner of Patents and Trademarks*